US010221192B2

(12) United States Patent
Guo et al.

(10) Patent No.: US 10,221,192 B2
(45) Date of Patent: Mar. 5, 2019

(54) COMPOUNDS AS TYROSINE KINASE MODULATORS

(71) Applicant: Allergan, Inc., Irvine, CA (US)

(72) Inventors: Xialing Guo, San Clemente, CA (US); Zhen Zhu, Foothill Ranch, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 15/599,333

(22) Filed: May 18, 2017

(65) Prior Publication Data
US 2018/0086774 A1    Mar. 29, 2018

Related U.S. Application Data

(63) Continuation of application No. 14/989,943, filed on Jan. 7, 2016, now abandoned, which is a continuation of application No. 14/444,161, filed on Jul. 28, 2014, now Pat. No. 9,340,555, which is a continuation-in-part of application No. 12/875,223, filed on Sep. 3, 2010, now Pat. No. 8,809,534.

(60) Provisional application No. 61/239,603, filed on Sep. 3, 2009, provisional application No. 61/306,616, filed on Feb. 22, 2010, provisional application No. 61/356,699, filed on Jun. 21, 2010, provisional application No. 61/360,531, filed on Jul. 1, 2010.

(51) Int. Cl.
*C07D 495/04* (2006.01)
*C07K 5/06* (2006.01)

(52) U.S. Cl.
CPC .............. *C07D 495/04* (2013.01); *C07K 5/06* (2013.01)

(58) Field of Classification Search
CPC ................................................... C07D 495/04
See application file for complete search history.

(56) References Cited

U.S. PATENT DOCUMENTS

| | | | |
|---|---|---|---|
| 4,966,849 A | 10/1990 | Vallee et al. |
| 5,217,999 A | 6/1993 | Levitzki et al. |
| 5,302,606 A | 4/1994 | Spada et al. |
| 5,330,992 A | 7/1994 | Eissenstat et al. |
| 5,792,783 A | 8/1998 | Tang et al. |
| 5,834,504 A | 11/1998 | Tang et al. |
| 5,883,113 A | 3/1999 | Tang et al. |
| 5,883,116 A | 3/1999 | Tang et al. |
| 5,886,020 A | 3/1999 | Tang et al. |
| 6,541,504 B1 | 4/2003 | Andrews et al. |
| 6,747,025 B1 | 6/2004 | Andrews et al. |
| 6,765,012 B2 | 7/2004 | Andrews et al. |
| 6,869,962 B2 | 3/2005 | Collins et al. |
| 7,208,500 B2 | 4/2007 | Lou et al. |
| 8,614,234 B2 | 12/2013 | Guo et al. |
| 8,809,534 B2 | 8/2014 | Guo et al. |
| 8,906,944 B2 | 12/2014 | Guo et al. |
| 9,328,103 B2 | 5/2016 | Guo et al. |
| 9,340,555 B2 | 5/2016 | Guo et al. |
| 9,475,801 B2 | 10/2016 | Guo et al. |
| 9,725,433 B2 | 8/2017 | Guo et al. |
| 2006/0116713 A1 | 6/2006 | Sepetka et al. |
| 2006/0133006 A1 | 6/2006 | Suto et al. |
| 2006/0287343 A1 | 12/2006 | Saavedra et al. |
| 2007/0197537 A1 | 8/2007 | Blake et al. |
| 2008/0046003 A1 | 2/2008 | Renger et al. |
| 2008/0054718 A1 | 3/2008 | Nishino et al. |
| 2008/0064718 A1 | 3/2008 | Saavedra et al. |
| 2008/0312232 A1 | 12/2008 | Kim et al. |
| 2009/0026440 A1 | 1/2009 | Kyono et al. |
| 2009/0118276 A1 | 5/2009 | Gopalsamy et al. |
| 2009/0264440 A1 | 10/2009 | Claridge et al. |
| 2009/0286984 A1 | 11/2009 | Raeppel et al. |
| 2010/0081675 A1 | 4/2010 | Minge et al. |

FOREIGN PATENT DOCUMENTS

| | | |
|---|---|---|
| EP | 0039051 | 11/1981 |
| JP | 2004528379 A | 9/2004 |
| JP | 2006511518 A | 6/2006 |
| JP | 2008528520 A | 7/2008 |
| JP | 2008533151 A | 8/2008 |
| WO | 1991-015495 | 10/1991 |

(Continued)

OTHER PUBLICATIONS

Canadian Patent Application No. 2,772,718, Preliminary Amendment, dated Apr. 26, 2012.

(Continued)

*Primary Examiner* — David K O'Dell

(74) *Attorney, Agent, or Firm* — Jonathan Bass

(57) ABSTRACT

The present invention is directed to novel compounds of Formula I. The compounds of the present invention are potent tyrosine kinase modulators, and are suitable for the treatment and prevention of diseases and conditions related to abnormal activities of tyrosine kinase receptors.

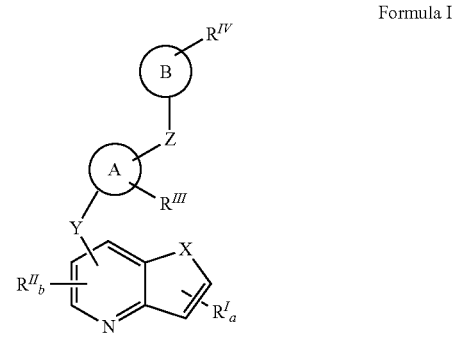

Formula I

2 Claims, No Drawings

(56) References Cited

FOREIGN PATENT DOCUMENTS

| WO | 1992-020642 | | 11/1992 |
|---|---|---|---|
| WO | 1992-021660 | | 12/1992 |
| WO | 1994-003427 | | 2/1994 |
| WO | 1994-014808 | | 7/1994 |
| WO | 9920617 | | 4/1999 |
| WO | 2002090352 | | 11/2002 |
| WO | 03087057 | | 10/2003 |
| WO | 2003-106462 | | 12/2003 |
| WO | 2004-052884 | | 6/2004 |
| WO | 2005-110410 | | 11/2005 |
| WO | 2006-067446 | | 6/2006 |
| WO | 2006081389 | | 8/2006 |
| WO | 2006081391 | | 8/2006 |
| WO | 2006099379 | | 9/2006 |
| WO | 2006-116713 | A1 | 11/2006 |
| WO | 2006-133006 | A2 | 12/2006 |
| WO | 2007071455 | | 6/2007 |
| WO | 2008-046003 | | 4/2008 |
| WO | 2008-063202 | | 5/2008 |
| WO | 2009-026717 | | 3/2009 |
| WO | 2009-070328 | | 6/2009 |
| WO | 2009103778 | | 8/2009 |
| WO | 2009-109035 | | 9/2009 |
| WO | 2011-028995 | | 3/2011 |

OTHER PUBLICATIONS

European Patent Application No. 10760159.3-2117, Communication pursuant to Rules 161(1) and 162 EPC, dated Apr. 27, 2012.
European Patent Application No. 10760159.3-2117, Publication, dated Jun. 13, 2012.
Japanese Patent Application No. 2012-528084, 2nd Office Action, dated Jan. 7, 2015.
Japanese Patent Application No. 2012-528084, Office Action, dated Aug. 4, 2014.
Japanese Patent Application No. 2012-528084, Response to Office Action, dated Nov. 10, 2014.
Ciulla, Thomas A., Diabetic Retinopathy and Diabetic Macular Edema, Diabetes Care, 2003, 2653-2654, 26 (9).
International Search Report and Written Opinion dated Dec. 20, 2010 for PCT/US10/47800 filed Sep. 3, 2010 in the name of Allergan, Inc.
International Search Report and Written Opinion dated Feb. 17, 2014 for PCT/US13/69337 filed Nov. 8, 2013 in the name of Allergan, Inc.
Albert O. Edwards et al., Molecular genetics of AMD and current animal models, Angiogensis, 2007, 119-132, 10.
Bart C. Kuenen et al., Efficacy and Toxicity of the Angiogensisi Inhibitor SU5416 as a Single Agent in Patients with Advacned Renal Cell Carcinoma, Melanoma, and Soft Tissue Sarcoma, Clinical Cancer Research, 2003, 1648-1655, 9.
Bolen, Joseph, Nonreceptor Tyrosine Protein Kinases, Oncogene, 1993, 2025-2031, 8.
Communications to the Editor, A Novel Solution-Stable. Water-Soluble Prodrug Type for Drugs Containing a Hydroxyl or an NH-Acidic Group, Journal of Medicinal Chemistry, Dec. 1989, 2503-2507, 32 (12).
Danieal M. Albert, The Complexity of Animal Model Generation for Complex Diseases, JAMA, 2010, 657-658, 303 (7).
Edelman, Jeffrey et al., Corticosteroids Inhibit VEGF-Induced Vascular Leakage in a Rabbit Model of Blood Retinal and Blood-Aqueous Barrier Breakdown, Experimental Eye Research, 2005, 249-258, 80.
Edelman, Jeffrey et al., Quantitative Image Analysis of Laser-induced Chorodial Neovascularization in Rat, Exp. Eye Res. 2000, 71: 523-533.
International Search Report & Written Opinion dated Dec. 3, 2010 for PCT/US10/47816 filed Sep. 3, 2010 filed in the name of Allergan, Inc.
J.I. Johnson et al., Relationships between drug activity in NCI preclinical in vitro and in vivio models and early clinical trials, British Journal of Cancer, 2001, 1424-1431, 84.
Jellinek, Derek et al, Inhibition of Receptor Binding by High-Affinity RNA Ligands to Vascular Endothelial Growth Factor, Biochemistry, 1994, 10450-10456, 33.
Joseph V. Simone, Part XIV: Oncology, Cecil Textbook of Medicine, 1996, 1004-1010, 1.
Kendall, Richard et al, Inhibition of Vascular Endothelial Cell Growth Factor Activity by an Endogenously Encoded Soluble Receptor, Proc. Natl. Acad. Sci., Nov. 1993, 10705-10709, 90.
Kim, Jin et al, Inhibition of Vascular Endothelial Growth Factor-Induced Angiogenesis Suppresses Tumour Growth in Vivo, Nature, Apr. 29, 1993, 841-844, 362(6423).
Kinsella, J.L. et al, Protein Kinase C Regulates Endothelial Cell Tube Formation on Basement Membrane Matrix, Matrigel, Experimental Cell Research, 1992, 56-62, 199.
Mariani, M. et al., Inhibition of Angiogenesis by FCE 26806, A Potent Tyrosine Kinase Inhibitor, Proceedings of the American Association for Cancer Research, Mar. 1994, Abstract 2268, 35.
Plowman, Gregory et al, Receptor Tyrosine Kinases as Targets for Drug Intervention, Drug News & Perspectives, Aug. 1994, 334-339, 7(6).
Raeppel S et al., Identification of a novel series of potent RON receptor tyrosine kinase inhibitors, Bioorganic & Medicinal Chemistry Letters, May 1, 2010, pp. 2745-2749, XP027012825, vol. 20, No. 9, Elsevier Ltd.
Robert Auerbach et al., Angiogensis Assays: A Critical Overview, Clinical Chemistry, 2003, 32-40, 49 (1).
Silverman, Richard B., Prodrugs and Delivery Systems (Chapter 8), The Organic Chemistry of Drug Delivery and Drug Design and Drug Action Second Edition, 2004, 496-557.
Takano, S. et al, Inhibition of Angiogenesis by a Novel Diaminoanthraquinone that Inhibits Protein Kinase C, Protein Kinases, Wednesday 1993, 2072-2077, Abstract 2 pages, 358a, 2076.
Trisha Gura, Cancer Models: Systems for Identifying New Drugs are Often Faulty, Science, 1997, 1041-1042, 278.
Wright, Paul et al, Inhibition of Angiogenesis in Vitro and in Ovo with an inhibitor of Cellular Protein Kinases, MDL 27032, Journal of Cellular Physiology, Sep. 1992, 448-457, 152(3).

COMPOUNDS AS TYROSINE KINASE MODULATORS

CROSS REFERENCE TO RELATED APPLICATIONS

This application is a continuation of U.S. patent application Ser. No. 14/989,943, filed Jan. 7, 2016, which is a continuation of U.S. patent application Ser. No. 14/444,161, filed Jul. 28, 2014, now U.S. Pat. No. 9,340,555, issued May 17, 2016, which is a continuation in part of U.S. application Ser. No. 12/875,223, filed Sep. 3, 2010, now U.S. Pat. No. 8,809,534, issued Aug. 19, 2014, which claims priority under 35 U.S.C. 119(e) to U.S. Provisional Application Nos. 61/239,603, filed on Sep. 3, 2009, 61/306,616, filed on Feb. 22, 2010, 61/356,699 filed on Jun. 21, 2010 and 61/360,531 filed on Jul. 1, 2010, each of which are incorporated herein by reference in their entireties, and serve as the basis for a priority and/or benefit claim of the present application.

FIELD OF THE INVENTION

The present invention is directed to novel compounds with multiple aromatic components capable of modulating, regulating and/or inhibiting tyrosine kinase signal transduction. The present invention is also directed to methods of prevention and/or treatment of disorders related to unregulated tyrosine kinase signal transduction, including but not limited to, cell growth disorders, metabolic disorders, blood vessel proliferative disorders, inflammatory disorders, neurodegenerative diseases and immune disorders.

BACKGROUND OF THE INVENTION

Protein tyrosine kinases ("PTKs") play an important role in the control of cell growth and differentiation. PTKs comprise a large and diverse class of proteins having enzymatic activity. PTKs can be of the receptor-type (having extracellular, transmembrane and intracellular domains) or the non-receptor type (being wholly intracellular). For example, signal transduction mediated by receptor tyrosine kinases ("RTKs") is initiated by extracellular interaction with a specific growth factor (i.e., a ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to RTKs, it has been shown also that tyrosine phosphorylation sites function as high-affinity binding sites for SH2 (src homology) domains of signaling molecules. Several intracellular substrate proteins that associate with RTKs have been identified and are divided into two principal groups: (1) substrates which have a catalytic domain; and (2) substrates which lack a catalytic domain but serve as adapters and associate with catalytically active molecules. The specificity of the interactions between receptors or proteins and SH2 domains of their substrates is determined by the amino acid residues immediately surrounding the phosphorylated tyrosine residue. Differences in binding affinities between SH2 domains and the amino acid sequences surrounding the phosphotyrosine residues on particular receptors are consistent with the observed differences in their substrate phosphorylation profiles. These observations suggest that the function of each RTK is determined not only by its pattern of expression and ligand availability, but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses. At present, at least nineteen distinct RTK subfamilies have been identified. One RTK subfamily, designated the HER subfamily, is believed to be comprised of EGFR, HER2, HER3 and HER4. Ligands to the HER subfamily of receptors include epithelial growth factor (EGF), TGF-α, amphiregulin, HB-EGF, betacellulin and heregulin. The second subfamily of RTKs, designated the insulin subfamily, is comprised of the INS-R, the IGF-1R and the IR-R. The third RTK subfamily, the "PDGF" family, includes the PDGF α and β receptors, CSFIR, c-kit and FLK-II. Another subfamily of RTKs, identified as the FLK family, is believed to be comprised of the kinase insert domain-receptor fetal liver kinase-1 (KDR/FLK-1), the fetal liver kinase 4 (FLK-4) and the fms-like tyrosine kinase 1 (flt-1). Each of these receptors was initially believed to be a receptor for hematopoietic growth factors. Two other subfamilies of RTKs have been designated as the FGF receptor family (FGFR1, FGFR2, FGFR3 and FGFR4) and the Met subfamily (c-met and Ron). Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs, and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the protein tyrosine kinases (PTKs), whether an RTK or non-receptor tyrosine kinase, have been found to be involved in cellular signaling pathways leading to cellular signal cascades and pathogenic conditions such as cancer, psoriasis and hyper immune responses. In view of the importance of PTKs to the control, regulation and modulation of cell proliferation and the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966, 849), soluble receptors and antibodies (Kendall & Thomas, 1994, Proc. Nat'l Acad. Sci 90: 10705-09; Kim, et al, 1993, Nature 362: 841-844), RNA ligands (Jellinek, et al, Biochemistry 33: 10450-56); Takano, et al, 1993, Mol. Bio. Cell 4:358A; Kinsella, et al, 1992, Exp. Cell Res. 199: 56-62; Wright, et al, 1992, J. Cellular Phys. 152: 448-57) and tyrosine kinase inhibitors (U.S. Pat. No. 5,330,992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinyleneazaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

In addition, other small molecules were studied as tyrosine kinase inhibitors, such as the compounds disclosed in U.S. Pat. Nos. 6,765,012; 6,541,504; 6,747,025; 5,792,783; 5,834,504; 5,883,113; 5,883,116 and 5,886,020, all of which are incorporated by reference in their entireties.

The identification and use of compounds which specifically inhibit signal transduction by modulating the activity of receptor and non-receptor tyrosine is one aspect of the present invention.

SUMMARY OF THE INVENTION

The present invention is directed to compounds represented by Formula I capable of modulating, regulating and/or inhibiting tyrosine kinase signal transduction, and uses of the compounds and compositions incorporating the compounds for disease treatment and prevention.

The compounds of the present invention can be found in general Formula I:

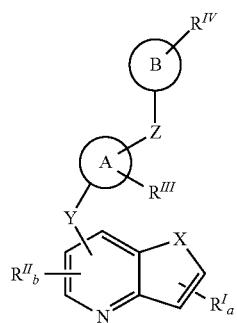

Formula I wherein
X is selected from the group consisting of $NR^1$, O, $S(O)_n$;
n is 0 or an integer of from 1 to 2;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

$R^I$ is selected from the group consisting of hydrogen, halogen, $C_1$ to $C_8$ alkyl, $S(O)_fR^4$, $(CR^5R^6)_dC(O)OR^4$, $S(O)_f(CR^5R^6)_dC(O)OR^4$, $(CR^5R^6)_dAr$, $NR^4(CR^5R^6)_d$ Ar, $O(CR^5R^6)_dAr$, $S(O)_f(CR^5R^6)_dAr$, $(CR^5R^6)_aS(O)_f$ $R^4$, $NR^4(CR^5R^6)_aS(O)_fR^4$, $O(CR^5R^6)_aS(O)_fR^4$, $S(O)_f$ $(CR^5R^6)_eS(O)_fR^4$, $(CR^5R^6)_dC(O)N(R^4)_2$, $NR^4(CR^5$ $R^6)_dC(O)N(R^4)_2$, $O(CR^5R^6)_dC(O)N(R^4)_2$, $S(O)_f$ $(CR^5R^6)_eC(O)N(R^4)_2$, $(CR^5R^6)_dOR^4$, $S(O)_f(CR^5$ $R^6)_dOR^4$, $(CR^5R^6)_dOSO_2R^4$, $S(O)_f(CR^5R^6)_eOSO_2R^4$, $(CR^5R^6)_dP(O)(OR^4)_2$, $S(O)_f(CR^5R^6)_eP(O)(OR^4)_2$, $OC(O)(CR^5R^6)_dN(R^4)_2$, $C(O)(CR^5R^6)_dN(R^4)_2$, $C(O)$ $N=S(O)R^5R^6$, $NR^2C(O)(CR^5R^6)_dN(R^4)_2$, $(CR^5R^6)_dR^5$, $S(O)_f(CR^5R^6)_dR^5$, $HNC(O)R^4$, $HN—C$ $(O)OR^4$, $(CR^5R^6)_dN(R^4)_2$, $S(O)_f(CR^5R^6)_dN(R^4)_2$, $OC(O)OR^4$, $(CR^5R^6)_dC(O)(CR^5R^6)_dR^4$, $(CR^5R^6)_dC$ $(O)(CR^5R^6)_dOR^4$, and $(CR^5R^6)_dC(O)(CR^5R^6)_dN(R^4)_2$, wherein each $R^4$ is independently selected from the group consisting of hydrogen, hydroxyl, $C_1$-$C_8$ alkyl, aryl, $C_1$-$C_8$ hydroxyalkyl, $C_1$-$C_8$ alkoxyalkyl, $(CR^5R^6)_d$ and $N(R^4)_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of $R^5$; wherein $R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate and $CR^5R^6$ may represent a carbocyclic or heterocyclic ring of from 5 to 6 carbons or alternatively, $(CR^5R^6)_d$ and $(CR^5R^6)_e$ may form a 3-7 membered carbocyclic or heterocyclic ring, wherein the ring may be optionally substituted with up to three of hydroxyl, halo, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl and sulfonate;
a is 0 or an integer of from 1 to 3;
d is 0 or an integer of from 1 to 5;
e is an integer of from 1 to 4;
f is 0 or an integer of from 1 to 2;
$R^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, $(NR^2R^3)$ alkoxy, $(NR^2R^3)$alkenyl, $(NR^2R^3)$alkyl, $(NR^2R^3)$carbonylalkenyl, and $(NR^2R^3)$carbonylalkyl, wherein $R^2$ and $R^3$ are independently selected from the group consisting of hydrogen, alkyl, alkylcarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
b is 0 or an integer of from 1 to 2;
Y is selected from the group consisting of
(1) —$(CH_2)g$-O—$(CH_2)h$-;
(2) —$(CH_2)g$-$NR^1$—$(CH_2)h$-;
(3) —$(CH_2)g$-CO—$(CH_2)h$-;
(4) —$(CH_2)g$-$C(O)NR^2$—$(CH_2)h$-;
(5) —$(CH_2)g$-$NR^2C(O)$—$(CH_2)h$-;
(6) —$(CH_2)g$-$(CH_2)h$-;
(7) —$(CH_2)g$-CH(OH)—$(CH_2)h$-;
(8) —$(CH_2)g$-C≡C—$(CH_2)h$-;
and (9) a single bond;

wherein
g is 0 or an integer of from 1 to 3;
h is 0 or an integer of from 1 to 3;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
$R^2$ is selected from the group consisting of hydrogen, alkyl, alkylcarbonyl, alkoxycarbonyl, alkylsulfonyl, arylsulfonyl, haloalkylsulfonyl, and heterocyclylsulfonyl;
Ring A is selected from the group consisting of:

(i) Phenyl;
(ii) Naphthyl;
(iii) A 5 or 6 membered monocyclic heteroaryl group which has 1-5 heteroatoms independently selected from the group consisting of O, N and S;
and (iv) An 8 to 10 membered bicyclic heteroaryl group which has 1-6 heteroatoms independently selected from the group consisting of O, N and S;
$R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, $C_1$-$C_6$ dialkylamino, halogen, cyano, and nitro;
Z is selected from the group consisting of
(1') $(CH_2)_iN(R^7)C(O)N(R^8)(CH_2)_j$;
(2') $(CH_2)_iN(R^7)C(S)N(R^8)(CH_2)_j$;
(3') $(CH_2)_iN(R^7)C(O)$;
(4') $C(O)N(R^8)(CH_2)_j$;
(5') $(CH_2)_iN(R^7)S(O)_2$;
and (6') $S(O)_2N(R^8)(CH_2)_j$;
wherein
i is 0 or 1;
j is 0 or 1;
$R^7$ and $R^8$ are independently selected from the group consisting of hydrogen and alkyl.
Ring B is selected from the group consisting of:

(i') Phenyl;
(ii') Naphthyl;
(iii') A 5 or 6 membered monocyclic heteroaryl group which has 1-3 heteroatoms independently selected from the group consisting of O, N and S;
and (iv') An 8 to 10 membered bicyclic heteroaryl group which has 1-3 heteroatoms independently selected from the group consisting of O, N and S;
$R^{IV}$ represents optionally 1-3 substituents, independently selected from the group consisting of alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^9R^{10}$; wherein $R^9$ and $R^{10}$ are independently selected from the group consisting of hydrogen, alkyl, alkylcarbonyl, aryl, arylalkyl, cycloalkyl, cycloalkylalkyl, heterocyclyl, and heterocyclylalkyl.

Some embodiments of the present invention are included in the following paragraphs:

1) A compound according to Formula I, including any tautomer, stereoisomer, diastereoisomeric form, polymorphic form, crystal form, a solvate, a hydrate, a metabolite, a pharmaceutically acceptable salt or prodrug, mixture of different stereoisomers, mixture of different crystal forms.
2) A compound of Formula I in the form of a prodrug.
3) The compound according to paragraph 1, wherein Y is selected from the group consisting of
   (a) —$(CH_2)g$-C=C—$(CH_2)h$-;
   (b) —$(CH_2)g$-$NR^1$—$(CH_2)h$-;
   (c) —$(CH_2)g$-CO—$(CH_2)h$-;
   (d) —$(CH_2)g$-C(O)$NR^2$—$(CH_2)h$-;
   (e) —$(CH_2)g$-$NR^2$C(O)—$(CH_2)h$-;
   (f) —$(CH_2)g$-$(CH_2)h$-;
   (g) —$(CH_2)g$-CH(OH)—$(CH_2)h$-;
   (h) —$(CH_2)g$-O—$(CH_2)h$-;
   and (i) a single bond.
4) The compound according to paragraphs 1-3, wherein Z is selected from the group consisting of $(CH_2)_iN(R^7)$ $C(O)N(R^8)(CH_2)_j$, $(CH_2)_iN(R^7)C(S)N(R^8)(CH_2)_j$, $(CH_2)_iN(R^7)C(O)$, and $C(O)N(R^8)(CH_2)_j$.
5) The compound according to paragraphs 1-4, wherein X is NH.
6) The compound according to paragraphs 1-5, wherein Ring A and Ring B are independently selected from the group consisting of

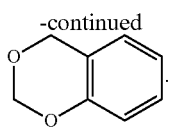

7) The compound according to paragraph 6, wherein X is S.
8) The compound according to paragraph 1, which can be further represented by Formula II:

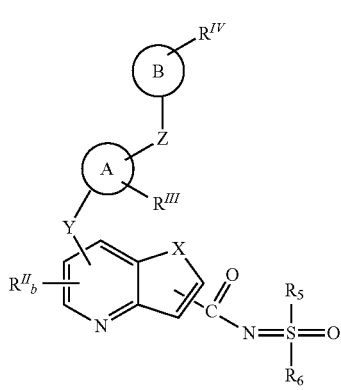

Formula II including any tautomer, stereoisomer, diastereoisomeric form, crystal form, polymorphic form, mixture of stereoisomers, mixture of polymorphic forms, mixture of crystal forms, a solvate, a hydrate, a metabolite, a pharmaceutically acceptable salt or a prodrug.

9) The compound according to paragraphs 1-8, wherein $R^1$ is selected from the group consisting of hydrogen, halogen, $C_1$ to $C_8$ alkyl, $(CR^5R^6)_dC(O)OR^4$, $(CR^5R^6)_dAr$, $NR^4(CR^5R^6)_dAr$, $(CR^5R^6)_dC(O)N(R^4)_2$, $NR^4(CR^5R^6)_dC(O)N(R^4)_2$, $O(CR^5R^6)_dC(O)N(R^4)_2$, $(CR^5R^6)_dOR^4$, $OC(O)(CR^5R^6)_dN(R^4)_2$, $C(O)(CR^5R^6)_dN(R^4)_2$, $NR^2C(O)(CR^5R^6)_dN(R^4)_2$, $(CR^5R^6)_dR^5$, $HNC(O)R^4$, $HN-C(O)OR^4$, $(CR^5R^6)_dN(R^4)_2$, $S(O)_f(CR^5R^6)_dN(R^4)_2$, $OC(O)OR^4$, $(CR^5R^6)_dC(O)(CR^5R^6)_dR^4$, $(CR^5R^6)_dC(O)(CR^5R^6)_dOR^4$, and $(CR^5R^6)_dC(O)(CR^5R^6)_dN(R^4)_2$, wherein each $R^4$ is independently selected from the group consisting of hydrogen, hydroxyl, $C_1$-$C_8$ alkyl, aryl, $C_1$-$C_8$ hydroxyalkyl, $C_1$-$C_8$ alkoxyalkyl, $(CR^5R^6)_d$ and $N(R^4)_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of $R^5$; wherein $R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate and $CR^5R^6$ may represent a carbocyclic or heterocyclic ring of from 5 to 6 carbons or alternatively, $(CR^5R^6)_d$ and $(CR^5R^6)_e$ may form a 3-7 membered carbocyclic or heterocyclic ring, wherein the ring may be optionally substituted with up to three of hydroxyl, halo, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl and sulfonate.

10) A compound selected from the group consisting of

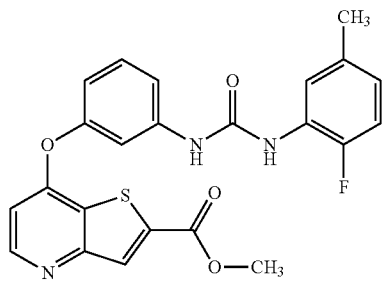

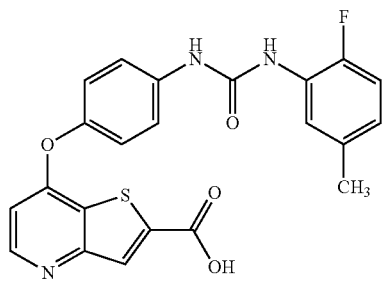

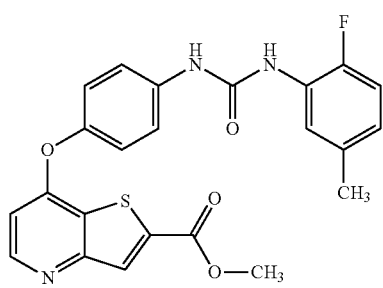

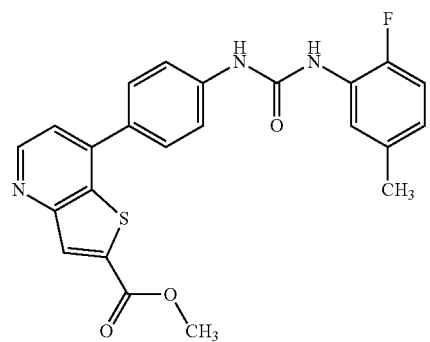

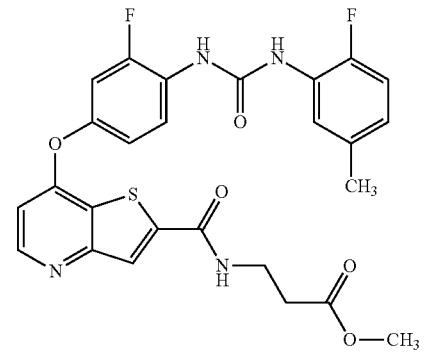

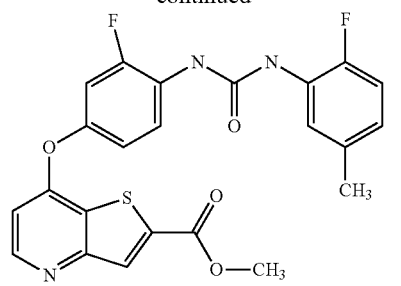
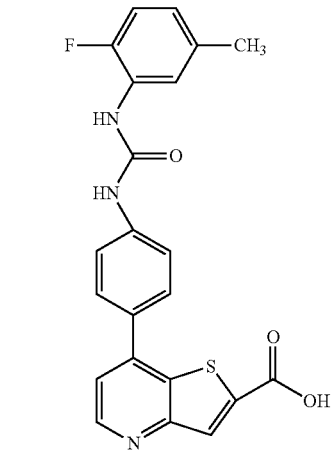
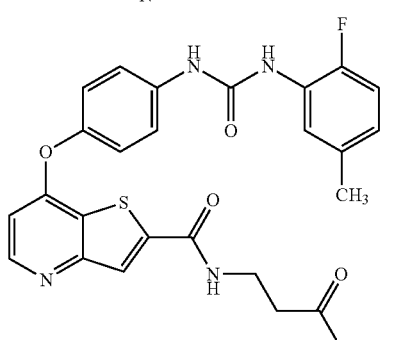
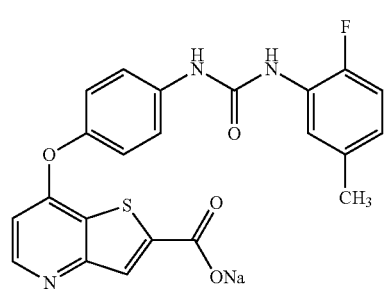
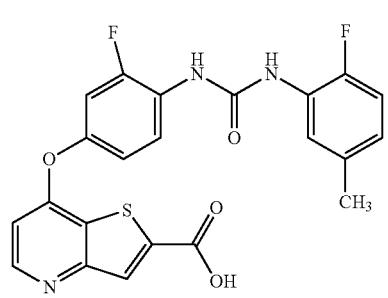
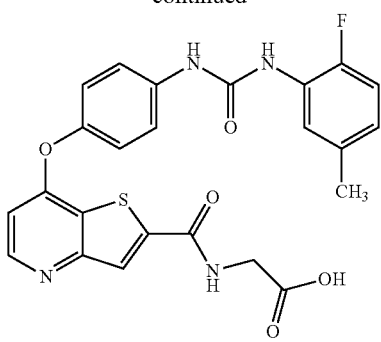
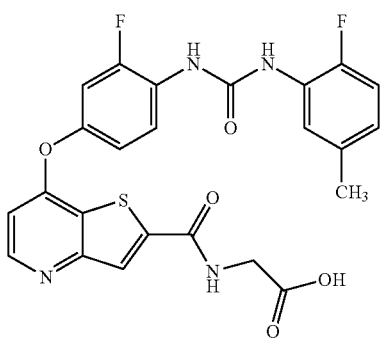
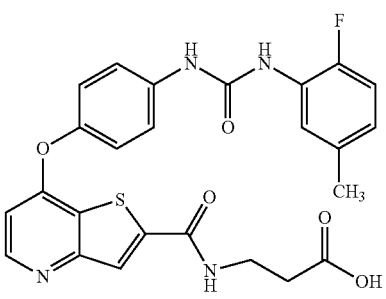
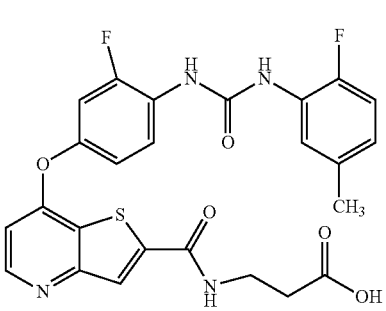
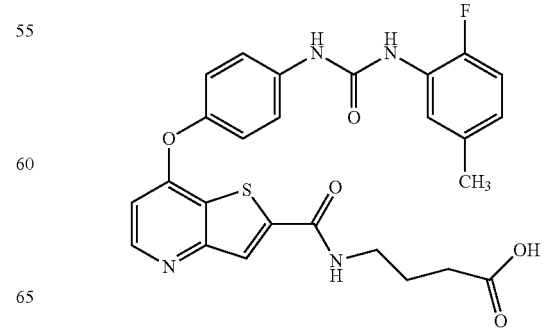

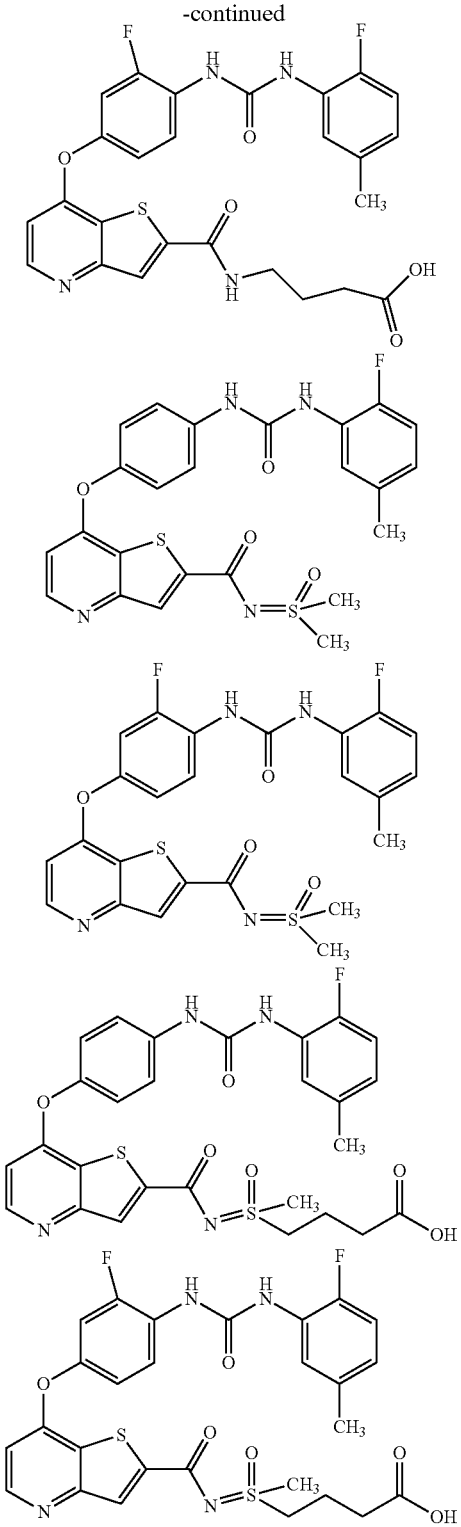

11) A method of use of the compounds of paragraphs 1-10, wherein the compounds are used as tyrosine kinase modulators.
12) Use of the compounds of paragraphs 1-10 in the preparation of a medicament for the treatment or prevention of diseases or conditions related with unregulated tyrosine kinase activities, comprising administering a therapeutically effective amount of the compound of paragraphs 1-10 together with a pharmaceutically acceptable carrier;
13) The use of paragraph 12, wherein the diseases or conditions are selected from the group consisting of cell growth and metabolic disorders, blood vessel proliferative disorders, inflammatory disorders, neurodegenerative diseases, and immune disorders.
14) The use of paragraphs 12-13 wherein the diseases or conditions are selected from the group consisting of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, inflammation, neurodegenerative diseases and immune disorders.
15) A pharmaceutical composition comprising a therapeutic effective amount of a compound according to paragraphs 1-10 together with a pharmaceutically acceptable carrier which is suitable for systematic, parenteral, local or topical delivery.
16) The pharmaceutical composition of paragraph 15 which are in the form selected from the group consisting of tablets, capsules, intravenous injections, intramuscular injections, local injections, topical creams, gels and ointments, eye drops, ophthalmic solutions, ophthalmic suspensions, ophthalmic emulsions, intravitreal injections, subtenon injections, ophthalmic biodrodible implant, and non-bioeordible ophthalmic inserts or depots.
17) Use of the compounds of paragraph 10 in the preparation of a medicament for the treatment of diseases and conditions, wherein the medicament contains a pharmaceutical acceptable composition according to paragraphs 15 and 16.

DETAILED DESCRIPTION OF THE INVENTION

The present invention is directed to a series of compounds with multiple aromatic components useful as protein tyrosine kinase inhibitors. The compounds of the present invention are useful for treating diseases related to unregulated tyrosine kinase signal transduction, for example, cancer, blood vessel proliferative disorders, fibrotic disorders, and neurodegenerative diseases. In particular, compounds of the present invention are useful for the treatment of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, inflammation, neurodegenerative diseases and immune disorders.

1. Compounds of the Invention

The present invention is directed to a compound of Formula I:

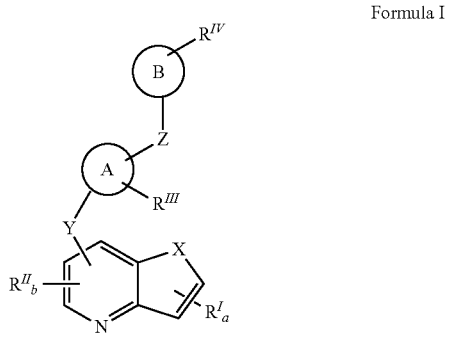

Formula I wherein

X is selected from the group consisting of $NR^1$, O, $S(O)_n$;

n is 0 or an integer of from 1 to 2;

$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

$R^I$ is selected from the group consisting of hydrogen, halogen, $C_1$ to $C_8$ alkyl, $S(O)_fR^4$, $(CR^5R^6)_dC(O)OR^4$, $S(O)_f(CR^5R^6)_dC(O)OR^4$, $(CR^5R^6)_dAr$, $NR^4(CR^5R^6)_dAr$, $O(CR^5R^6)_dAr$, $S(O)_f(CR^5R^6)_dAr$, $(CR^5R^6)_dS(O)_fR^4$, $NR^4(CR^5R^6)_dS(O)_fR^4$, $O(CR^5R^6)_dS(O)_fR^4$, $S(O)_f(CR^5R^6)_dS(O)_fR^4$, $(CR^5R^6)_dC(O)N(R^4)_2$, $NR^4(CR^5R^6)_dC(O)N(R^4)_2$, $O(CR^5R^6)_dC(O)N(R^4)_2$, $S(O)_f(CR^5R^6)_eC(O)N(R^4)_2$, $(CR^5R^6)_dOR^4$, $S(O)_f(CR^5R^6)_dOR^4$, $(CR^5R^6)_dOSO_2R^4$, $S(O)_f(CR^5R^6)_eOSO_2R^4$, $(CR^5R^6)_dP(O)(OR^4)_2$, $S(O)_f(CR^5R^6)_eP(O)(OR^4)_2$, $OC(O)(CR^5R^6)_dN(R^4)_2$, $C(O)(CR^5R^6)_dN(R^4)_2$, $C(O)N=S(O)R^5R^6$, $NR^2C(O)(CR^5R^6)_dN(R^4)_2$, $(CR^5R^6)_dR^5$, $S(O)_f(CR^5R^6)_dR^5$, $HNC(O)R^4$, $HN-C(O)OR^4$, $(CR^5R^6)_dN(R^4)_2$, $S(O)_f(CR^5R^6)_dN(R^4)_2$, $OC(O)OR^4$, $(CR^5R^6)_dC(O)(CR^5R^6)_dR^4$, $(CR^5R^6)_dC(O)(CR^5R^6)_dOR^4$, and $(CR^5R^6)_dC(O)(CR^5R^6)_dN(R^4)_2$, wherein each $R^4$ is independently selected from the group consisting of hydrogen, hydroxyl, $C_1$-$C_8$ alkyl, aryl, $C_1$-$C_8$ hydroxyalkyl, $C_1$-$C_8$ alkoxyalkyl, $(CR^5R^6)_d$ and $N(R^4)_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of $R^5$; wherein $R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate and $CR^5R^6$ may represent a carbocyclic or heterocyclic ring of from 5 to 6 carbons or alternatively, $(CR^5R^6)_d$ and $(CR^5R^6)_e$ may form a 3-7 membered carbocyclic or heterocyclic ring, wherein the ring may be optionally substituted with up to three of hydroxyl, halo, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl and sulfonate;

a is 0 or an integer of from 1 to 3;

d is 0 or an integer of from 1 to 5;

e is an integer of from 1 to 4;

f is 0 or an integer of from 1 to 2;

$R^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, $(NR^2R^3)$alkoxy, $(NR^2R^3)$alkenyl, $(NR^2R^3)$alkyl, $(NR^2R^3)$carbonylalkenyl, and $(NR^2R^3)$carbonylalkyl, wherein $R^2$ and $R^3$ are independently selected from the group consisting of hydrogen, alkyl, alkylcarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

b is 0 or an integer of from 1 to 2;

Y is selected from the group consisting of (1') —$(CH_2)_g$-O—$(CH_2)_h$-;
(2') —$(CH_2)_g$-$NR^1$—$(CH_2)_h$-;
(3') —$(CH_2)_g$-CO—$(CH_2)_h$-;
(4') —$(CH_2)_g$-C(O)$NR^2$—$(CH_2)_h$-;
(5') —$(CH_2)_g$-$NR^2$C(O)—$(CH_2)_h$-;
(6') —$(CH_2)_g$-$(CH_2)_h$-;
(7') —$(CH_2)_g$-CH(OH)—$(CH_2)_h$-;
(8') —$(CH_2)_g$-C≡C—$(CH_2)_h$-;
and (9') a single bond;

wherein g is 0 or an integer of from 1 to 3;

h is 0 or an integer of from 1 to 3;

$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl($NR^2R^3$), wherein $R^2$ and $R^3$ are independently selected from the group consisting of hydrogen, alkyl, alkylcarbonyl, alkoxycarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;

$R^2$ is selected from the group consisting of hydrogen, alkyl, alkylcarbonyl, alkoxycarbonyl, alkylsulfonyl, arylsulfonyl, haloalkylsulfonyl, and heterocyclylsulfonyl;

Ring A is selected from the group consisting of:

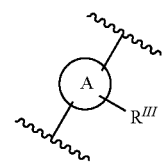

(i) Phenyl;
(ii) Naphthyl;
(iii) A 5 or 6 membered monocyclic heteroaryl group which has 1-5 heteroatoms independently selected from the group consisting of O, N and S;
and (iv) An 8 to 10 membered bicyclic heteroaryl group which has 1-6 heteroatoms independently selected from the group consisting of O, N and S;

$R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, C1-C6 dialkylamino, halogen, cyano, and nitro;

Z is selected from the group consisting of
- (1') $(CH_2)_iN(R^7)C(O)N(R^8)(CH_2)_j$;
- (2') $(CH_2)_iN(R^7)C(S)N(R^8)(CH_2)_j$;
- (3') $(CH_2)_iN(R^7)C(O)$;
- (4') $C(O)N(R^8)(CH_2)_j$;
- (5') $(CH_2)_iN(R^7)S(O)_2$;
- and (6') $S(O)_2N(R^8)(CH_2)_j$.

wherein
i is 0 or 1;
j is 0 or 1;
$R^7$ and $R^8$ are independently selected from the group consisting of hydrogen and alkyl;

Ring B is selected from the group consisting of:

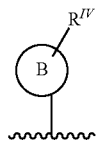

(i') Phenyl;
(ii') Naphthyl;
(iii') A 5 or 6 membered monocyclic heteroaryl group which has 1-3 heteroatoms independently selected from the group consisting of O, N and S;
and (iv') An 8 to 10 membered bicyclic heteroaryl group which has 1-3 heteroatoms independently selected from the group consisting of O, N and S;
$R^{IV}$ represents optionally 1-3 substituents, independently selected from the group consisting of alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^9R^{10}$; wherein $R^9$ and $R^{10}$ are independently selected from the group consisting of hydrogen, alkyl, alkylcarbonyl, aryl, arylalkyl, cycloalkyl, cycloalkylalkyl, heterocyclyl, and heterocyclylalkyl.

Unless otherwise indicated, reference to a compound should be construed broadly to include compounds, pharmaceutically acceptable salts, prodrugs, tautomers, stereoisomers, diastereoisomers, alternate solid forms, crystal forms, polymorphic forms, hydrates, solvates, metabolites, mixtures of stereoisomers, mixtures of crystal forms, non-covalent complexes, and combinations thereof, of a chemical entity of a depicted structure or a chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acids), one or more protonated basic groups (e.g. amines), or both (e.g. zwitterions).

A "prodrug" is a compound, which when administered to the body of a subject (such as a mammal), breaks down in the subject's metabolic pathway to provide an active compound of Formula I. More specifically, a prodrug is an active or inactive "masked" compound that is modified chemically through in vivo physiological action, such as hydrolysis, metabolism and the like, into a compound of this invention following administration of the prodrug to a subject or patient. One common form of a prodrug is a masked carboxylic acid group. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion. Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be amorphous forms, crystal forms, polymorphs, and the mixtures thereof.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

2. Uses, Formulation and Administration

The present invention is also directed to the use of the compounds as protein tyrosine kinase modulators and inhibitors. These compounds can be used to treat diseases related to unregulated tyrosine kinase signal transduction, for example, various cancers, blood vessel proliferative disorders, fibrotic disorders, and neurodegenerative diseases. In particular, compounds of the present invention are useful for the treatment and/or prevention of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, inflammation, neurodegenerative diseases and immune disorders in the human being.

The present invention is also directed to the preparation of a medicament for the treatment and prevention of diseases and conditions related with abnormal activities of tyrosine kinase receptors. The medicament contains a pharmaceutical acceptable composition, which comprises the therapeutic effective amount of the compounds of present invention, together with a pharmaceutical acceptable carrier.

For the purposes of this disclosure, "treat," "treating," or "treatment" refer to the diagnosis, cure, mitigation, treatment, or prevention of disease or other undesirable conditions.

The pharmaceutical acceptable compositions contain therapeutic effective amount of the compounds of the present invention. These compositions can be used as a medicament and administered to a mammal, such as a person, in need thereof. Different types of suitable dosage forms and medicaments are well known in the art, and can be readily adapted for delivery of the compounds of the present invention, such as, but not limited to, systematic, parenteral, local and topical delivery. The dosage forms can be tablets, capsules, intravenous injections, intramuscular injections, local injections, topical creams, gels and ointments, eye drops, ophthalmic solutions, ophthalmic suspensions, ophthalmic emulsions, intravitreal injections, subtenon injections, ophthalmic biodrodible implant, and non-bioeordible ophthalmic inserts or depots, nasal sprays and ointment, various rectal or vaginal preparations.

3. Examples

TABLE 1

Exemplified Compounds of the Present Invention

| Compound | Structure | MW | Chemical Name |
|---|---|---|---|
| F1 | 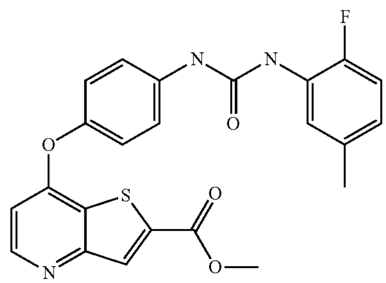 [SMILES: COC(=O)c1cc2nccc(Oc3ccc(NC(=O)Nc4cc(C)ccc4F)cc3)c2s1] | 451 | methyl 7-[4-({[(2-fluoro-5-methylphenyl)amino]carbonyl}amino)phenoxy]thieno[3,2-b]pyridine-2-carboxylate |
| F2 | 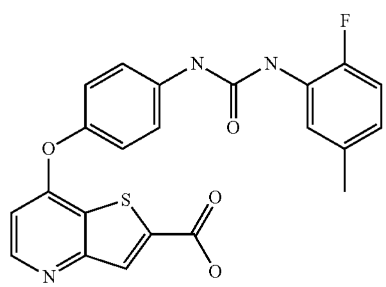 [SMILES: Cc1ccc(F)c(NC(=O)Nc2ccc(Oc3ccnc4cc(C(=O)O)sc34)cc2)c1] | 437 | 7-[4-({[(2-fluoro-5-methylphenyl)amino]carbonyl}amino)phenoxy]thieno[3,2-b]pyridine-2-carboxylic acid |
| F3 | 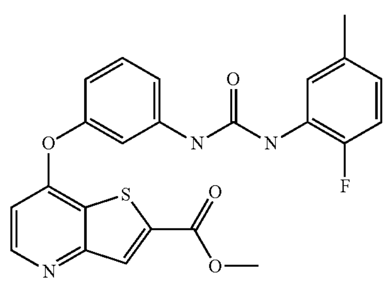 [SMILES: COC(=O)c1cc2nccc(Oc3cccc(NC(=O)Nc4cc(C)ccc4F)c3)c2s1] | 451 | methyl 7-[3-({[(2-fluoro-5-methylphenyl)amino]carbonyl}amino)phenoxy]thieno[3,2-b]pyridine-2-carboxylate |
| F4 | 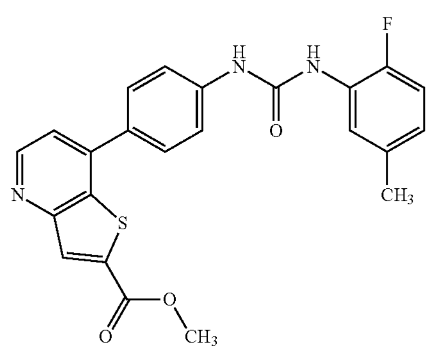 [SMILES: COC(=O)c1cc2nccc(-c3ccc(NC(=O)Nc4cc(C)ccc4F)cc3)c2s1] | 435 | methyl 7-[4-({[(2-fluoro-5-methylphenyl)amino]carbonyl}amino)phenyl]thieno[3,2-b]pyridine-2-carboxylate |

TABLE 1-continued

Exemplified Compounds of the Present Invention

| Compound | Structure | MW | Chemical Name |
|---|---|---|---|
| F5 | 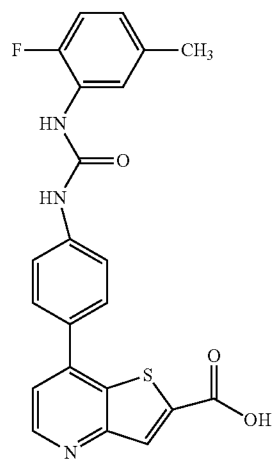 [SMILES: Cc1ccc(F)c(NC(=O)Nc2ccc(-c3ccnc4cc(C(=O)O)sc34)cc2)c1] | 421 | 7-[4-({[(2-fluoro-5-methylphenyl)amino]carbonyl}amino)phenyl]thieno[3,2-b]pyridine-2-carboxylic acid |
| F6 | 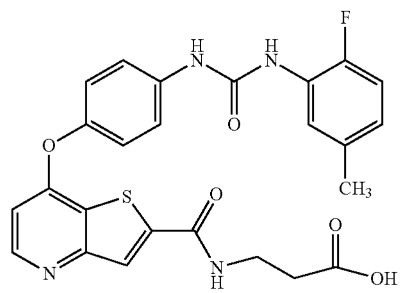 [SMILES: Cc1ccc(F)c(NC(=O)Nc2ccc(Oc3ccnc4cc(C(=O)NCCC(=O)O)sc34)cc2)c1] | 509 | 3-[({7-[4-({[(2-fluoro-5-methylphenyl)amino]carbonyl}amino)phenoxy]thieno[3,2-b]pyridin-2-yl}carbonyl)amino]propanoic acid |
| F7 | 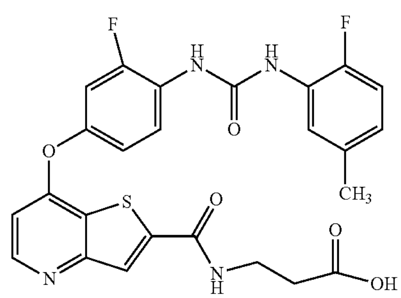 [SMILES: Cc1ccc(F)c(NC(=O)Nc2ccc(Oc3ccnc4cc(C(=O)NCCC(=O)O)sc34)cc2F)c1] | 527 | 3-[({7-[3-fluoro-4-({[(2-fluoro-5-methylphenyl)amino]carbonyl}amino)phenoxy]thieno[3,2-b]pyridin-2-yl}carbonyl)amino]propanoic acid |
| F8 | 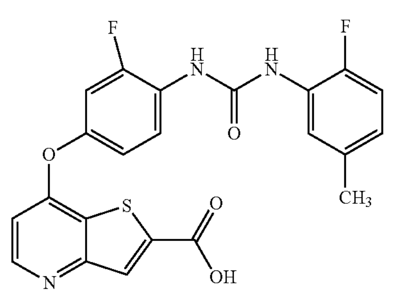 [SMILES: Cc1ccc(F)c(NC(=O)Nc2ccc(Oc3ccnc4cc(C(=O)O)sc34)cc2F)c1] | 455 | 7-[3-fluoro-4-({[(2-fluoro-5-methylphenyl)amino]carbonyl}amino)phenoxy]thieno[3,2-b]pyridine-2-carboxylic acid |

TABLE 1-continued

Exemplified Compounds of the Present Invention

| Compound | Structure | MW | Chemical Name |
|---|---|---|---|
| F9 | 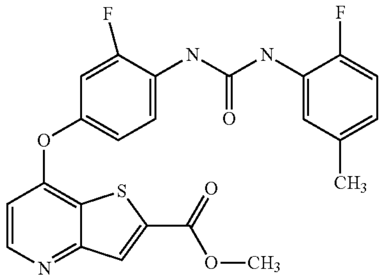 [SMILES: COC(=O)c1cc2nccc(Oc3ccc(NC(=O)Nc4cc(C)ccc4F)c(F)c3)c2s1] | 469 | methyl 7-(3-fluoro-4-(3-(2-fluoro-5-methylphenyl)ureido)phenoxy)thieno[3,2-b]pyridine-2-carboxylate |
| F10 | 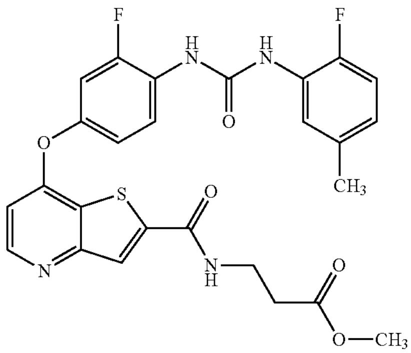 [SMILES: COC(=O)CCNC(=O)c1cc2nccc(Oc3ccc(NC(=O)Nc4cc(C)ccc4F)c(F)c3)c2s1] | 541 | methyl 3-[({7-[3-fluoro-4-({[(2-fluoro-5-methylphenyl)amino]carbonyl}amino)phenoxy]thieno[3,2-b]pyridin-2-yl}carbonyl)amino]propanoate |
| F11 | 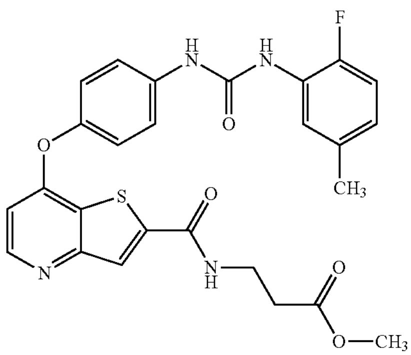 [SMILES: COC(=O)CCNC(=O)c1cc2nccc(Oc3ccc(NC(=O)Nc4cc(C)ccc4F)cc3)c2s1] | 523 | methyl 3-[({7-[4-({[(2-fluoro-5-methylphenyl)amino]carbonyl}amino)phenoxy]thieno[3,2-b]pyridin-2-yl}carbonyl)amino]propanoate |

Additional compounds of the present invention are listed below.

| Example# | Chemical Structure | MW | Chemical Name |
|---|---|---|---|
| 12 | 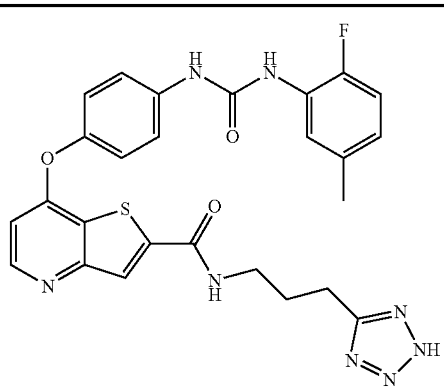 | 547 | 7-[4-({[(2-fluoro-5-methylphenyl)amino]carbonyl}amino)phenoxy]-N-[3-(2H-tetrazol-5-yl)propyl]thieno[3,2-b]pyridine-2-carboxamide |

| Example# | Chemical Structure | MW | Chemical Name |
|---|---|---|---|
| 13 | 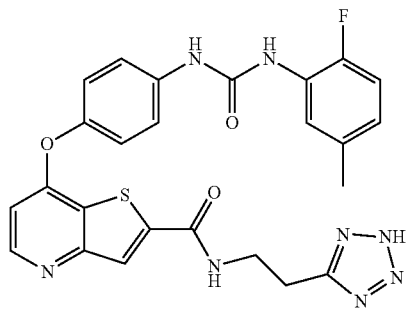 [SMILES: Cc1ccc(F)c(NC(=O)Nc2ccc(Oc3ccnc4cc(C(=O)NCCc5nn[nH]n5)sc34)cc2)c1] | 533 | 7-[4-({[(2-fluoro-5-methylphenyl)amino]carbonyl}amino)phenoxy]-N-[2-(2H-tetrazol-5-yl)ethyl]thieno[3,2-b]pyridine-2-carboxamide |
| 14 | 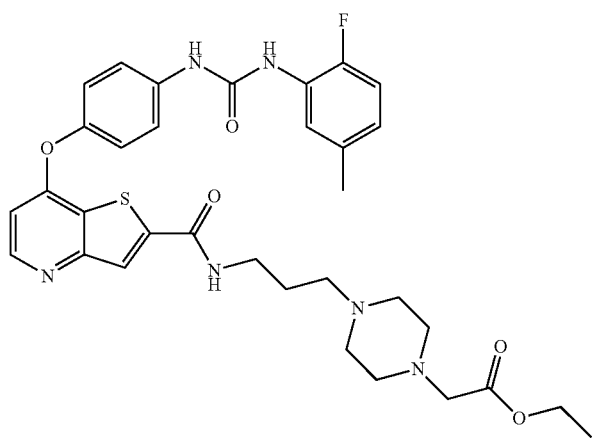 [SMILES: CCOC(=O)CN1CCN(CCCNC(=O)c2cc3nccc(Oc4ccc(NC(=O)Nc5cc(C)ccc5F)cc4)c3s2)CC1] | 649 | ethyl (4-{3-[({7-[4-({[(2-fluoro-5-methylphenyl)amino]carbonyl}amino)phenoxy]thieno[3,2-b]pyridin-2-yl}carbonyl)amino]propyl}piperazin-1-yl)acetate |
| 15 | 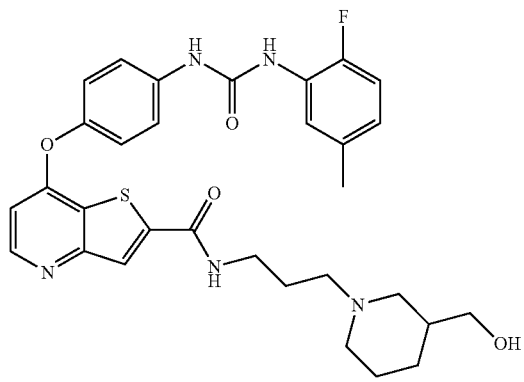 [SMILES: Cc1ccc(F)c(NC(=O)Nc2ccc(Oc3ccnc4cc(C(=O)NCCCN5CCCC(CO)C5)sc34)cc2)c1] | 592 | 7-[4-({[(2-fluoro-5-methylphenyl)amino]carbonyl}amino)phenoxy]-N-{3-[3-(hydroxymethyl)piperidin-1-yl]propyl}thieno[3,2-b]pyridine-2-carboxamide |
| 16 | 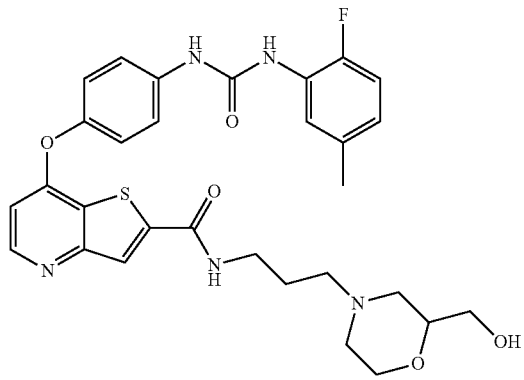 | 594 | 7-[4-({[(2-fluoro-5-methylphenyl)amino]carbonyl}amino)phenoxy]-N-{3-[2-(hydroxymethyl)morpholin-4-yl]propyl}thieno[3,2-b]pyridine-2-carboxamide |

-continued

| Example# | Chemical Structure | MW | Chemical Name |
|---|---|---|---|
| 17 | 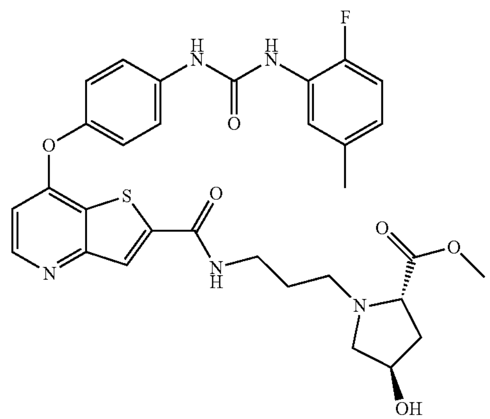 [SMILES: COC(=O)[C@@H]1C[C@@H](O)CN1CCCNC(=O)c1cc2nccc(Oc3ccc(NC(=O)Nc4cc(C)ccc4F)cc3)c2s1] | 622 | methyl rel-(2R,4S)-1-{3-[({7-[4-({[(2-fluoro-5-methylphenyl)amino]carbonyl}amino)phenoxy]thieno[3,2-b]pyridin-2-yl}carbonyl)amino]propyl}-4-hydroxypyrrolidine-2-carboxylate |
| 18 | 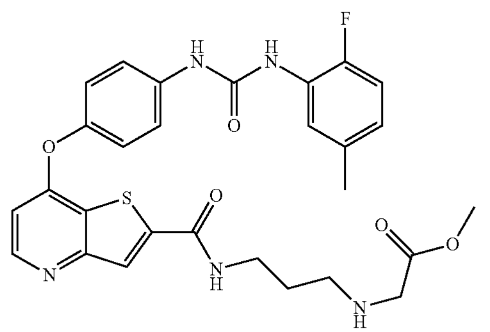 [SMILES: COC(=O)CNCCCNC(=O)c1cc2nccc(Oc3ccc(NC(=O)Nc4cc(C)ccc4F)cc3)c2s1] | 556 | methyl ({3-[({7-[4-({[(2-fluoro-5-methylphenyl)amino]carbonyl}amino)phenoxy]thieno[3,2-b]pyridin-2-yl}carbonyl)amino]propyl}amino)acetate |
| 19 | 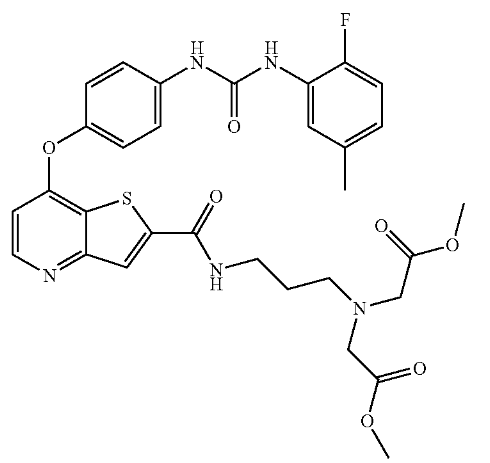 [SMILES: COC(=O)CN(CCCNC(=O)c1cc2nccc(Oc3ccc(NC(=O)Nc4cc(C)ccc4F)cc3)c2s1)CC(=O)OC] | 566 | dimethyl 2,2'-({3-[({7-[4-({[(2-fluoro-5-methylphenyl)amino]carbonyl}amino)phenoxy]thieno[3,2-b]pyridin-2-yl}carbonyl)amino]propyl}imino)diacetate |
| 20 | 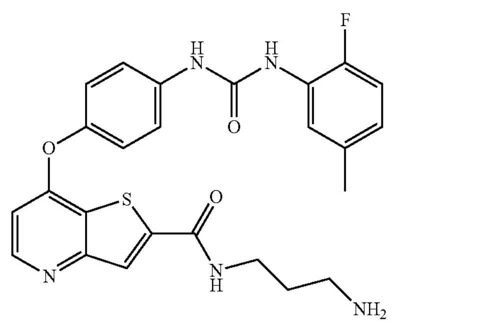 [SMILES: Cc1ccc(F)c(NC(=O)Nc2ccc(Oc3ccnc4cc(C(=O)NCCCN)sc34)cc2)c1] | 638 | N-(3-aminopropyl)-7-[4-({[(2-fluoro-5-methylphenyl)amino]carbonyl}amino)phenoxy]thieno[3,2-b]pyridine-2-carboxamide |

| Example# | Chemical Structure | MW | Chemical Name |
|---|---|---|---|
| 21 | 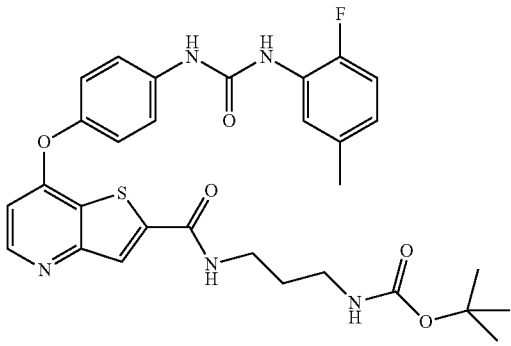 [SMILES: Cc1ccc(F)c(NC(=O)Nc2ccc(Oc3ccnc4cc(C(=O)NCCCNC(=O)OC(C)(C)C)sc34)cc2)c1] | 494 | tert-butyl {3-[({7-[4-({[(2-fluoro-5-methylphenyl)amino]carbonyl}amino)phenoxy]thieno[3,2-b]pyridin-2-yl}carbonyl)amino]propyl}carbamate |
| 21A | 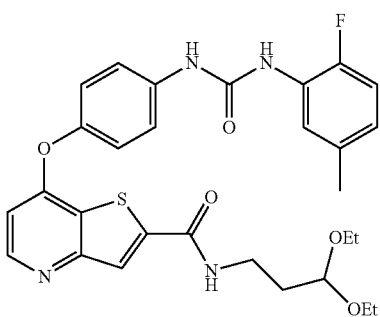 [SMILES: CCOC(CCNC(=O)c1cc2nccc(Oc3ccc(NC(=O)Nc4cc(C)ccc4F)cc3)c2s1)OCC] | 594 | N-(3,3-diethoxypropyl)-7-[4-({[(2-fluoro-5-methylphenyl)amino]carbonyl}amino)phenoxy]thieno[3,2-b]pyridine-2-carboxamide |
| 22 | 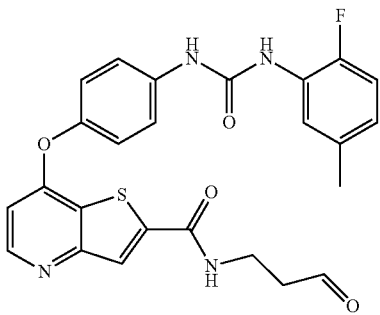 [SMILES: Cc1ccc(F)c(NC(=O)Nc2ccc(Oc3ccnc4cc(C(=O)NCCC=O)sc34)cc2)c1] | 493 | 7-[4-({[(2-fluoro-5-methylphenyl)amino]carbonyl}amino)phenoxy]-N-(3-oxopropyl)thieno[3,2-b]pyridine-2-carboxamide |
| 23 | 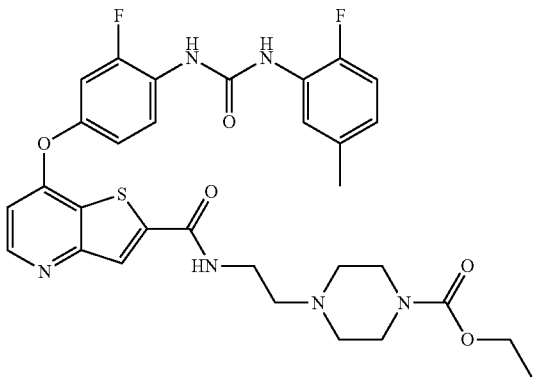 [SMILES: CCOC(=O)N1CCN(CCNC(=O)c2cc3nccc(Oc4ccc(NC(=O)Nc5cc(C)ccc5F)c(F)c4)c3s2)CC1] | 639 | ethyl 4-{2-[({7-[3-fluoro-4-({[(2-fluoro-5-methylphenyl)amino]carbonyl}amino)phenoxy]thieno[3,2-b]pyridin-2-yl}carbonyl)amino]ethyl}piperazine-1-carboxylate |

-continued

| Example# | Chemical Structure | MW | Chemical Name |
|---|---|---|---|
| 24 | 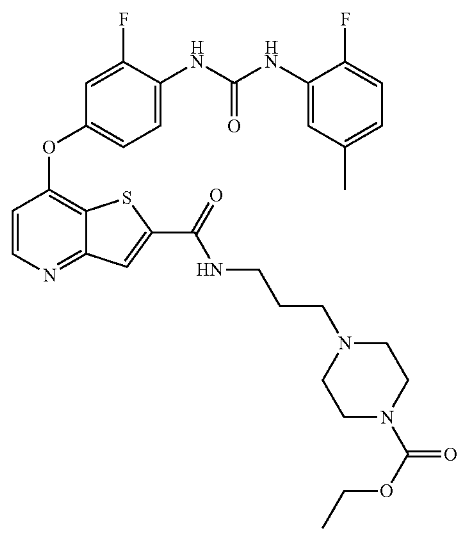 [SMILES: CCOC(=O)N1CCN(CCCNC(=O)c2cc3nccc(Oc4ccc(NC(=O)Nc5cc(C)ccc5F)c(F)c4)c3s2)CC1] | 653 | ethyl 4-{3-[({7-[3-fluoro-4-({[(2-fluoro-5-methylphenyl)amino]carbonyl}amino)phenoxy]thieno[3,2-b]pyridin-2-yl}carbonyl)amino]propyl}piperazine-1-carboxylate |
| 25 | 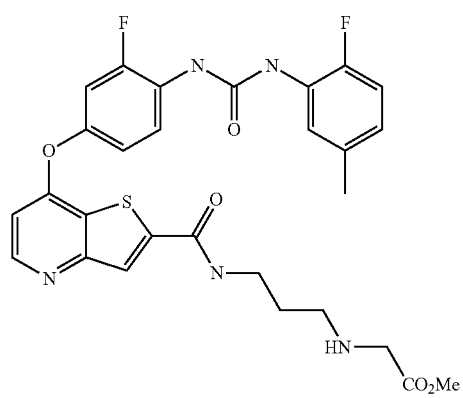 [SMILES: COC(=O)CNCCCNC(=O)c1cc2nccc(Oc3ccc(NC(=O)Nc4cc(C)ccc4F)c(F)c3)c2s1] | 584 | methyl ({3-[({7-[3-fluoro-4-({[(2-fluoro-5-methylphenyl)amino]carbonyl}amino)phenoxy]thieno[3,2-b]pyridin-2-yl}carbonyl)amino]propyl}amino)acetate |
| 26 | 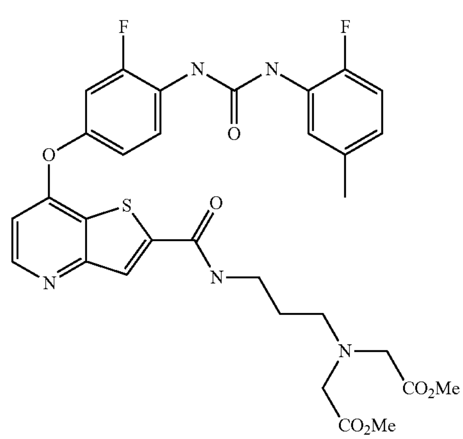 [SMILES: COC(=O)CN(CCCNC(=O)c1cc2nccc(Oc3ccc(NC(=O)Nc4cc(C)ccc4F)c(F)c3)c2s1)CC(=O)OC] | 656 | dimethyl 2,2'-({3-[({7-[3-fluoro-4-({[(2-fluoro-5-methylphenyl)amino]carbonyl}amino)phenoxy]thieno[3,2-b]pyridin-2-yl}carbonyl)amino]propyl}imino)diacetate |

| Example# | Chemical Structure | MW | Chemical Name |
|---|---|---|---|
| 27 | 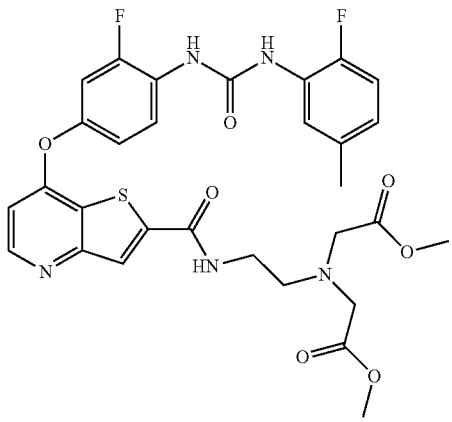 [SMILES: COC(=O)CN(CCNC(=O)c1cc2nccc(Oc3ccc(NC(=O)Nc4cc(C)ccc4F)c(F)c3)c2s1)CC(=O)OC] | 642 | dimethyl 2,2'-({2-[({7-[3-fluoro-4-({[(2-fluoro-5-methylphenyl)amino]carbonyl}amino)phenoxy]thieno[3,2-b]pyridin-2-yl}carbonyl)amino]ethyl}imino)diacetate |
| 28 | 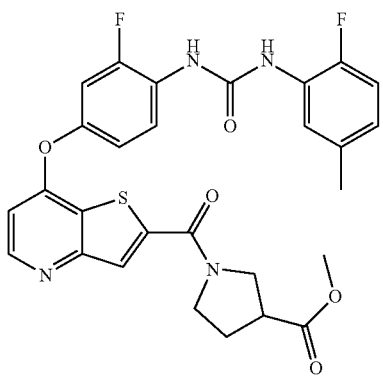 [SMILES: COC(=O)C1CCN(C(=O)c2cc3nccc(Oc4ccc(NC(=O)Nc5cc(C)ccc5F)c(F)c4)c3s2)C1] | 567 | methyl 1-({7-[3-fluoro-4-({[(2-fluoro-5-methylphenyl)amino]carbonyl}amino)phenoxy]thieno[3,2-b]pyridin-2-yl}carbonyl)pyrrolidine-3-carboxylate |
| 29 | 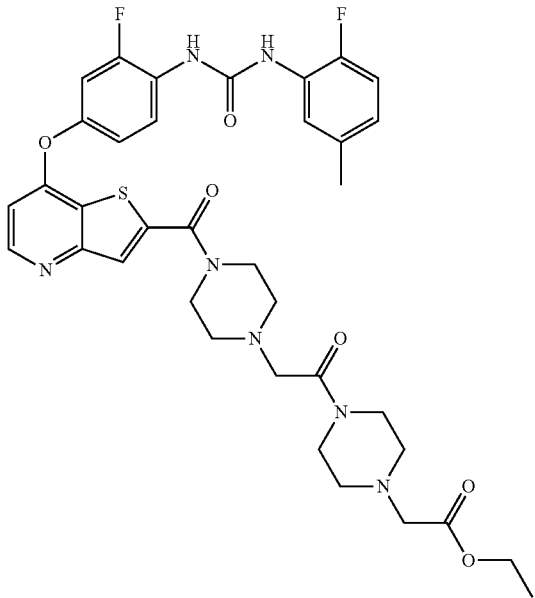 [SMILES: CCOC(=O)CN1CCN(C(=O)CN2CCN(C(=O)c3cc4nccc(Oc5ccc(NC(=O)Nc6cc(C)ccc6F)c(F)c5)c4s3)CC2)CC1] | 736 | ethyl (4-{[4-({7-[3-fluoro-4-({[(2-fluoro-5-methylphenyl)amino]carbonyl}amino)phenoxy]thieno[3,2-b]pyridin-2-yl}carbonyl)piperazin-1-yl]acetyl}piperazin-1-yl)acetate |

| Example# | Chemical Structure | MW | Chemical Name |
|---|---|---|---|
| 30 | 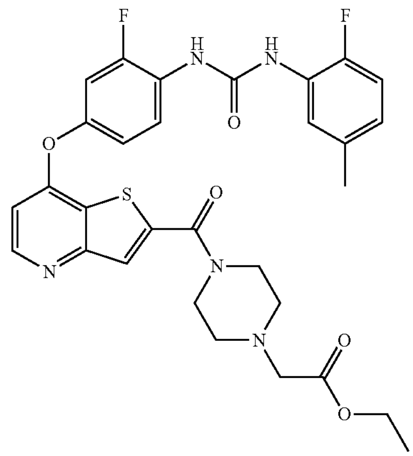 [SMILES: CCOC(=O)CN1CCN(C(=O)c2cc3nccc(Oc4ccc(NC(=O)Nc5cc(C)ccc5F)c(F)c4)c3s2)CC1] | 610 | ethyl [4-({7-[3-fluoro-4-({[(2-fluoro-5-methylphenyl)amino]carbonyl}amino)phenoxy]thieno[3,2-b]pyridin-2-yl}carbonyl)piperazin-1-yl]acetate |
| 31 | 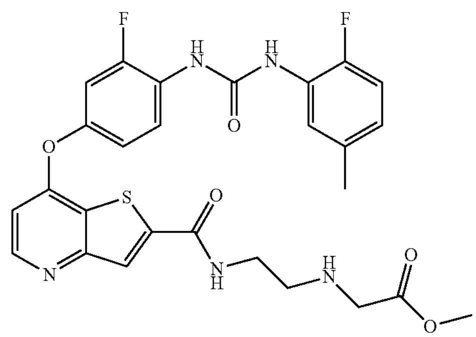 [SMILES: COC(=O)CNCCNC(=O)c1cc2nccc(Oc3ccc(NC(=O)Nc4cc(C)ccc4F)c(F)c3)c2s1] | 570 | methyl ({2-[({7-[3-fluoro-4-({[(2-fluoro-5-methylphenyl)amino]carbonyl}amino)phenoxy]thieno[3,2-b]pyridin-2-yl}carbonyl)amino]ethyl}amino)acetate |
| 32 | 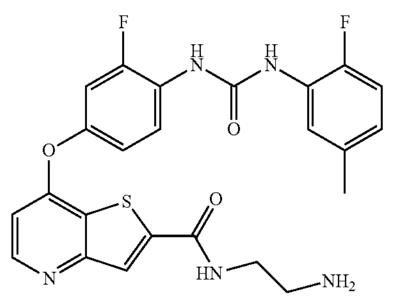 [SMILES: Cc1ccc(F)c(NC(=O)Nc2ccc(Oc3ccnc4cc(C(=O)NCCN)sc34)cc2F)c1] | 498 | N-(2-aminoethyl)-7-[3-fluoro-4-({[(2-fluoro-5-methylphenyl)amino]carbonyl}amino)phenoxy]thieno[3,2-b]pyridine-2-carboxamide |
| 33 | 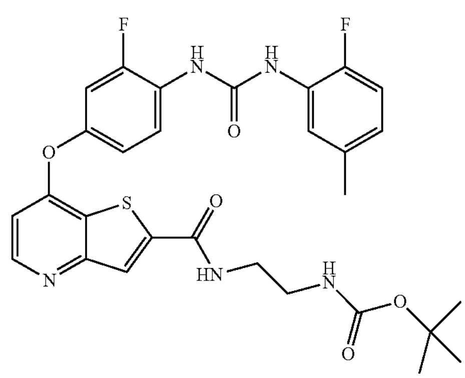 [SMILES: Cc1ccc(F)c(NC(=O)Nc2ccc(Oc3ccnc4cc(C(=O)NCCNC(=O)OC(C)(C)C)sc34)cc2F)c1] | 598 | tert-butyl {2-[({7-[3-fluoro-4-({[(2-fluoro-5-methylphenyl)amino]carbonyl}amino)phenoxy]thieno[3,2-b]pyridin-2-yl}carbonyl)amino]ethyl}carbamate |

| Example# | Chemical Structure | MW | Chemical Name |
|---|---|---|---|
| 34 | 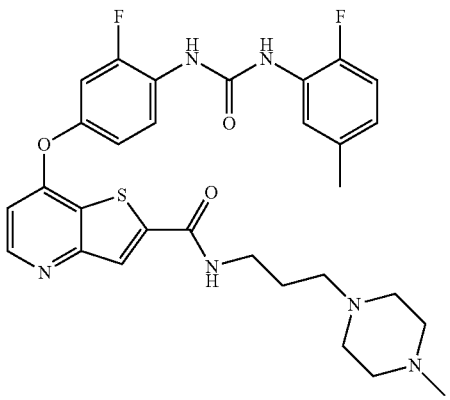 [SMILES: Cc1ccc(F)c(NC(=O)Nc2ccc(Oc3ccnc4cc(C(=O)NCCCN5CCN(C)CC5)sc34)cc2F)c1] | 595 | 7-[3-fluoro-4-({[(2-fluoro-5-methylphenyl)amino]carbonyl}amino)phenoxy]-N-[3-(4-methylpiperazin-1-yl)propyl]thieno[3,2-b]pyridine-2-carboxamide |
| 35 | 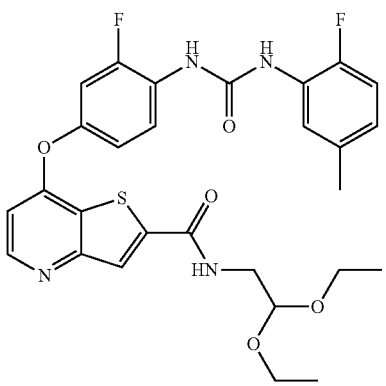 [SMILES: CCOC(CNC(=O)c1cc2nccc(Oc3ccc(NC(=O)Nc4cc(C)ccc4F)c(F)c3)c2s1)OCC] | 571 | N-(2,2-diethoxyethyl)-7-[3-fluoro-4-({[(2-fluoro-5-methylphenyl)amino]carbonyl}amino)phenoxy]thieno[3,2-b]pyridine-2-carboxamide |
| 36 | 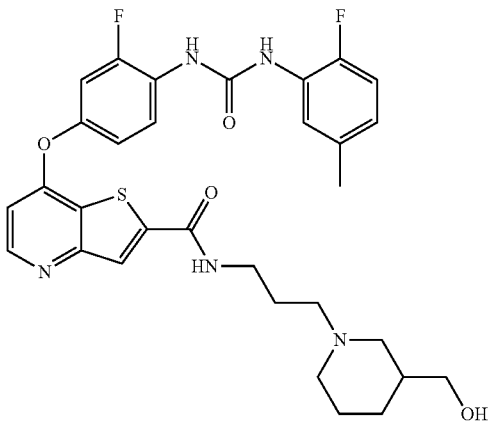 | 610 | 7-[3-fluoro-4-({[(2-fluoro-5-methylphenyl)amino]carbonyl}amino)phenoxy]-N-{3-[3-(hydroxymethyl)piperidin-1-yl]propyl}thieno[3,2-b]pyridine-2-carboxamide |

-continued

| Example# | Chemical Structure | MW | Chemical Name |
|---|---|---|---|
| 37 | 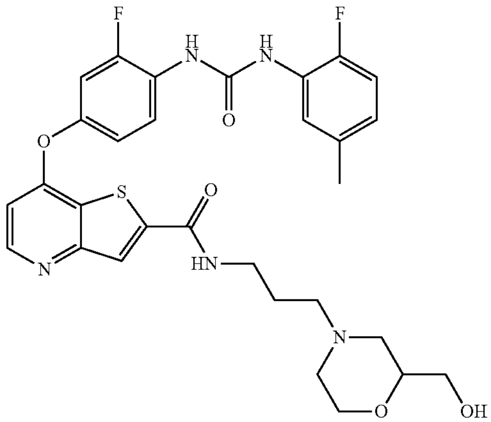 [SMILES: Cc1ccc(F)c(NC(=O)Nc2ccc(Oc3ccnc4cc(C(=O)NCCCN5CCOC(CO)C5)sc34)cc2F)c1] | 612 | 7-[3-fluoro-4-({[(2-fluoro-5-methylphenyl)amino]carbonyl}amino)phenoxy]-N-{3-[2-(hydroxymethyl)morpholin-4-yl]propyl}thieno[3,2-b]pyridine-2-carboxamide |
| 38 | 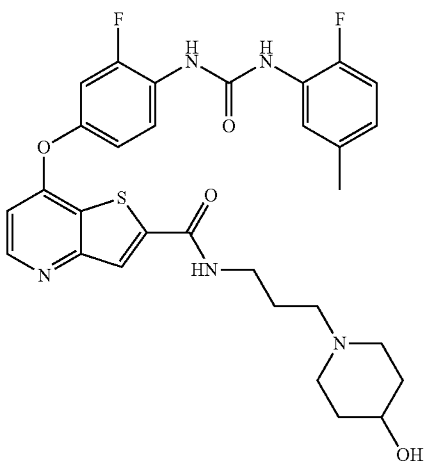 [SMILES: Cc1ccc(F)c(NC(=O)Nc2ccc(Oc3ccnc4cc(C(=O)NCCCN5CCC(O)CC5)sc34)cc2F)c1] | 596 | 7-[3-fluoro-4-({[(2-fluoro-5-methylphenyl)amino]carbonyl}amino)phenoxy]-N-[3-(4-hydroxypiperidin-1-yl)propyl]thieno[3,2-b]pyridine-2-carboxamide |
| 39 | 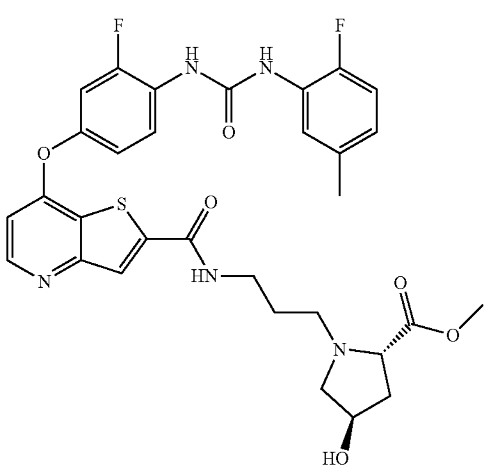 [SMILES: COC(=O)[C@@H]1C[C@@H](O)CN1CCCNC(=O)c1cc2nccc(Oc3ccc(NC(=O)Nc4cc(C)ccc4F)c(F)c3)c2s1] | 640 | methyl (2S,4R)-1-{3-[({7-[3-fluoro-4-({[(2-fluoro-5-methylphenyl)amino]carbonyl}amino)phenoxy]thieno[3,2-b]pyridin-2-yl}carbonyl)amino]propyl}-4-hydroxypyrrolidine-2-carboxylate |

-continued

| Example# | Chemical Structure | MW | Chemical Name |
|---|---|---|---|
| 40 | 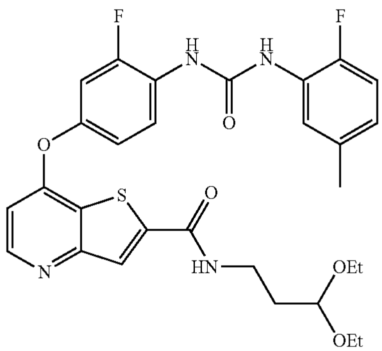 [SMILES: CCOC(CCNC(=O)c1cc2nccc(Oc3ccc(NC(=O)Nc4cc(C)ccc4F)c(F)c3)c2s1)OCC] | 585 | N-(3,3-diethoxypropyl)-7-[3-fluoro-4-({[(2-fluoro-5-methylphenyl)amino]carbonyl}amino)phenoxy]thieno[3,2-b]pyridine-2-carboxamide |
| 41 | 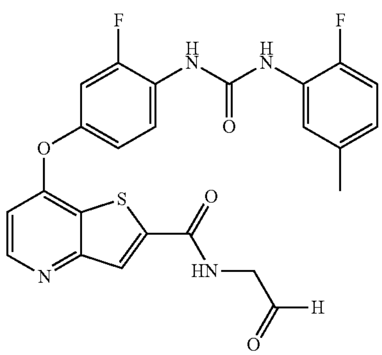 [SMILES: Cc1ccc(F)c(NC(=O)Nc2ccc(Oc3ccnc4cc(C(=O)NCC=O)sc34)cc2F)c1] | 496 | 7-[3-fluoro-4-({[(2-fluoro-5-methylphenyl)amino]carbonyl}amino)phenoxy]-N-(2-oxoethyl)thieno[3,2-b]pyridine-2-carboxamide |
| 42 | 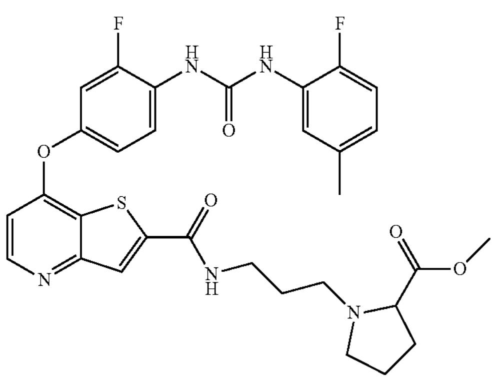 [SMILES: COC(=O)C1CCCN1CCCNC(=O)c1cc2nccc(Oc3ccc(NC(=O)Nc4cc(C)ccc4F)c(F)c3)c2s1] | 624 | methyl 1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-2-carboxylate |
| 43 | 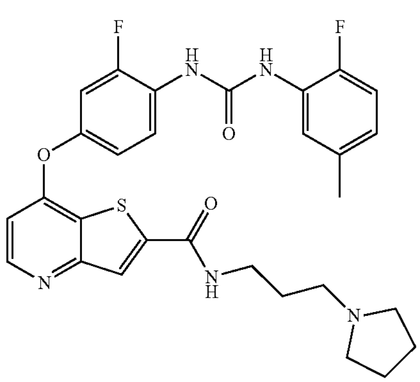 [SMILES: Cc1ccc(F)c(NC(=O)Nc2ccc(Oc3ccnc4cc(C(=O)NCCCN5CCCC5)sc34)cc2F)c1] | 566 | 7-[3-fluoro-4-({[(2-fluoro-5-methylphenyl)amino]carbonyl}amino)phenoxy]-N-(3-pyrrolidin-1-ylpropyl)thieno[3,2-b]pyridine-2-carboxamide |

| Example# | Chemical Structure | MW | Chemical Name |
|---|---|---|---|
| 44 | 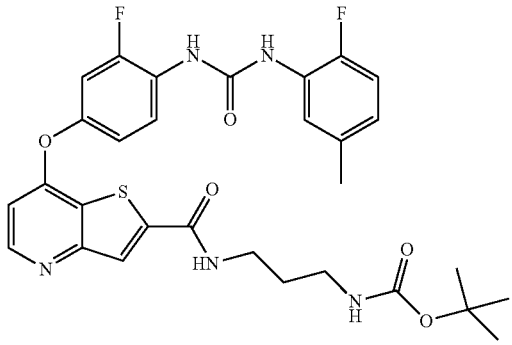 [SMILES: Cc1ccc(F)c(NC(=O)Nc2ccc(Oc3ccnc4cc(C(=O)NCCCNC(=O)OC(C)(C)C)sc34)cc2F)c1] | 612 | tert-butyl {3-[({7-[3-fluoro-4-({[(2-fluoro-5-methylphenyl)amino]carbonyl}amino)phenoxy]thieno[3,2-b]pyridin-2-yl}carbonyl)amino]propyl}carbamate |
| 45 | 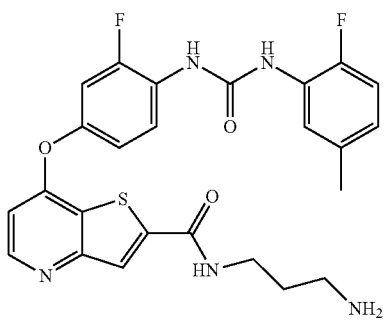 [SMILES: Cc1ccc(F)c(NC(=O)Nc2ccc(Oc3ccnc4cc(C(=O)NCCCN)sc34)cc2F)c1] | 512 | N-(3-aminopropyl)-7-[3-fluoro-4-({[(2-fluoro-5-methylphenyl)amino]carbonyl}amino)phenoxy]thieno[3,2-b]pyridine-2-carboxamide |
| 46 | 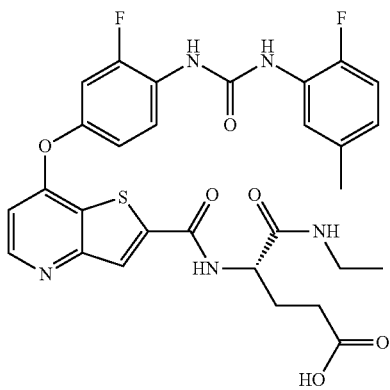 [SMILES: CCNC(=O)[C@H](CCC(=O)O)NC(=O)c1cc2nccc(Oc3ccc(NC(=O)Nc4cc(C)ccc4F)c(F)c3)c2s1] | 612 | (4S)-5-(ethylamino)-4-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoic acid |
| 47 | 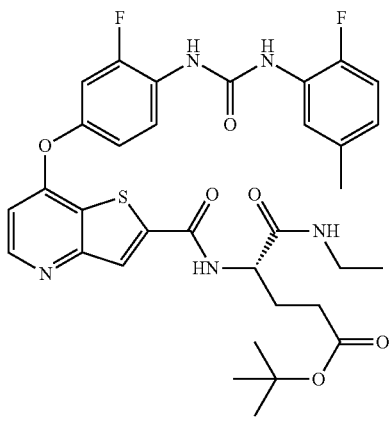 [SMILES: CCNC(=O)[C@H](CCC(=O)OC(C)(C)C)NC(=O)c1cc2nccc(Oc3ccc(NC(=O)Nc4cc(C)ccc4F)c(F)c3)c2s1] | 668 | tert-butyl (4S)-5-(ethylamino)-4-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoate |

-continued

| Example# | Chemical Structure | MW | Chemical Name |
|---|---|---|---|
| 48 | 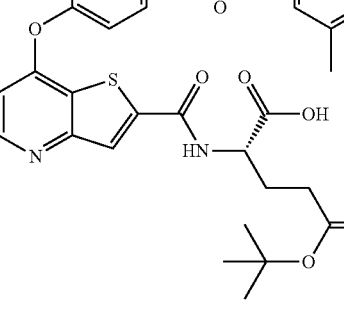 | 641 | (2S)-5-tert-butoxy-2-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoic acid |
| 49 | 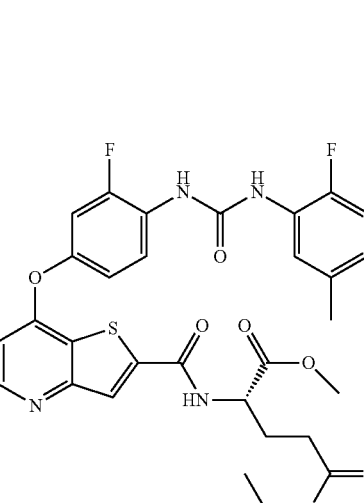 | 655 | 5-tert-butyl 1-methyl (2S)-2-[({7-[3-fluoro-4-({[(2-fluoro-5-methylphenyl)amino]carbonyl}amino)phenoxy]thieno[3,2-b]pyridin-2-yl}carbonyl)amino]pentanedioate |
| 50 | 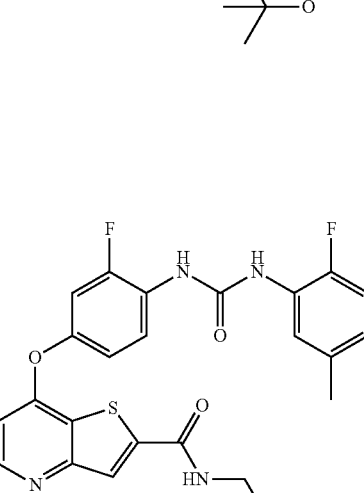 | 610 | 1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-3-carboxylic acid |

-continued

| Example# | Chemical Structure | MW | Chemical Name |
|---|---|---|---|
| 51 | 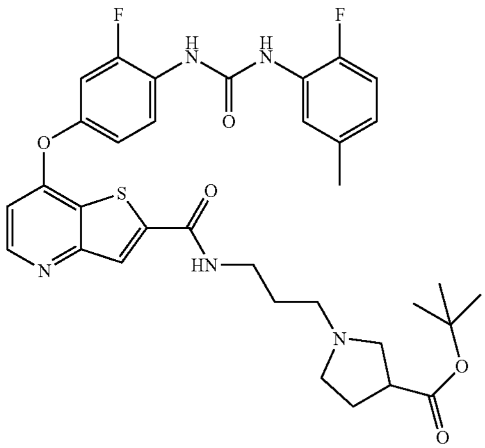 [SMILES: Cc1ccc(F)c(NC(=O)Nc2ccc(Oc3ccnc4cc(C(=O)NCCCN5CCC(C(=O)OC(C)(C)C)C5)sc34)cc2F)c1] | 666 | tert-butyl 1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-3-carboxylate |
| 52 | 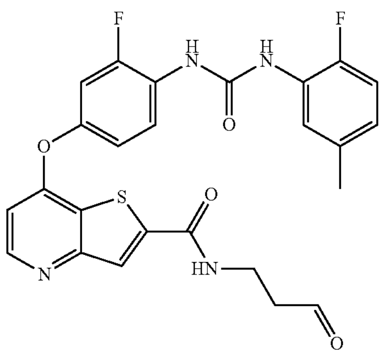 [SMILES: Cc1ccc(F)c(NC(=O)Nc2ccc(Oc3ccnc4cc(C(=O)NCCC=O)sc34)cc2F)c1] | 511 | 7-[3-fluoro-4-({[(2-fluoro-5-methylphenyl)amino]carbonyl}amino)phenoxy]-N-(3-oxopropyl)thieno[3,2-b]pyridine-2-carboxamide |
| 53 | 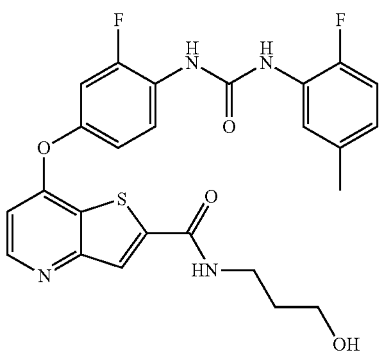 [SMILES: Cc1ccc(F)c(NC(=O)Nc2ccc(Oc3ccnc4cc(C(=O)NCCCO)sc34)cc2F)c1] | 513 | 7-[3-fluoro-4-({[(2-fluoro-5-methylphenyl)amino]carbonyl}amino)phenoxy]-N-(3-hydroxypropyl)thieno[3,2-b]pyridine-2-carboxamide |
| 54 | 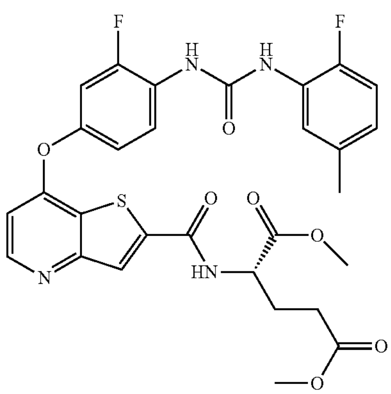 [SMILES: COC(=O)CC[C@H](NC(=O)c1cc2nccc(Oc3ccc(NC(=O)Nc4cc(C)ccc4F)c(F)c3)c2s1)C(=O)OC] | 613 | dimethyl (2S)-2-[({7-[3-fluoro-4-({[(2-fluoro-5-methylphenyl)amino]carbonyl}amino)phenoxy]thieno[3,2-b]pyridin-2-yl}carbonyl)amino]pentanedioate |

-continued

| Example# | Chemical Structure | MW | Chemical Name |
|---|---|---|---|
| 55 | 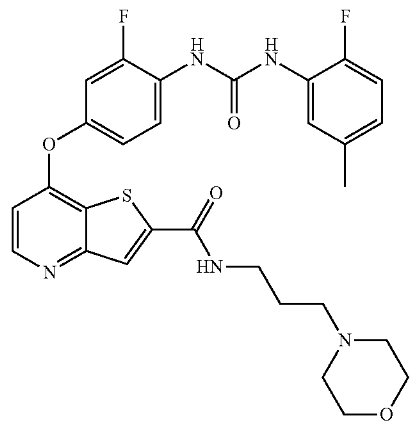 [SMILES: Cc1ccc(F)c(NC(=O)Nc2ccc(Oc3ccnc4cc(C(=O)NCCCN5CCOCC5)sc34)cc2F)c1] | 582 | 7-[3-fluoro-4-({[(2-fluoro-5-methylphenyl)amino]carbonyl}amino)phenoxy]-N-(3-morpholin-4-ylpropyl)thieno[3,2-b]pyridine-2-carboxamide |
| 56 | 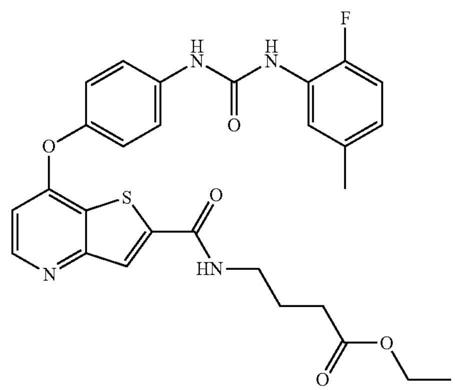 [SMILES: CCOC(=O)CCCNC(=O)c1cc2nccc(Oc3ccc(NC(=O)Nc4cc(C)ccc4F)cc3)c2s1] | 551 | ethyl 4-[({7-[4-({[(2-fluoro-5-methylphenyl)amino]carbonyl}amino)phenoxy]thieno[3,2-b]pyridin-2-yl}carbonyl)amino]butanoate |
| 57 | 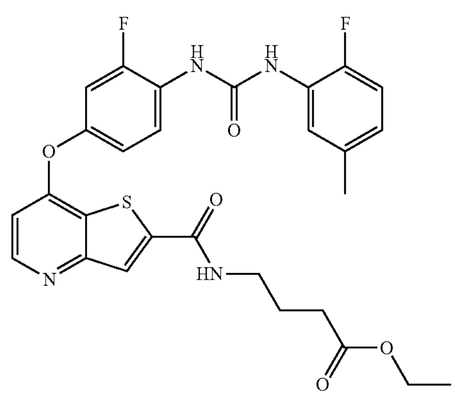 [SMILES: CCOC(=O)CCCNC(=O)c1cc2nccc(Oc3ccc(NC(=O)Nc4cc(C)ccc4F)c(F)c3)c2s1] | 569 | ethyl 4-[({7-[3-fluoro-4-({[(2-fluoro-5-methylphenyl)amino]carbonyl}amino)phenoxy]thieno[3,2-b]pyridin-2-yl}carbonyl)amino]butanoate |
| 58 | 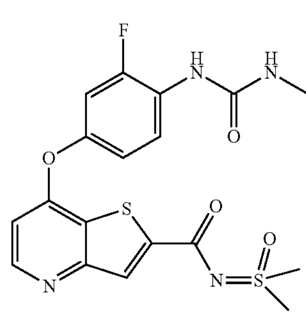 | 531 | N-[dimethyl)oxido)-λ-4-sulfanylidene]-7-[3-fluoro-4-({[(2-fluoro-5-methylphenyl)amino]carbonyl}amino)phenoxy]thieno[3,2-b]pyridine-2-carboxamide |

-continued

| Example# | Chemical Structure | MW | Chemical Name |
|---|---|---|---|
| 59 | 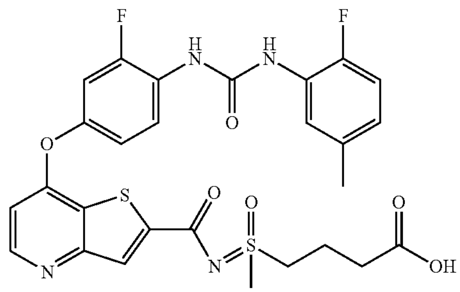 [SMILES: Cc1ccc(F)c(NC(=O)Nc2ccc(Oc3ccnc4cc(C(=O)N=S(C)(=O)CCCC(=O)O)sc34)cc2F)c1] | 603 | 4-[N-({7-[3-fluoro-4-({[(2-fluoro-5-methylphenyl)amino]carbonyl}amino)phenoxy]thieno[3,2-b]pyridin-2-yl}carbonyl)-S-methylsulfonimidoyl]butanoic acid |
| 60 | 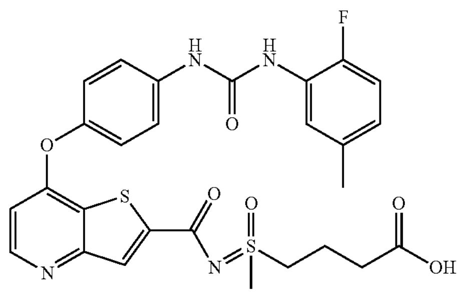 [SMILES: Cc1ccc(F)c(NC(=O)Nc2ccc(Oc3ccnc4cc(C(=O)N=S(C)(=O)CCCC(=O)O)sc34)cc2)c1] | 585 | 4-[N-({7-[4-({[(2-fluoro-5-methylphenyl)amino]carbonyl}amino)phenoxy]thieno[3,2-b]pyridin-2-yl}carbonyl)-S-methylsulfonimidoyl]butanoic acid |
| 61 | 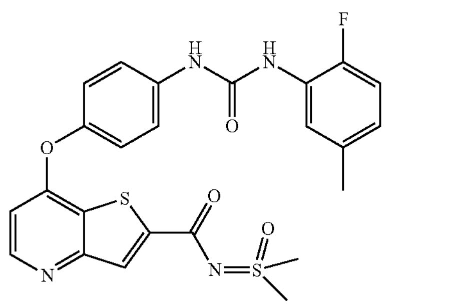 [SMILES: Cc1ccc(F)c(NC(=O)Nc2ccc(Oc3ccnc4cc(C(=O)N=S(C)(C)=O)sc34)cc2)c1] | 513 | N-[dimethyl(oxido)-lambda~4~-sulfanylidene]-7-[4-({[(2-fluoro-5-methylphenyl)amino]carbonyl}amino)phenoxy]thieno[3,2-b]pyridine-2-carboxamide |
| 62 | 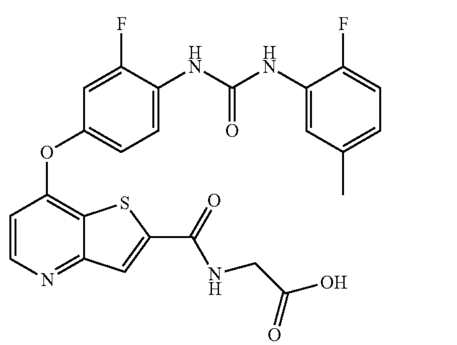 [SMILES: Cc1ccc(F)c(NC(=O)Nc2ccc(Oc3ccnc4cc(C(=O)NCC(=O)O)sc34)cc2F)c1] | 512 | [({7-[3-fluoro-4-({[(2-fluoro-5-methylphenyl)amino]carbonyl}amino)phenoxy]thieno[3,2-b]pyridin-2-yl}carbonyl)amino]acetic acid |
| 63 | 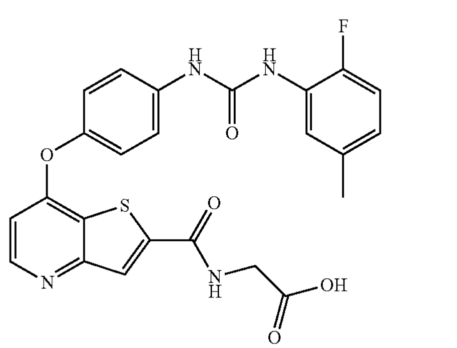 [SMILES: Cc1ccc(F)c(NC(=O)Nc2ccc(Oc3ccnc4cc(C(=O)NCC(=O)O)sc34)cc2)c1] | 495 | [({7-[4-({[(2-fluoro-5-methylphenyl)amino]carbonyl}amino)phenoxy]thieno[3,2-b]pyridin-2-yl}carbonyl)amino]acetic acid |

-continued

| Example# | Chemical Structure | MW | Chemical Name |
|---|---|---|---|
| 64 | 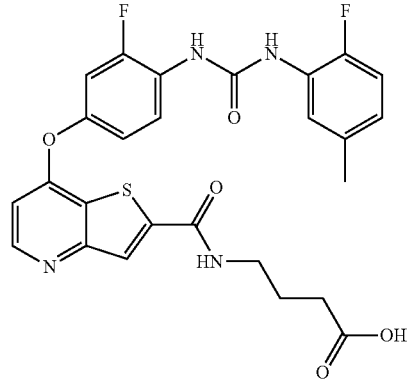 [SMILES: Cc1ccc(F)c(NC(=O)Nc2ccc(Oc3ccnc4cc(C(=O)NCCCC(=O)O)sc34)cc2F)c1] | 541 | 4-[({7-[3-fluoro-4-({[(2-fluoro-5-methylphenyl)amino]carbonyl}amino)phenoxy]thieno[3,2-b]pyridin-2-yl}carbonyl)amino]butanoic acid |
| 65 | 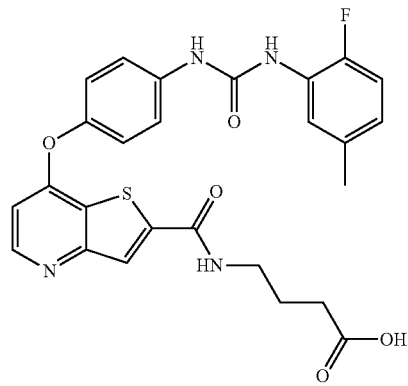 [SMILES: Cc1ccc(F)c(NC(=O)Nc2ccc(Oc3ccnc4cc(C(=O)NCCCC(=O)O)sc34)cc2)c1] | 523 | 4-[({7-[4-({[(2-fluoro-5-methylphenyl)amino]carbonyl}amino)phenoxy]thieno[3,2-b]pyridin-2-yl}carbonyl)amino]butanoic acid |
| 66 | 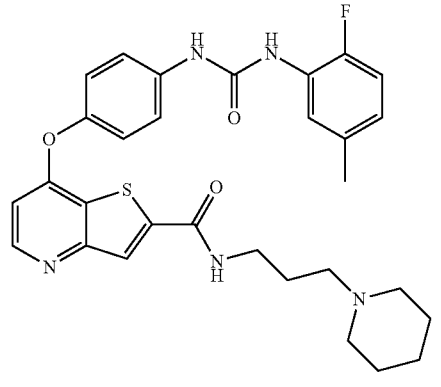 [SMILES: Cc1ccc(F)c(NC(=O)Nc2ccc(Oc3ccnc4cc(C(=O)NCCCN5CCCCC5)sc34)cc2)c1] | 561 | 7-[4-({[(2-fluoro-5-methylphenyl)amino]carbonyl}amino)phenoxy]-N-(3-piperidin-1-ylpropyl)thieno[3,2-b]pyridine-2-carboxamide |
| 67 | 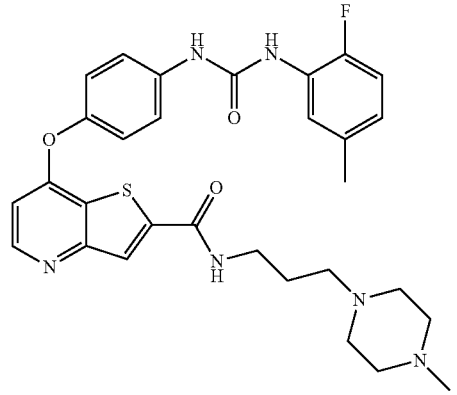 [SMILES: Cc1ccc(F)c(NC(=O)Nc2ccc(Oc3ccnc4cc(C(=O)NCCCN5CCN(C)CC5)sc34)cc2)c1] | 577 | 7-[4-({[(2-fluoro-5-methylphenyl)amino]carbonyl}amino)phenoxy]-N-[3-(4-methylpiperazin-1-yl)propyl]thieno[3,2-b]pyridine-2-carboxamide |

| Example# | Chemical Structure | MW | Chemical Name |
|---|---|---|---|
| 68 | 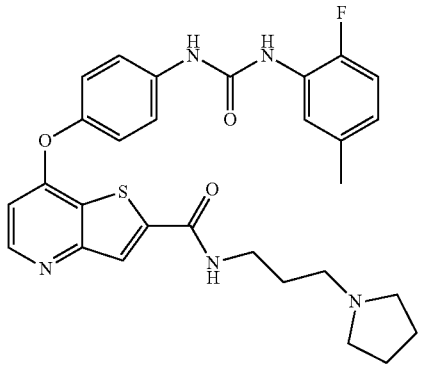 [SMILES: Cc1ccc(F)c(NC(=O)Nc2ccc(Oc3ccnc4cc(C(=O)NCCCN5CCCC5)sc34)cc2)c1] | 547 | 7-[4-({[(2-fluoro-5-methylphenyl)amino]carbonyl}amino)phenoxy]-N-(3-pyrrolidin-1-ylpropyl)thieno[3,2-b]pyridine-2-carboxamide |
| 69 | 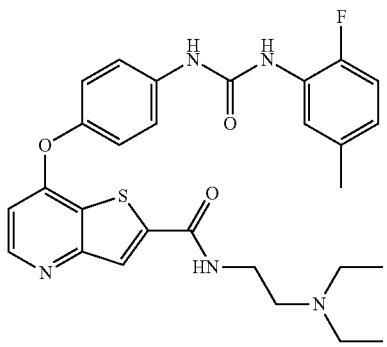 [SMILES: CCN(CC)CCNC(=O)c1cc2nccc(Oc3ccc(NC(=O)Nc4cc(C)ccc4F)cc3)c2s1] | 535 | N-[2-(diethylamino)ethyl]-7-[4-({[(2-fluoro-5-methylphenyl)amino]carbonyl}amino)phenoxy]thieno[3,2-b]pyridine-2-carboxamide |
| 70 | 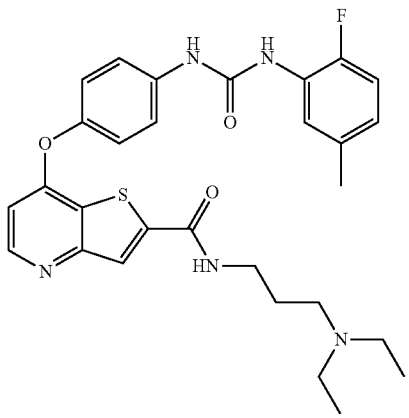 [SMILES: CCN(CC)CCCNC(=O)c1cc2nccc(Oc3ccc(NC(=O)Nc4cc(C)ccc4F)cc3)c2s1] | 549 | N-[3-(diethylamino)propyl]-7-[4-({[(2-fluoro-5-methylphenyl)amino]carbonyl}amino)phenoxy]thieno[3,2-b]pyridine-2-carboxamide |
| 71 | 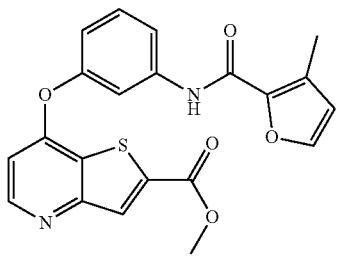 [SMILES: COC(=O)c1cc2nccc(Oc3cccc(NC(=O)c4occc4C)c3)c2s1] | 408 | Methyl 7-{3-[(3-methyl-2-furoyl)amino]phenoxy}thieno[3,2-b]pyridine-2-carboxylate |

-continued

| Example# | Chemical Structure | MW | Chemical Name |
|---|---|---|---|
| 72 | 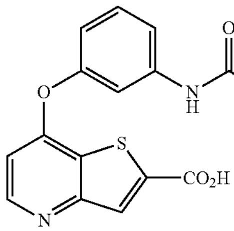 | 394 | 7-{3-[(3-methyl-2-furoyl)amino]phenoxy}thieno[3,2-b]pyridine-2-carboxylic acid |
| 73 | 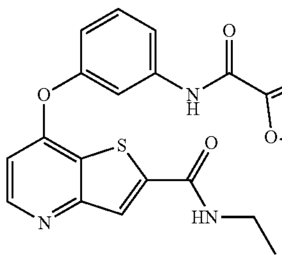 | 421 | N-ethyl-7-{3-[(3-methyl-2-furoyl)amino]phenoxy}thieno[3,2-b]pyridine-2-carboxamide |
| 74 | 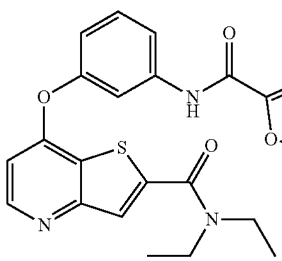 | 449 | N,N-diethyl-7-{3-[(3-methyl-2-furoyl)amino]phenoxy}thieno[3,2-b]pyridine-2-carboxamide |
| 75 | 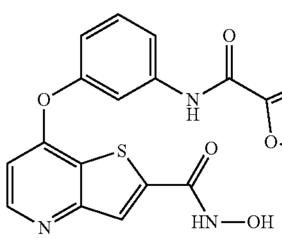 | 409 | N-hydroxy-7-{3-[(3-methyl-2-furoyl)amino]phenoxy}thieno[3,2-b]pyridine-2-carboxamide |
| 76 | 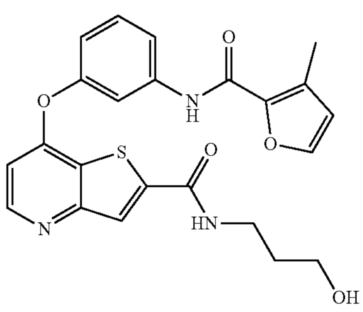 [SMILES: Cc1ccoc1C(=O)Nc1cccc(Oc2ccnc3cc(C(=O)NCCCO)sc23)c1] | 451 | N-(3-hydroxypropyl)-7-{3-[(3-methyl-2-furoyl)amino]phenoxy}thieno[3,2-b]pyridine-2-carboxamide |
| 77 | 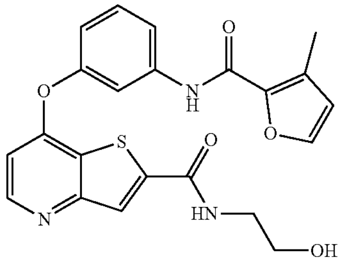 | 437 | N-(2-hydroxyethyl)-7-{3-[(3-methyl-2-furoyl)amino]phenoxy}thieno[3,2-b]pyridine-2-carboxamide |

| Example# | Chemical Structure | MW | Chemical Name |
|---|---|---|---|
| 78 | 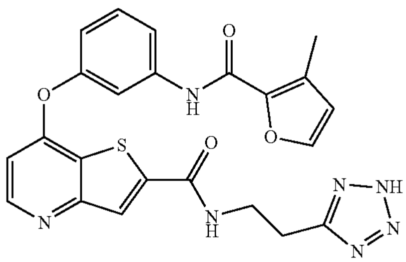 [SMILES: Cc1ccoc1C(=O)Nc1cccc(Oc2ccnc3cc(C(=O)NCCc4nn[nH]n4)sc23)c1] | 489 | 7-{3-[(3-methyl-2-furoyl)amino]phenoxy}-N-[2-(2H-tetrazol-5-yl)ethyl]thieno[3,2-b]pyridine-2-carboxamide |
| 79 | 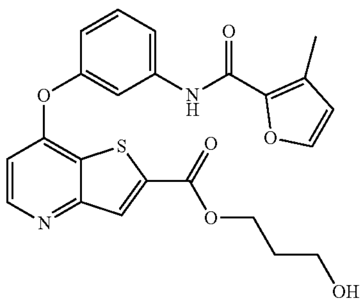 [SMILES: Cc1ccoc1C(=O)Nc1cccc(Oc2ccnc3cc(C(=O)OCCCO)sc23)c1] | 452 | 3-hydroxypropyl 7-{3-[(3-methyl-2-furoyl)amino]phenoxy}thieno[3,2-b]pyridine-2-carboxylate |
| 80 | 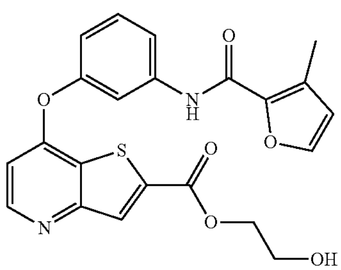 [SMILES: Cc1ccoc1C(=O)Nc1cccc(Oc2ccnc3cc(C(=O)OCCO)sc23)c1] | 438 | 2-hydroxyethyl 7-{3-[(3-methyl-2-furoyl)amino]phenoxy}thieno[3,2-b]pyridine-2-carboxylate |
| 81 | 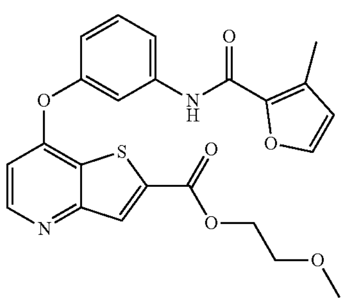 [SMILES: COCCOC(=O)c1cc2nccc(Oc3cccc(NC(=O)c4occc4C)c3)c2s1] | 452 | 2-methoxyethyl 7-{3-[(3-methyl-2-furoyl)amino]phenoxy}thieno[3,2-b]pyridine-2-carboxylate |
| 82 | 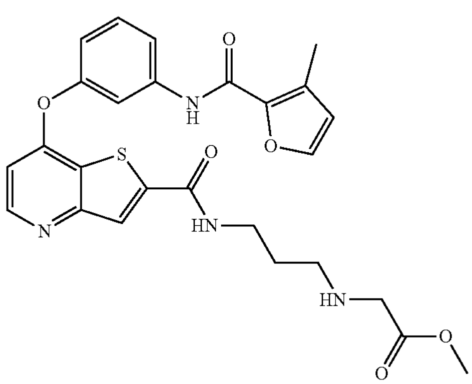 [SMILES: COC(=O)CNCCCNC(=O)c1cc2nccc(Oc3cccc(NC(=O)c4occc4C)c3)c2s1] | 522 | Methyl [(3-{[(7-{3-[(3-methyl-2-furoyl)amino]phenoxy}thieno[3,2-b]pyridin-2-yl)carbonyl]amino}propyl)amino]acetate |

| Example# | Chemical Structure | MW | Chemical Name |
|---|---|---|---|
| 83 | 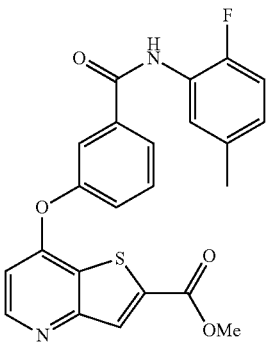 | 436 | Methyl 7-(3-((2-fluoro-5-methylphenyl)carbamoyl)phenoxy)thieno[3,2-b]pyridine-2-carboxylate |
| 84 | 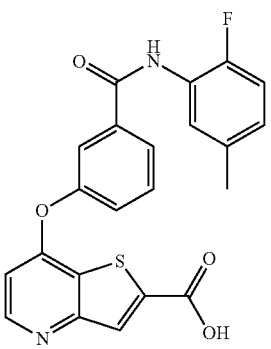 | 422 | 7-(3-{[(2-fluoro-5-methylphenyl)amino]carbonyl}phenoxy)thieno[3,2-b]pyridine-2-carboxylic acid |
| 85 | 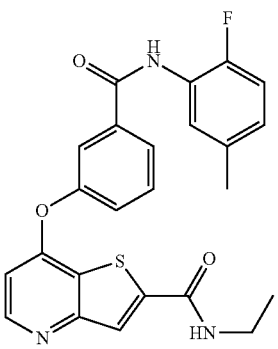 [SMILES: CCNC(=O)c1cc2nccc(Oc3cccc(C(=O)Nc4cc(C)ccc4F)c3)c2s1] | 449 | N-ethyl-7-(3-{[(2-fluoro-5-methylphenyl)amino]carbonyl}phenoxy)thieno[3,2-b]pyridine-2-carboxamide |
| 86 | 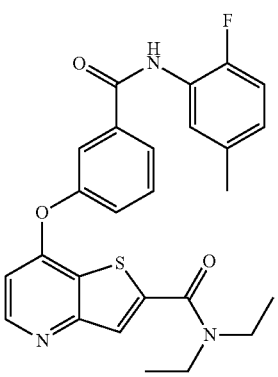 [SMILES: CCN(CC)C(=O)c1cc2nccc(Oc3cccc(C(=O)Nc4cc(C)ccc4F)c3)c2s1] | 477 | N,N-diethyl-7-(3-{[(2-fluoro-5-methylphenyl)amino]carbonyl}phenoxy)thieno[3,2-b]pyridine-2-carboxamide |

| Example# | Chemical Structure | MW | Chemical Name |
|---|---|---|---|
| 87 | 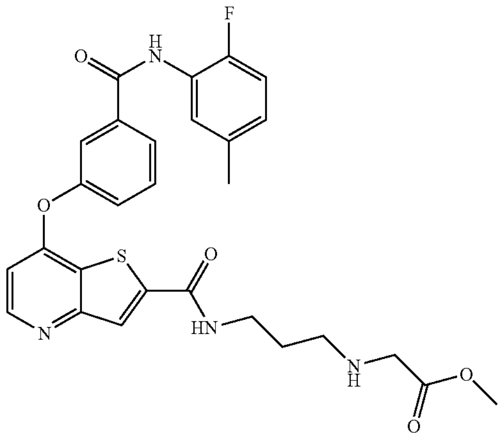 [SMILES: COC(=O)CNCCCNC(=O)c1cc2nccc(Oc3cccc(C(=O)Nc4cc(C)ccc4F)c3)c2s1] | 550 | Methyl {[3-({[7-(3-{[(2-fluoro-5-methylphenyl)amino]carbonyl}phenoxy)thieno[3,2-b]pyridin-2-yl]carbonyl}amino)propyl]amino}acetate |

3.1 Compound Synthesis and Characterization
Compound F1

Methyl 7-[4-({[(2-fluoro-5-methylphenyl)amino]carbonyl}amino)phenoxy]thieno[3,2-b]pyridine-2-carboxylate

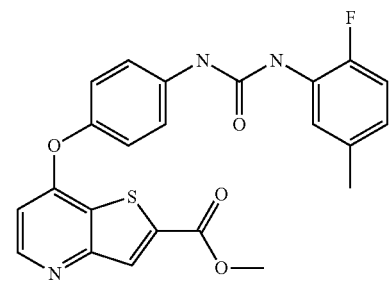 [SMILES: COC(=O)c1cc2nccc(Oc3ccc(NC(=O)Nc4cc(C)ccc4F)cc3)c2s1]

To a stirred solution of methyl 7-bromothieno[3,2-b]pyridine-2-carboxylate (200 mg, 0.74 mmol) in 8 ml of DMSO, were added CuBr (10 mg, 0.074 mmol), ethyl 2-cyclohexanonecarboxylate (26 mg, 0.15 mmol), cesium carbonate (500 mg, 1.54 mmol) and 4-aminophenol (96 mg, 0.88 mmol). The mixture was purged with nitrogen for 10 minutes, and then heated at 70° C. under $N_2$ for 3 hours. The reaction was cooled to room temperature and poured into 100 ml of water. The precipitates were filtered, washed with water and dried to give the crude aniline intermediate as a pale green solid (~140 mg). This crude material was dissolved in 10 ml of THF, and 2-fluoro-5-methylphenyl isocyanate (70 mg, 0.46 mmol) was added. The mixture was stirred at room temperature for 5 hours, and poured into 100 ml of water. The brown precipitates were filtered, washed with water and dried to give the crude product, which was purified by silica gel chromatography, eluting with 2-3% MeOH/CHCl$_3$ to give methyl 7-[4-({[(2-fluoro-5-methylphenyl)amino]carbonyl}amino)phenoxy]thieno[3,2-b]pyridine-2-carboxylate as light brown solid. Yield: 90 mg, 27%.

$^1$H NMR (d$_6$-DMSO) d: 9.25 (s, 1H), 8.61 (d, J=5.3 Hz, 1H), 8.50 (br. s., 1H), 8.21 (s, 1H), 7.96 (d, J=6.7 Hz, 1H), 7.58 (d, J=8.8 Hz, 2H), 7.25 (d, J=8.8 Hz, 2H), 7.09 (dd, J=11.4, 8.2 Hz, 1H), 6.71-6.85 (m, 2H), 3.91 (s, 3H), 2.26 (s, 3H)

LR MS (ES+): 452 (MH), 474 (M+Na$^+$)

LR MS (ES−): 450 (M−H)

Compound F2

7-[4-({[(2-Fluoro-5-methylphenyl)amino]carbonyl}amino)phenoxy]thieno[3,2-b]pyridine-2-carboxylic acid

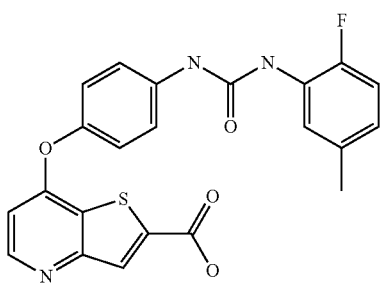

To a stirred suspension of methyl 7-[4-({[(2-fluoro-5-methylphenyl)amino]carbonyl}amino)-phenoxy]thieno[3,2-b]pyridine-2-carboxylate (50 mg, 0.11 mmol) in MeOH (3 ml), was added 0.4M LiOH/MeOH solution (10 ml, 4.0 mmol). The mixture was heated at 50° C. for 7 hours, and poured into 100 ml of water. 1M HCl was added until pH=4. The resulting precipitates were filtered, washed with water and dried in vacuo to give 7-[4-({[(2-fluoro-5-methylphenyl)amino]carbonyl}amino)phenoxy]thieno[3,2-b]pyridine-2-carboxylic acid as light grey solid. Yield: 40 mg, 83%.

$^1$H NMR (DMSO-d$_6$) δ: 13.88 (br. s., 1H), 9.19 (s, 1H), 8.58 (d, J=5.3 Hz, 1H), 8.47 (d, J=2.6 Hz, 1H), 8.10 (s, 1H), 7.96 (dd, J=7.9, 1.8 Hz, 1H), 7.53-7.59 (m, 2H), 7.22-7.27 (m, 2H), 7.08 (dd, 1H), 6.77-6.80 (m, 1H), 6.73 (d, J=5.6 Hz, 1H), 2.25 (s, 3H)

LR MS (ES−): 436 (M−H)

Compound F3

Methyl 7-[3-({[(2-fluoro-5-methylphenyl)amino]carbonyl}amino)phenoxyl]thieno[3,2-b]pyridine-2-carboxylate

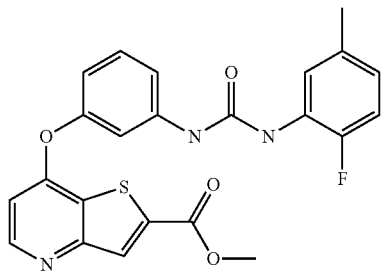 [SMILES: COC(=O)c1cc2nccc(Oc3cccc(NC(=O)Nc4cc(C)ccc4F)c3)c2s1]

prepared using procedures similar to Compound F1.

$^1$H NMR (DMSO-$d_6$) δ: 9.51 (s, 1H), 8.64 (d, J=5.3 Hz, 1H), 8.60 (s, 1H), 8.21 (s, 1H), 7.87 (dd, J=7.8, 1.6 Hz, 1H), 7.58 (t, J=2.1 Hz, 1H), 7.41 (t, J=8.1 Hz, 1H), 7.23 (dd, J=8.2, 1.2 Hz, 1H), 7.06 (dd, J=11.3, 8.4 Hz, 1H), 6.91 (dd, J=7.9, 1.8 Hz, 1H), 6.85 (d, J=5.3 Hz, 1H), 6.77 (td, J=5.2, 2.2 Hz, 1H), 3.91 (s, 3H), 2.21 (s, 3H)

LR MS (ES+): 452 (MH), 474 (M+Na$^+$)

LR MS (ES−): 450 (M−H)

Compound F4

Methyl 7-[4-({[(2-fluoro-5-methylphenyl)amino]carbonyl}amino)phenyl]thieno[3,2-b]pyridine-2-carboxylate

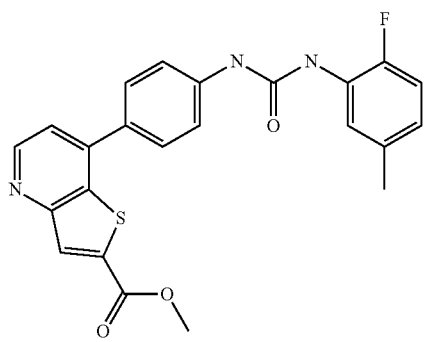 [SMILES: COC(=O)c1cc2nccc(-c3ccc(NC(=O)Nc4cc(C)ccc4F)cc3)c2s1]

To a mixture of methyl 7-bromothieno[3,2-b]pyridine-2-carboxylate (68 mg, 0.25 mmol) and 1-(2-fluoro-5-methylphenyl)-3-[4-(4,4,5,5-tetramethyl-1,3,2-dioxaborolan-2-yl)phenyl]urea (102 mg, 0.28 mmol) in 8 ml of 1,4-dioxane, was added PdCl$_2$(PPh$_3$)$_2$ (10 mg, 0.014 mmol) and 1M Na$_2$CO$_3$ aqueous solution (0.25 ml, 0.5 mmol). The mixture was heated at 70° C. under N$_2$ for 1 hour, cooled to room temperature and poured into 100 ml of water. The brown precipitates were filtered, washed with water and dried to give the crude product, which was purified by silica gel chromatography, eluting with 2-3% MeOH/CHCl$_3$ to give methyl 7-[4-({[(2-fluoro-5-methylphenyl)amino]carbonyl}amino)phenyl]thieno[3,2-b]pyridine-2-carboxylate as light yellow solid. Yield: 30 mg, 28%.

$^1$H NMR (d$_6$-DMSO) d: 9.38 (s, 1H), 8.84 (d, J=4.7 Hz, 1H), 8.58 (d, J=2.1 Hz, 1H), 8.28 (s, 1H), 7.60-8.06 (m, 6H), 7.06-7.19 (m, 1H), 6.82 (br. s., 1H), 3.93 (s, 3H), 2.28 (s, 3H)

LR MS (ES−): 434 (M−H)

Compound F5

7-[4-({[(2-fluoro-5-methylphenyl)amino]carbonyl}amino)phenyl]thieno[3,2-b]pyridine-2-carboxylic acid

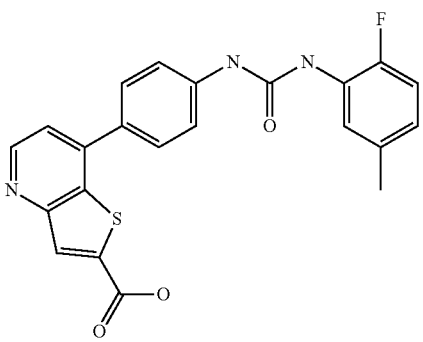 [SMILES: Cc1ccc(F)c(NC(=O)Nc2ccc(-c3ccnc4cc(C(=O)O)sc34)cc2)c1]

To a stirred solution of methyl 7-[4-({[(2-fluoro-5-methylphenyl)amino]carbonyl}amino)phenyl]thieno[3,2-b]pyridine-2-carboxylate (20 mg, 0.046 mmol) in THF/MeOH (5 ml/5 ml) was added 1M NaOH (2.0 ml, 2.0 mmol). The mixture was heated at 70° C. for 30 minutes, cooled to room temperature and poured into 50 ml of water. 1M HCl was added until pH=4 and the resulting precipitates were filtered, washed with water and dried in vacuo to give 7-[4-({[(2-fluoro-5-methylphenyl)amino]carbonyl}amino)phenyl]thieno[3,2-b]pyridine-2-carboxylic acid.

Yield: 20 mg, 100%.

LR MS (ES−): 420 (M−H)

Preparation of 7-chlorothieno[3,2-b]pyridine

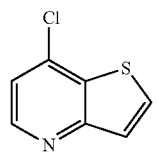

Thieno[3,2-b]pyridin-7-ol (20 g, 0.132 mol) was suspended in phosphorous oxy chloride (80.9 g, 0.528 mol) and stirred at 100□C for 2 hours. The solution was cooled to room temperature and was poured over ice. The aqueous solution was neutralized with sodium hydroxide and the resulting precipitate was collected by filtration and washed with water. The filter cake was taken up in dichloromethane and dried over magnesium sulfate. The solution was filtered and the filtrate was concentrated to dryness to give 7-chlorothieno[3,2-b]pyridine as a brown liquid which solidified to a beige solid under high vacuum. Yield: 20.4 g (91%); MS [M+H]$^+$ 169.9; $^1$HNMR (CDCl$_3$) δ: □8.7 (d, 1H), 7.8 (d, 1H), 7.6 (d, 1H), 7.3 (d, 1H) ppm.

Preparation of methyl 7-chlorothieno[3,2-b]pyridine-2-carboxylate

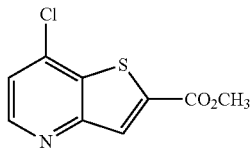 [SMILES: COC(=O)c1cc2nccc(Cl)c2s1]

7-chlorothieno[3,2-b]pyridine (19.7 g, 0.116 mol) was taken up in THF (400 mL) and cooled to approximately −70 □C. The n-butyllithium (1.6M, 80 mL, 0.128 mol) was added dropwise with stirring under an atmosphere of nitrogen. The solution was stirred at −70 □C for 1 hour at which time neat methyl chloroformate was added via dropwise addition. The reaction mixture gradually warmed to room temperature and was stirred for over the weekend. The reaction mixture was treated with 25 mL of methanol and then concentrated to dryness leaving a maroon residue. The crude solid was taken up in dichloromethane and passed through a silica gel column eluting with 1:1 hexane/ethyl acetate. Fractions containing the product were combined and concentrated to give a red solid. Trituration with 9:1 hexane/diethyl ether afforded methyl 7-chlorothieno[3,2-b]pyridine-2-carboxylate as a pink solid after filtration. Yield: 14.5 g (55%); MS [M+H]$^+$ 227.9; $^1$HNMR (CDCl$_3$) δ: □8.7 (d, 1H), 8.3 (s, 1H), 7.4 (d, 1H) ppm.

Preparation of methyl 7-(4-amino-3-fluorophenoxy)thieno[3,2-b]pyridine-2-carboxylate

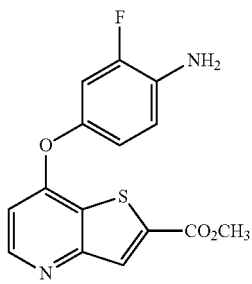 [SMILES: COC(=O)c1cc2nccc(Oc3ccc(N)c(F)c3)c2s1]

Methyl 7-chlorothieno[3,2-b]pyridine-2-carboxylate (5 g, 0.022 mol) and the 4-amino-3-fluorophenol (3.3 g, 0.026 mol) were added to a round bottom flask containing cesium carbonate (14.8 g, 0.045 mol), ethyl-2-cyclohexanone carboxylate (0.73 g, 0.004 mol), and copper (I) chloride (0.22 g, 0.002 mol). The mixture was diluted with DMSO (250 mL) and stirred at 70 □C under an atmosphere of nitrogen for 2 hours. The dark reaction mixture was cooled to room temperature and poured into ethyl acetate (500 mL)/water (1 L) with vigorous stirring. The mixture was filtered through celite and the organic portion of the filtrate was separated and dried over magnesium sulfate. The solution was filtered and the filtrate was concentrated to give a purple viscous liquid. The crude product was taken up in dichloromethane and passed through a silica gel column eluting with 1:1 hexane/ethyl acetate. Fractions containing the product were combined and concentrated to afford methyl 7-(4-amino-3-fluorophenoxy)thieno[3,2-b]pyridine-2-carboxylate as red solid. Yield: 1.62 g (23%); MS [M+H]$^+$ 319.1

Compound F9 methyl 7-(3-fluoro-4-(3-(2-fluoro-5-methylphenyl)ureido)phenoxy)thieno[3,2-b]pyridine-2-carboxylate

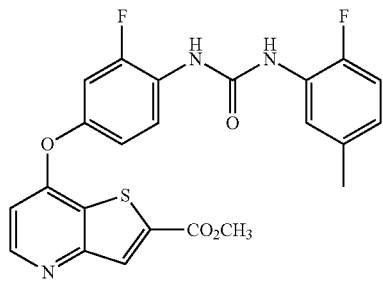 [SMILES: COC(=O)c1cc2nccc(Oc3ccc(NC(=O)Nc4cc(C)ccc4F)c(F)c3)c2s1]

Methyl 7-(4-amino-3-fluorophenoxy)thieno[3,2-b]pyridine-2-carboxylate (1.62 g, 5.1 mmol) was taken up in 55 mL of ethyl acetate followed by the dropwise addition of 2-fluoro-5-methylphenyl isocyanate (0.85 g, 5.6 mmol) in 5 mL ethyl acetate. The solution afforded a lavender solid after stirring at room temperature for overnight. The solid was collected by filtration and washed with diethyl ether to give methyl 7-(3-fluoro-4-(3-(2-fluoro-5-methylphenyl)ureido)phenoxy)thieno[3,2-b]pyridine-2-carboxylate as an off white solid. Yield: 1.75 g (73%); MS [M+H]$^+$ 470.1; $^1$HNMR (DMSO-d$_6$) δ: □9.2 (s, 1H), 9.0 (s, 1H), 8.6 (d, 1H), 8.3 (t, 1H, 8.1 (s, 1H), 8.0 (d, 1H), 7.5 (d, 1H), 7.2 (m, 2H), 6.8 (m, 2H), 3.9 (s, 3H), 2.1 (s, 3H) ppm.

Compound F10 methyl 3-[({7-[3-fluoro-4-({[(2-fluoro-5-methylphenyl)amino]carbonyl}amino) phenoxy]thieno[3,2-b]pyridin-2-yl}carbonyl)amino]propanoate

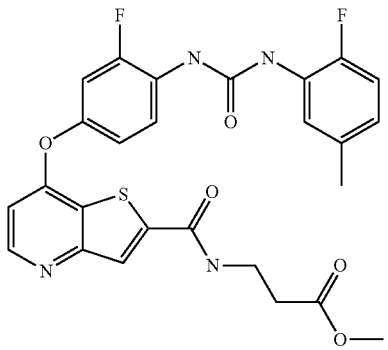 [SMILES: COC(=O)CCNC(=O)c1cc2nccc(Oc3ccc(NC(=O)Nc4cc(C)ccc4F)c(F)c3)c2s1]

$^1$H NMR (DMSO-d$_6$) δ: 9.10 (br. s., 1H), 9.03 (t, J=5.4 Hz, 1H), 8.96 (br. s., 1H), 8.56 (d, J=5.3 Hz, 1H), 8.26 (t, J=9.1 Hz, 1H), 8.21 (s, 1H), 7.98 (d, J=7.6 Hz, 1H), 7.40 (dd, J=11.6, 2.5 Hz, 1H), 7.06-7.16 (m, 2H), 6.74-6.84 (m, 2H), 3.60 (s, 3H), 3.48-3.55 (m, 2H), 2.62 (t, J=6.9 Hz, 2H), 2.25 (s, 3H)

LR MS (ES+): 563 (M+Na$^+$)

LR MS (ES−): 539 (M−H)

Compound F11 methyl 3-[({7-[4-({[(2-fluoro-5-methylphenyl)amino]carbonyl}amino) phenoxy]thieno[3,2-b]pyridin-2-yl}carbonyl)amino]propanoate

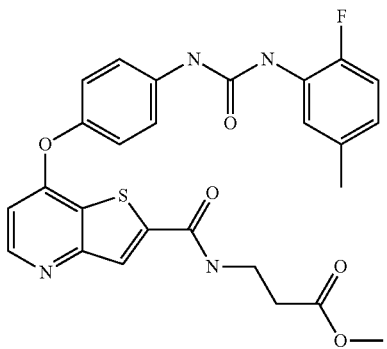 [SMILES: COC(=O)CCNC(=O)c1cc2nccc(Oc3ccc(NC(=O)Nc4cc(C)ccc4F)cc3)c2s1]

A mixture of 7-[4-({[(2-fluoro-5-methylphenyl)amino]carbonyl}amino)phenoxy]thieno[3,2-b]pyridine-2-carboxylic acid (120 mg, 0.27 mmol), HATU (122 mg, 0.32 mmol) and N,N-diisopropylethylamine (105 mg, 0.81 mmol) in anhydrous THF (10 ml) was stirred at room temperature for 10 minutes, followed by addition of (R)-3-pyrrolidinol (56 mg, 0.40 mmol). The mixture was heated and stirred at 60° C. for 30 minutes and poured into 100 ml of water. 2M HCl was added dropwise until pH=4. The precipitates were filtered, washed with water and dried in vacuo to give methyl 3-[({7-[4-({[(2-fluoro-5-methylphenyl)amino]carbonyl}amino)phenoxy]thieno[3,2-b]pyridin-2-yl}carbonyl)amino]propanoate as white solid. Yield: 128 mg, 90%.

$^1$H NMR (DMSO-$d_6$) δ: 9.18 (s, 1H), 9.01 (t, 1H), 8.54 (br. s., 1H), 8.47 (br. s., 1H), 8.20 (br. s., 1H), 7.95 (d, J=6.7 Hz, 1H), 7.55 (d, J=8.8 Hz, 2H), 7.22 (d, J=8.5 Hz, 2H), 7.08 (dd, J=11.0, 8.7 Hz, 1H), 6.78 (br. s., 1H), 6.69 (d, J=5.0 Hz, 1H), 3.60 (s, 3H), 3.46-3.55 (m, 2H), 2.62 (t, J=6.7 Hz, 2H), 2.25 (s, 3H)

LR MS (ES+): 545 (M+Na$^+$)
LR MS (ES−): 521 (M−H)

Compound F6

3-[({7-[4-({[(2-fluoro-5-methylphenyl)amino]carbonyl}amino)phenoxy]thieno[3,2-b]pyridin-2-yl}carbonyl)amino]propanoic acid

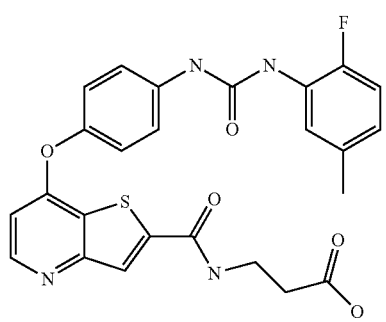 [SMILES: Cc1ccc(F)c(NC(=O)Nc2ccc(Oc3ccnc4cc(C(=O)NCCC(=O)O)sc34)cc2)c1]

to a stirred solution of methyl 3-[({7-[4-({[(2-fluoro-5-methylphenyl)amino]carbonyl}amino)phenoxy]thieno[3,2-b]pyridin-2-yl}carbonyl)amino]propanoate (98 mg, 0.19 mmol) in a mixture of solvents THF/MeOH (10 ml/10 ml) was added 2 ml of 1M NaOH (2 mmol) solution. The mixture was stirred at room temperature for 1 hour and poured into 100 ml of water. 2M HCl was added until pH=4. The resulting precipitates were filtered, washed with water, and dried in vacuo to give 3-[({7-[4-({[(2-fluoro-5-methylphenyl)amino]carbonyl}amino)phenoxy]thieno[3,2-b]pyridin-2-yl}carbonyl)amino]propanoic acid as off-white solid. Yield: 90 mg, 95%.

$^1$H NMR (DMSO-$d_6$) δ: 12.25 (br. s., 1H), 9.18 (s, 1H), 8.99 (t, J=5.1 Hz, 1H), 8.54 (d, J=5.6 Hz, 1H), 8.47 (br. s., 1H), 8.21 (s, 1H), 7.95 (d, J=6.5 Hz, 1H), 7.55 (d, J=8.8 Hz, 2H), 7.22 (d, J=8.8 Hz, 2H), 7.08 (dd, J=11.0, 8.4 Hz, 1H), 6.78 (br. s., 1H), 6.68 (d, J=5.3 Hz, 1H), 3.42-3.53 (m, 2H), 2.53 (t, J=6.9 Hz, 2H), 2.25 (s, 3H)

LR MS (ES−): 507 (M−H)

Compound F7

3-[({7-[3-fluoro-4-({[(2-fluoro-5-methylphenyl)amino]carbonyl}amino)phenoxy]thieno[3,2-b]pyridin-2-yl}carbonyl)amino]propanoic acid

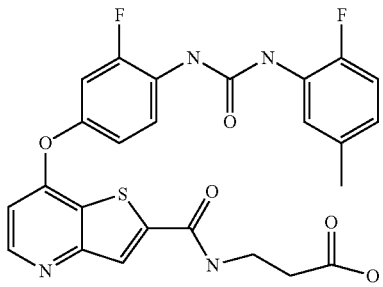 [SMILES: Cc1ccc(F)c(NC(=O)Nc2ccc(Oc3ccnc4cc(C(=O)NCCC(=O)O)sc34)cc2F)c1]

$^1$H NMR (DMSO-$d_6$) δ: 12.26 (br. s., 1H), 9.09 (br. s., 1H), 9.00 (t, J=4.7 Hz, 1H), 8.96 (br. s., 1H), 8.56 (d, J=5.3 Hz, 1H), 8.25 (t, J=9.0 Hz, 1H), 8.22 (s, 1H), 7.98 (d, J=7.0 Hz, 1H), 7.35-7.44 (m, 1H), 7.05-7.16 (m, 2H), 6.71-6.85 (m, 2H), 3.42-3.54 (m, 2H), 2.53 (t, J=6.7 Hz, 2H), 2.25 (s, 3H)

LR MS (ES−): 525 (M−H)

Compound F8

7-[3-fluoro-4-({[(2-fluoro-5-methylphenyl)amino]carbonyl}amino)phenoxy]thieno[3,2-b]pyridine-2-carboxylic acid

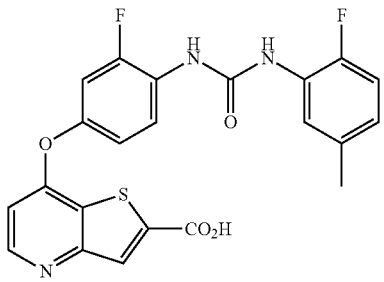 [SMILES: Cc1ccc(F)c(NC(=O)Nc2ccc(Oc3ccnc4cc(C(=O)O)sc34)cc2F)c1]

Methyl 7-(3-fluoro-4-(3-(2-fluoro-5-methylphenyl)ureido)phenoxy)thieno[3,2-b]pyridine-2-carboxylate (1.84 g, 3.92 mmol) was taken up in 100 mL THF followed by the dropwise addition of 1N sodium hydroxide (4.8 mL, 4.8 mmol). The solution was stirred at room temperature for 3 hours, at which time an additional 2.4 mL of 1N sodium hydroxide was added. The solution was stirred at room temperature for overnight and the resulting mixture was diluted with 75 mL of water and acidified using 1N HCl. The insoluble material was separated by filtration and the filter cake was suspended in ethyl acetate and stirred for several minutes before filtering. The filter cake was washed several times with ethyl acetate and dried under high vacuum to give 7-[3-fluoro-4-({[(2-fluoro-5-methylphenyl)amino]carbonyl}amino)phenoxy]thieno[3,2-b]pyridine-2-carboxylic acid as an off white solid. Yield: 1.6 g (90%); MS [M+H]$^+$ 456.1; $^1$HNMR (DMSO-d$_6$) δ: □ 13.9 (bs, 1H), □9.2 (s, 1H), 9.0 (s, 1H), 8.6 (d, 1H), 8.3 (t, 1H), 8.1 (s, 1H), 8.0 (d, 1H), 7.5 (d, 1H), 7.2 (m, 2H), 6.8 (m, 2H), 2.1 (s, 3H) ppm.

Other compounds which may be made according to the teachings of the present application include:

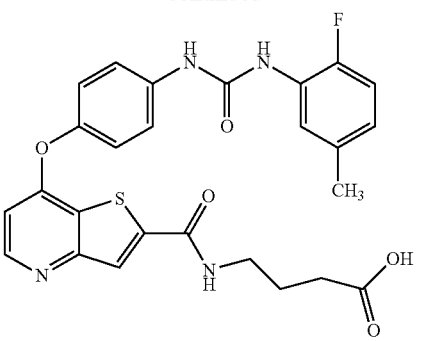

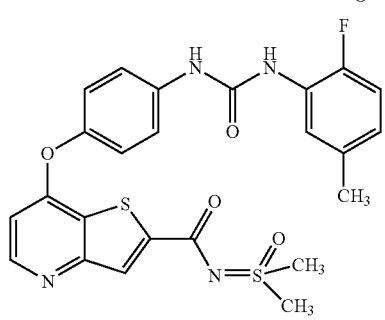

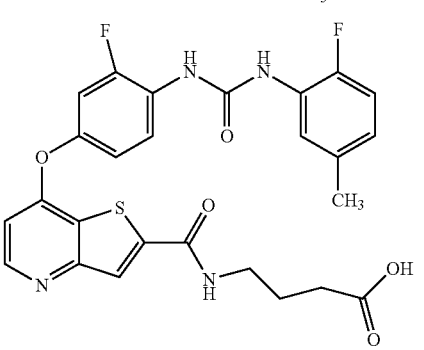

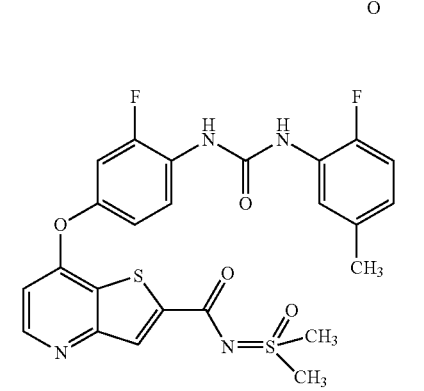

-continued

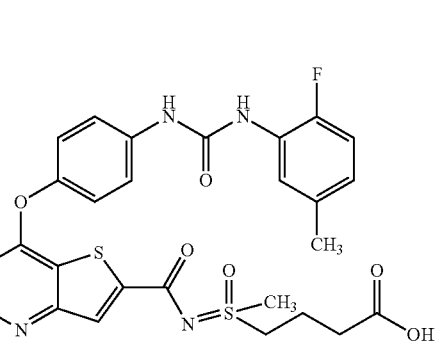

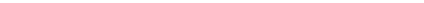

-continued

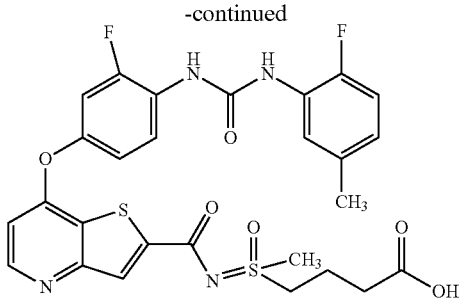

Synthesis and Characterization of the Additional Compounds is Listed Below.

Example 12

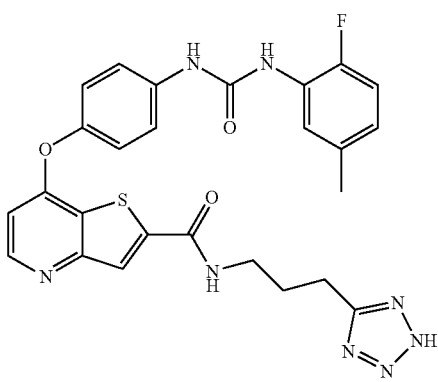 [SMILES: Cc1ccc(F)c(NC(=O)Nc2ccc(Oc3ccnc4cc(C(=O)NCCCc5nn[nH]n5)sc34)cc2)c1]

7-[4-({[(2-fluoro-5-methylphenyl)amino]carbonyl}amino)phenoxy]-N-[3-(2H-tetrazol-5-yl)propyl]thieno[3,2-b]pyridine-2-carboxamide to a stirred suspension of 7-[4-({[(2-fluoro-5-methylphenyl)amino]carbonyl}amino)phenoxy]thieno[3,2-b]pyridine-2-carboxylic acid (Compound F1) (100 mg, 0.23 mmol) in 10 ml of anhydrous acetonitrile were added HATU (95 mg, 0.25 mmol) and N,N-diisopropylethylamine (89 mg, 0.69 mmol). The mixture was stirred at room temperature for 20 minutes, followed by addition of 3-(1H-tetrazol-5-yl)propan-1-amine hydrochloride (57 mg, 0.35 mmol). The mixture was stirred at room temperature for another 40 minutes and poured into 100 ml of water with vigorous stirring. 1M HCl was added dropwise until pH=5. The precipitates were filtered, washed with water and dried in vacuo to give the crude, which was purified by silica gel chromatography eluting with 8-12% methanol in chloroform containing 0.5% of triethylamine to give 7-[4-({[(2-fluoro-5-methylphenyl)amino]carbonyl}amino)phenoxy]-N-[3-(2H-tetrazol-5-yl)propyl]thieno[3,2-b]pyridine-2-carboxamide as white solid. Yield: 50 mg, 40%.

$^1$H NMR (DMSO-$d_6$): 9.28 (s, 1H), 9.18 (t, J=5.6 Hz, 1H), 8.57 (d, J=5.6 Hz, 1H), 8.54 (d, J=2.6 Hz, 1H), 8.26 (s, 1H), 7.98 (dd, J=7.9, 2.3 Hz, 1H), 7.57-7.60 (m, 2H), 7.24-7.27 (m, 2H), 7.11 (dd, J=11.3, 8.4 Hz, 1H), 6.80-6.82 (m, 1H), 6.71 (d, J=5.6 Hz, 1H), 3.37-3.40 (m, 2H), 2.87-2.91 (m, 2H), 2.27 (s, 3H), 1.98 (quin, J=7.3 Hz, 2H)

LR MS (ES−): 545 (M−H)

The following Example 13 was prepared using the experiment procedure described in Example 12, but with the appropriate reagent, reaction conditions and reactant substitutions that will be readily realized by those of ordinary skill in this art without the exercise of undue experimentation.

Example 13

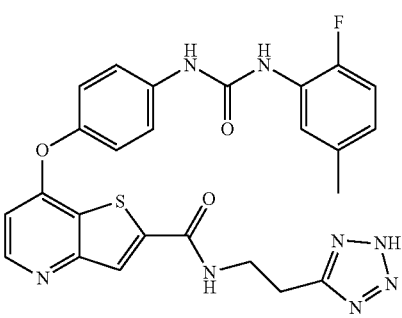 [SMILES: Cc1ccc(F)c(NC(=O)Nc2ccc(Oc3ccnc4cc(C(=O)NCCc5nn[nH]n5)sc34)cc2)c1]

7-[4-({[(2-fluoro-5-methylphenyl)amino]carbonyl}amino)phenoxy]-N-[2-(2H-tetrazol-5-yl)ethyl]thieno[3,2-b]pyridine-2-carboxamide $^1$H NMR (DMSO-$d_6$): 9.22 (s, 1H), 9.12 (t, J=5.9 Hz, 1H), 8.57 (d, J=5.6 Hz, 1H), 8.51 (d, J=2.9 Hz, 1H), 8.18 (s, 1H), 7.98 (dd, J=8.4, 1.9 Hz, 1H), 7.57-7.60 (m, 1H), 7.58 (d, J=9.1 Hz, 1H), 7.24-7.27 (m, 1H), 7.25 (d, J=9.1 Hz, 1H), 7.11 (dd, J=11.3, 8.4 Hz, 1H), 6.80-6.83 (m, 1H), 6.72 (d, J=5.6 Hz, 1H), 3.66-3.69 (m, 2H), 3.20 (t, J=7.0 Hz, 2H), 2.28 (s, 3H)

LR MS (ES−): 531 (M−H)

Example 14

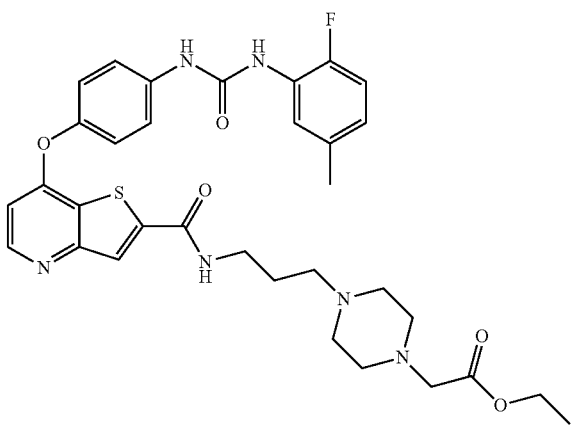 [SMILES: CCOC(=O)CN1CCN(CCCNC(=O)c2cc3nccc(Oc4ccc(NC(=O)Nc5cc(C)ccc5F)cc4)c3s2)CC1]

ethyl (4-{3-[({7-[4-({[(2-fluoro-5-methylphenyl)amino]carbonyl}amino)phenoxy]thieno[3,2-b]pyridin-2-yl}carbonyl)amino]propyl}piperazin-1-yl)acetate to a stirred solution of 7-[4-({[(2-fluoro-5-methylphenyl)amino]carbonyl}amino)phenoxy]-N-(3-oxopropyl)thieno[3,2-b]pyridine-2-carboxamide (180 mg, 0.36 mmol) and 1-(ethoxycarbonylmethyl)piperazine (124 mg, 0.72 mmol) in anhydrous DMF was added 2 drops of acetic acid. The solution was stirred at room temperature for 30 minutes, followed by addition of 1M NaCNBH$_3$ solution in THF (0.72 ml, 0.72 mmol). Stirring was continued for another hour, and the mixture was poured into 100 ml of water. The precipitates were filtered to give the crude, which was purified by silica gel chromatography eluting with 8-12% of methanol in chloroform to give ethyl (4-{3-[({7-[4-({[(2-fluoro-5-methylphenyl)amino]carbonyl}amino)phenoxy]thieno[3,2-b]pyridin-2-yl}carbonyl)amino]propyl}piperazin-1-yl)acetate as light yellow solid. Yield: 70 mg, 30%.

$^{1}$H NMR (DMSO-d$_{6}$): 9.20 (s, 1H), 8.90 (t, J=5.7 Hz, 1H), 8.53 (d, J=5.3 Hz, 1H), 8.48 (dd, J=2.3, 0.6 Hz, 1H), 8.19 (s, 1H), 7.93-7.98 (m, 1H), 7.53-7.58 (m, 2H), 7.20-7.24 (m, 2H), 7.08 (dd, J=11.4, 8.5 Hz, 1H), 6.75-6.81 (m, 1H), 6.68 (d, J=5.6 Hz, 1H), 4.04 (q, J=7.0 Hz, 2H), 3.25-3.33 (m, 2H), 3.15 (s, 2H), 2.27-2.43 (m, 10H), 2.25 (s, 3H), 1.68 (quin, J=7.1 Hz, 2H), 1.15 (t, J=7.0 Hz, 3H)

LR MS (ES+): 671 (M+Na$^{+}$)
LR MS (ES−): 647 (M−H)

The following Examples 15 through 17 were prepared using the experiment procedure described in Example 14, but with the appropriate reagent, reaction conditions and reactant substitutions that will be readily realized by those of ordinary skill in this art without the exercise of undue experimentation.

Example 15

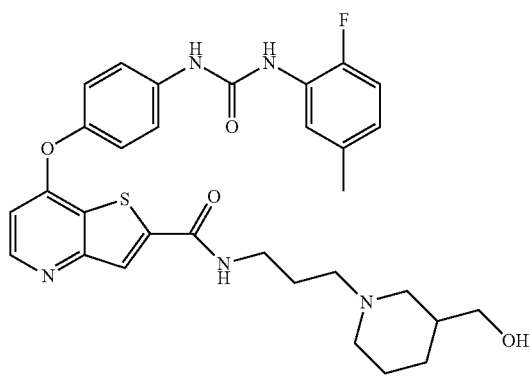 [SMILES: Cc1ccc(F)c(NC(=O)Nc2ccc(Oc3ccnc4cc(C(=O)NCCCN5CCCC(CO)C5)sc34)cc2)c1]

7-[4-({[(2-fluoro-5-methylphenyl)amino]carbonyl}amino)phenoxy]-N-{3-[3-(hydroxymethyl)piperidin-1-yl]propyl}thieno[3,2-b]pyridine-2-carboxamide

LR MS (ES+): 592 (MH$^{+}$)

Example 16

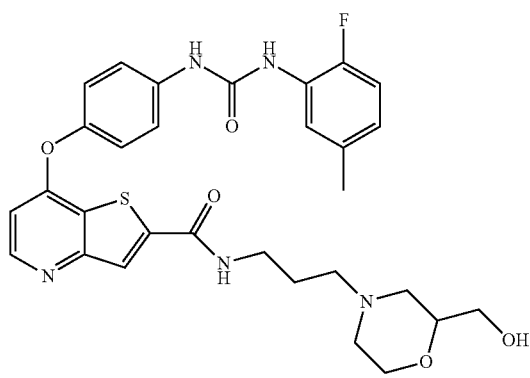 [SMILES: Cc1ccc(F)c(NC(=O)Nc2ccc(Oc3ccnc4cc(C(=O)NCCCN5CCOC(CO)C5)sc34)cc2)c1]

7-[4-({[(2-fluoro-5-methylphenyl)amino]carbonyl}amino)phenoxy]-N-{3-[2-(hydroxymethyl)morpholin-4-yl]propyl}thieno[3,2-b]pyridine-2-carboxamide LR MS (ES+): 616 (M+Na$^{+}$)
LR MS (ES−): 592 (M−H)

Example 17

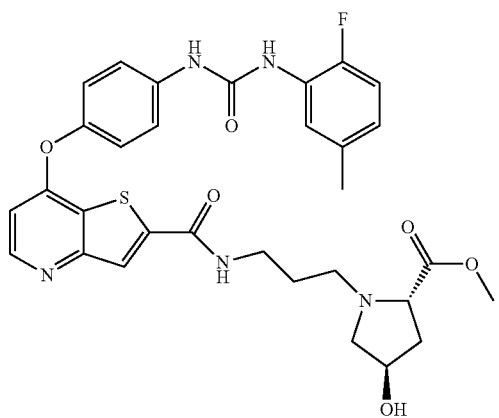 [SMILES: COC(=O)[C@@H]1C[C@@H](O)CN1CCCNC(=O)c1cc2nccc(Oc3ccc(NC(=O)Nc4cc(C)ccc4F)cc3)c2s1]

methyl rel-(2R,4S)-1-{3-[({7-[4-({[(2-fluoro-5-methylphenyl)amino]carbonyl}amino)phenoxy]thieno[3,2-b]pyridin-2-yl}carbonyl)amino]propyl}-4-hydroxypyrrolidine-2-carboxylate $^{1}$H NMR (DMSO-d$_{6}$): 9.22 (s, 1H), 8.92 (t, J=5.6 Hz, 1H), 8.56 (d, J=5.6 Hz, 1H), 8.50 (d, J=2.3 Hz, 1H), 8.20 (s, 1H), 7.98 (dd, J=7.6, 2.1 Hz, 1H), 7.57-7.60 (m, 2H), 7.24-7.27 (m, 2H), 7.11 (dd, J=11.3, 8.4 Hz, 1H), 6.80-6.83 (m, 1H), 6.71 (d, J=5.6 Hz, 1H), 4.89 (d, J=4.4 Hz, 1H), 4.20-4.26 (m, 1H), 3.61 (s, 3H), 3.40 (t, J=7.8 Hz, 1H), 3.32-3.36 (m, 2H), 3.25-3.28 (m, 1H), 2.70 (dt, J=12.0, 7.5 Hz, 1H), 2.49-2.52 (m, 1H), 2.28 (s, 3H), 2.26-2.29 (m, 1H), 1.96-2.01 (m, 1H), 1.89 (td, J=8.4, 4.0 Hz, 1H), 1.63-1.71 (m, 2H)

LR MS (ES+): 622 (MH+)
LR MS (ES−): 620 (M−H)

The following Example 18 was prepared using the experiment procedure described in Example 25, but with the appropriate reagent, reaction conditions and reactant substitutions that will be readily realized by those of ordinary skill in this art without the exercise of undue experimentation.

Example 18

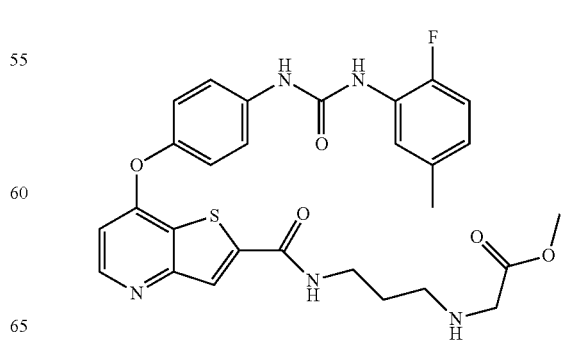

methyl ({3-[({7-[4-({[(2-fluoro-5-methylphenyl)amino]carbonyl}amino)phenoxy]thieno[3,2-b]pyridin-2-yl}carbonyl)amino]propyl}amino)acetate $^1$H NMR (DMSO-d$_6$): 9.22 (s, 1H), 8.95 (t, J=5.7 Hz, 1H), 8.56 (d, J=5.3 Hz, 1H), 8.51 (d, J=2.6 Hz, 1H), 8.22 (s, 1H), 7.98 (dd, J=7.8, 2.2 Hz, 1H), 7.57-7.60 (m, 2H), 7.24-7.27 (m, 2H), 7.11 (dd, J=11.3, 8.4 Hz, 1H), 6.80-6.83 (m, 1H), 6.72 (s, 1H), 3.63 (s, 3H), 3.38 (s, 2H), 3.32-3.36 (m, 2H), 2.61 (t, J=6.9 Hz, 2H), 2.28 (s, 3H), 1.69 (quin, J=7.0 Hz, 2H) LR MS (ES−): 564 (M−H)

The following Example 19 was prepared using the experiment procedure described in Example 26, but with the appropriate reagent, reaction conditions and reactant substitutions that will be readily realized by those of ordinary skill in this art without the exercise of undue experimentation.

Example 19

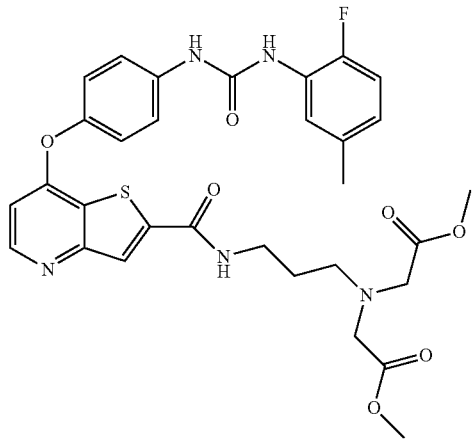 [SMILES: COC(=O)CN(CCCNC(=O)c1cc2nccc(Oc3ccc(NC(=O)Nc4cc(C)ccc4F)cc3)c2s1)CC(=O)OC]

dimethyl 2,2'-({3-[({7-[4-({[(2-fluoro-5-methylphenyl)amino]carbonyl}amino)phenoxy]thieno[3,2-b]pyridin-2-yl}carbonyl)amino]propyl}imino)diacetate $^1$H NMR (DMSO-d$_6$): 9.21 (s, 1H), 8.88 (t, J=5.7 Hz, 1H), 8.57 (d, J=5.3 Hz, 1H), 8.50 (d, J=2.6 Hz, 1H), 8.21 (s, 1H), 7.98 (dd, J=7.9, 2.3 Hz, 1H), 7.57-7.60 (m, 2H), 7.24-7.27 (m, 2H), 7.11 (dd, J=11.3, 8.4 Hz, 1H), 6.80-6.83 (m, 1H), 6.71 (d, J=5.6 Hz, 1H), 3.60 (s, 6H), 3.54 (s, 4H), 3.32-3.35 (m, 2H), 2.72 (t, J=6.9 Hz, 2H), 2.28 (s, 3H), 1.67 (quin, J=6.9 Hz, 2H)
LR MS (ES+): 660 (M+Na$^+$)
LR MS (ES−): 636 (M−H)

Example 20

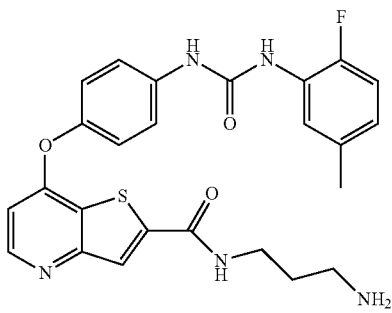 [SMILES: Cc1ccc(F)c(NC(=O)Nc2ccc(Oc3ccnc4cc(C(=O)NCCCN)sc34)cc2)c1]

N-(3-aminopropyl)-7-[4-({[(2-fluoro-5-methylphenyl)amino]carbonyl}amino)phenoxy]thieno[3,2-b]pyridine-2-carboxamide to a stirred suspension of tert-butyl (3-[({7-[4-({[(2-fluoro-5-methylphenyl)amino]carbonyl}amino)phenoxy]thieno[3,2-b]pyridin-2-yl}carbonyl)amino]propyl)carbamate (380 mg, 0.64 mmol) in 10 ml of methylene chloride was added 5 ml of trifluoroacetic acid. The mixture was stirred at room temperature for 30 minutes and evaporated to dryness under reduced pressure. The residue was re-dissolved in MeOH (5 ml) and poured into 100 ml of water with vigorous stirring. Saturated NaHCO$_3$ solution was added until pH=8-9. The precipitates were filtered, washed with water and dried in vacuo to give N-(3-aminopropyl)-7-[4-({[(2-fluoro-5-methylphenyl)amino]carbonyl}amino)phenoxy]thieno[3,2-b]pyridine-2-carboxamide as yellow solid. Yield: 270 mg, 85%.
LR MS (ES+): 516 (M+Na$^+$)
LR MS (ES−): 492 (M−H)

Example 21

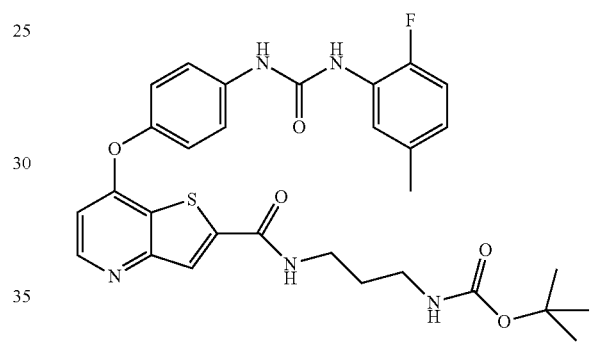

tert-butyl {3-[({7-[4-({[(2-fluoro-5-methylphenyl)amino]carbonyl}amino)phenoxy]thieno[3,2-b]pyridin-2-yl}carbonyl)amino]propyl}carbamate A mixture of 7-[4-({[(2-fluoro-5-methylphenyl)amino]carbonyl}amino)phenoxy]thieno[3,2-b]pyridine-2-carboxylic acid (300 mg, 0.69 mmol), HATU (288 mg, 0.76 mmol) and N,N-diisopropylethylamine (196 mg, 1.52 mmol) in anhydrous acetonitrile (10 ml) was stirred at room temperature for 30 minutes, followed by addition of N-Boc-1,3-propanediamine (180 mg, 1.03 mmol). The mixture was stirred for another 30 minutes and poured into 100 ml of water with vigorous stirring. 2M HCl was added dropwise until pH=6. The precipitates were filtered, washed with water and dried in vacuo to give tert-butyl (3-[({7-[4-({[(2-fluoro-5-methylphenyl)amino]carbonyl}amino)phenoxy]thieno[3,2-b]pyridin-2-yl}carbonyl)amino]propyl)carbamate as brown solid. Yield: 380 mg, 93%.
$^1$H NMR (DMSO-d$_6$): 9.25 (s, 1H), 8.89 (t, J=5.7 Hz, 1H), 8.57 (d, J=5.3 Hz, 1H), 8.53 (d, J=2.6 Hz, 1H), 8.22 (s, 1H), 7.98 (dd, J=7.6, 2.1 Hz, 1H), 7.57-7.60 (m, 2H), 7.24-7.26 (m, 2H), 7.11 (dd, J=11.3, 8.4 Hz, 1H), 6.81 (ddd, J=10.9, 5.4, 2.8 Hz, 1H), 6.71 (d, J=5.6 Hz, 1H), 6.70-6.72 (m, 1H), 3.27-3.30 (m, 2H), 3.00 (q, J=6.7 Hz, 2H), 2.28 (s, 3H), 1.67 (quin, J=7.1 Hz, 2H), 1.38 (s, 9H)
LR MS (ES+): 616 (M+Na$^+$)
LR MS (ES−): 592 (M−H)

Example 21A

Preparation of N-(3,3-diethoxypropyl)-7-[4-({[(2-fluoro-5-methylphenyl)amino]carbonyl}amino)phenoxy]thieno[3,2-b]pyridine-2-carboxamide

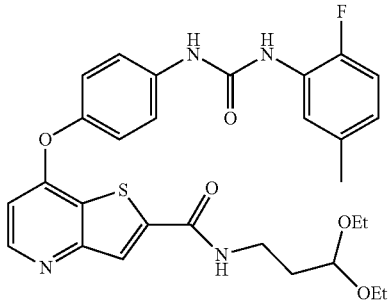 [SMILES: CCOC(CCNC(=O)c1cc2nccc(Oc3ccc(NC(=O)Nc4cc(C)ccc4F)cc3)c2s1)OCC]

to a stirred suspension of 7-[4-({[(2-fluoro-5-methylphenyl)amino]carbonyl}amino)phenoxy]thieno[3,2-b]pyridine-2-carboxylic acid (600 mg, 1.37 mmol) in 10 ml of anhydrous acetonitrile were added HATU (608 mg, 1.6 mmol) and N,N-diisopropylethylamine (388 mg, 3.0 mmol). The mixture was stirred at room temperature for 30 minutes, followed by addition of 1-amino-3,3-diethoxypropane (294 mg, 2.0 mmol). The mixture was stirred for another 10 minutes and poured into 100 ml of water with vigorous stirring. 1M HCl was added until pH=5. The precipitates were filtered, washed with water and dried in vacuo to give N-(3,3-diethoxypropyl)-7-[4-({[(2-fluoro-5-methylphenyl)amino]carbonyl}amino)phenoxy]thieno[3,2-b]pyridine-2-carboxamide as yellow solid. Yield: 680 mg, 88%.

$^1$H NMR (DMSO-$d_6$) δ: 9.21 (s, 1H), 8.90 (t, J=5.7 Hz, 1H), 8.57 (d, J=5.6 Hz, 1H), 8.50 (d, J=2.6 Hz, 1H), 8.22 (s, 1H), 7.98 (dd, J=7.9, 2.1 Hz, 1H), 7.57-7.60 (m, 2H), 7.24-7.28 (m, 2H), 7.11 (dd, J=11.3, 8.4 Hz, 1H), 6.80-6.83 (m, 1H), 6.71 (d, J=5.3 Hz, 1H), 4.59 (t, J=5.6 Hz, 1H), 3.60 (dq, J=9.4, 7.0 Hz, 2H), 3.46 (dq, J=9.4, 7.0 Hz, 2H), 3.32-3.36 (m, 2H), 2.28 (s, 3H), 1.81-1.85 (m, 2H), 1.12 (t, J=7.0 Hz, 6H)

LR MS (ES+): 589 (M+Na$^+$)
LR MS (ES−): 565 (M−H)

Example 22

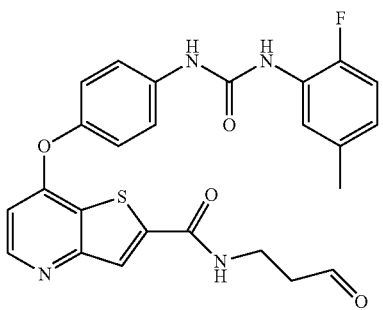 [SMILES: Cc1ccc(F)c(NC(=O)Nc2ccc(Oc3ccnc4cc(C(=O)NCCC=O)sc34)cc2)c1]

7-[4-({[(2-fluoro-5-methylphenyl)amino]carbonyl}amino)phenoxy]-N-(3-oxopropyl)thieno[3,2-b]pyridine-2-carboxamide to a stirred solution of N-(3,3-diethoxypropyl)-7-[4-({[(2-fluoro-5-methylphenyl)amino]carbonyl}amino)phenoxy]thieno[3,2-b]pyridine-2-carboxamide (680 mg, 1.20 mmol) in 10 ml of THF was added 1 ml of 2M HCl. The mixture was stirred at room temperature for 3 hours, and poured into 100 ml of water with vigorous stirring. Saturated NaHCO$_3$ solution was added until pH=9. The precipitates were filtered, washed with water and dried in vacuo to give 7-[4-({[(2-fluoro-5-methylphenyl)amino]carbonyl}amino)phenoxy]-N-(3-oxopropyl)thieno[3,2-b]pyridine-2-carboxamide as brown solid. Yield: 550 mg, 93%.

LR MS (ES+): 515 (M+Na$^+$)
LR MS (ES−): 491 (M−H)

Example 23

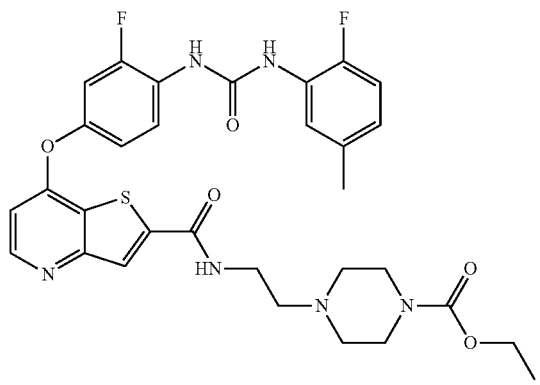 [SMILES: CCOC(=O)N1CCN(CCNC(=O)c2cc3nccc(Oc4ccc(NC(=O)Nc5cc(C)ccc5F)c(F)c4)c3s2)CC1]

ethyl 4-{2-[({7-[3-fluoro-4-({[(2-fluoro-5-methylphenyl)amino]carbonyl}amino)phenoxy]thieno[3,2-b]pyridin-2-yl}carbonyl)amino]ethyl}piperazine-1-carboxylate $^1$H NMR (DMSO-$d_6$) d: 9.13 (d, J=2.6 Hz, 1H), 8.99 (d, J=2.6 Hz, 1H), 8.92 (t, J=5.9 Hz, 1H), 8.59 (d, J=5.6 Hz, 1H), 8.29 (t, J=9.1 Hz, 1H), 8.24 (s, 1H), 8.01 (dd, J=7.8, 2.2 Hz, 1H), 7.42 (dd, J=11.7, 2.6 Hz, 1H), 7.12-7.16 (m, 1H), 7.12 (dd, J=11.4, 8.5 Hz, 1H), 6.80-6.85 (m, 1H), 6.80 (d, J=5.6 Hz, 1H), 4.03 (q, J=7.0 Hz, 2H), 3.43 (q, J=6.5 Hz, 2H), 3.36 (t, J=5.0 Hz, 4H), 2.51-2.56 (m, 2H), 2.39-2.44 (m, 4H), 2.28 (s, 3H), 1.17 (t, J=7.0 Hz, 3H)

LR MS (ES+): 639 (MH+)
LR MS (ES−): 637 (M−H)

The following Example 24 was prepared using the experiment procedure described in Example 38, but with the appropriate reagent, reaction conditions and reactant substitutions that will be readily realized by those of ordinary skill in this art without the exercise of undue experimentation.

Example 24

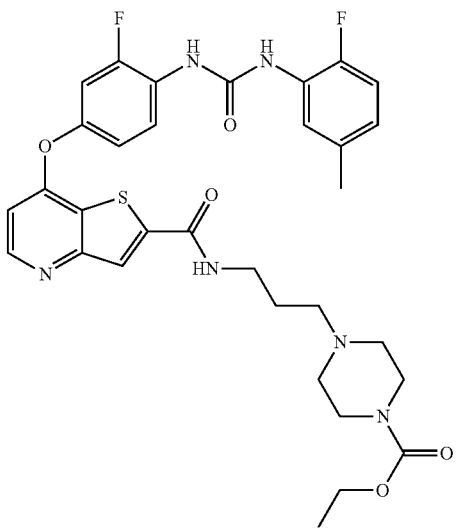 [SMILES: CCOC(=O)N1CCN(CCCNC(=O)c2cc3nccc(Oc4ccc(NC(=O)Nc5cc(C)ccc5F)c(F)c4)c3s2)CC1]

ethyl 4-{3-[({7-[3-fluoro-4-({[(2-fluoro-5-methyl-phenyl)amino]carbonyl}amino)phenoxy]thieno[3,2-b]pyridin-2-yl carbonyl]amino]propyl}piperazine-1-carboxylate $^1$H NMR (DMSO-d$_6$) δ: 9.13 (d, J=2.6 Hz, 1H), 8.99 (d, J=2.6 Hz, 1H), 8.94 (t, J=5.6 Hz, 1H), 8.59 (d, J=5.3 Hz, 1H), 8.29 (t, J=9.2 Hz, 1H), 8.24 (s, 1H), 8.01 (dd, J=7.9, 2.3 Hz, 1H), 7.42 (dd, J=11.7, 2.6 Hz, 1H), 7.09-7.16 (m, 2H), 6.79-6.85 (m, 1H), 6.80 (d, J=5.3 Hz, 1H), 4.02 (q, J=7.0 Hz, 2H), 3.32-3.38 (m, 6H), 2.31-2.40 (m, 6H), 2.28 (s, 3H), 1.73 (quin, J=6.9 Hz, 2H), 1.17 (t, J=7.2 Hz, 3H)

LR MS (ES+): 653 (MH$^+$)
LR MS (ES−): 651 (M−H)

Example 25

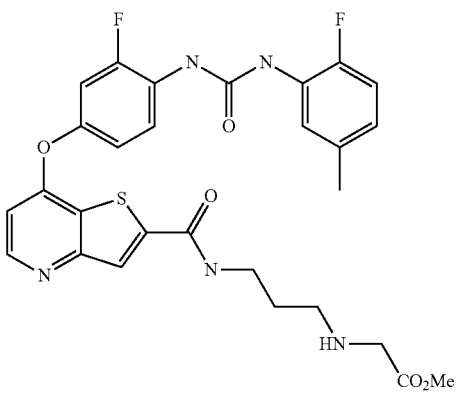 [SMILES: COC(=O)CNCCCNC(=O)c1cc2nccc(Oc3ccc(NC(=O)Nc4cc(C)ccc4F)c(F)c3)c2s1]

methyl ({3-[({7-[3-fluoro-4-({[(2-fluoro-5-methylphenyl)amino]carbonyl}amino)phenoxy]thieno[3,2-b]pyridin-2-yl}carbonyl)amino]propyl}amino)acetate To a stirred solution of N-(3-aminopropyl)-7-[3-fluoro-4-({[(2-fluoro-5-methylphenyl)amino]carbonyl}amino)phenoxy]thieno[3,2-b]pyridine-2-carboxamide (125 mg, 0.24 mmol) and N,N-diisopropylethylamine (46 mg, 0.36 mmol) in 10 ml of anhydrous DMF was added methyl bromoacetate (36 mg, 0.24 mmol). The mixture was stirred at room temperature for 50 minutes and poured into 100 ml of water with vigorous stirring. The precipitates were filtered and dried in vacuo to give the crude, which was purified by silica gel chromatography eluting with 5~8% of MeOH in CHCl$_3$ to afford methyl ({3-[({7-[3-fluoro-4-({[(2-fluoro-5-methylphenyl)amino]carbonyl}amino)phenoxy]thieno[3,2-b]pyridin-2-yl}carbonyl)amino]propyl}amino)acetate as light beige solid. Yield: 54 mg, 38%.

$^1$H NMR (DMSO-d$_6$): 9.10 (d, J=1.8 Hz, 1H), 8.96 (d, J=2.6 Hz, 1H), 8.93 (t, J=5.6 Hz, 1H), 8.56 (d, J=5.6 Hz, 1H), 8.26 (t, J=9.1 Hz, 1H), 8.20 (s, 1H), 7.98 (dd, J=7.9, 2.1 Hz, 1H), 7.39 (dd, J=11.7, 2.9 Hz, 1H), 7.11 (dd, J=9.0, 2.5 Hz, 1H), 7.09 (dd, J=11.4, 8.2 Hz, 1H), 6.78-6.81 (m, 1H), 6.77 (d, J=5.3 Hz, 1H), 3.59 (s, 3H), 3.32 (s, 2H), 3.29-3.34 (m, 2H), 2.56 (t, J=6.7 Hz, 2H), 2.25 (s, 3H), 1.65 (quin, J=7.0 Hz, 2H)

LR MS (ES+): 584 (MH+)
LR MS (ES−): 582 (M−H)

Example 26

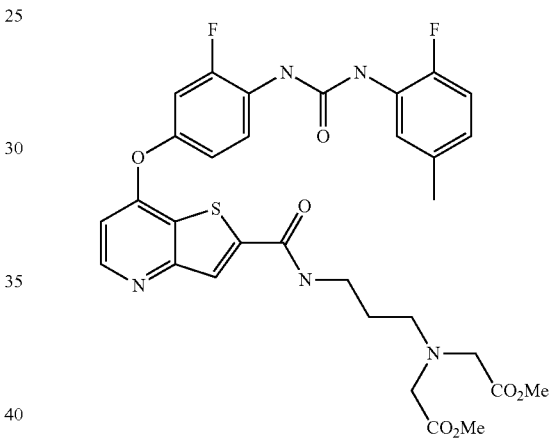

dimethyl 2,2'-({3-[({7-[3-fluoro-4-({[(2-fluoro-5-methylphenyl)amino]carbonyl}amino)phenoxy]thieno[3,2-b]pyridin-2-yl}carbonyl)amino]propyl}imino)diacetate To a stirred solution of N-(3-aminopropyl)-7-[3-fluoro-4-({[(2-fluoro-5-methylphenyl)amino]carbonyl}amino)phenoxy]thieno[3,2-b]pyridine-2-carboxamide (125 mg, 0.24 mmol) and N,N-diisopropylethylamine (77 mg, 0.60 mmol) in 10 ml of anhydrous DMF was added methyl bromoacetate (92 mg, 0.60 mmol). The mixture was heated at 60° C. for 1 hour and poured into 100 ml of water with vigorous stirring. The precipitates were filtered and dried in vacuo to give the crude, which was purified by silica gel chromatography eluting with 3~4% of MeOH in CHCl$_3$ to afford dimethyl 2,2'-({3-[({7-[3-fluoro-4-({[(2-fluoro-5-methylphenyl)amino]carbonyl}amino)phenoxy]thieno[3,2-b]pyridin-2-yl}carbonyl)amino]propyl}imino)diacetate as white solid. Yield: 140 mg, 88%.

$^1$H NMR (DMSO-d$_6$): 9.10 (d, J=2.1 Hz, 1H), 8.96 (d, J=2.1 Hz, 1H), 8.86 (t, J=5.6 Hz, 1H), 8.56 (d, J=5.3 Hz, 1H), 8.26 (t, J=9.1 Hz, 1H), 8.20 (s, 1H), 7.98 (dd, J=7.8, 2.5 Hz, 1H), 7.39 (dd, J=11.6, 2.8 Hz, 1H), 7.11 (dd, J=9.2, 2.8 Hz, 1H), 7.09 (dd, J=11.3, 8.4 Hz, 1H), 6.78-6.82 (m, 1H), 6.77 (d, J=5.6 Hz, 1H), 3.58 (s, 6H), 3.51 (s, 4H), 3.29-3.33 (m, 2H), 2.69 (t, J=6.9 Hz, 2H), 2.25 (s, 3H), 1.64 (quin, J=7.0 Hz, 2H)

LR MS (ES+): 677 (MNa+)
LR MS (ES−): 654 (M−H)

The following Example 27 was prepared using the experiment procedure described in Example 26, but with the appropriate reagent, reaction conditions and reactant substitutions that will be readily realized by those of ordinary skill in this art without the exercise of undue experimentation.

Example 27

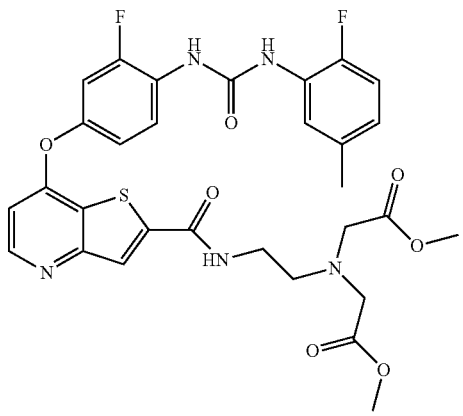 [SMILES: COC(=O)CN(CCNC(=O)c1cc2nccc(Oc3ccc(NC(=O)Nc4cc(C)ccc4F)c(F)c3)c2s1)CC(=O)OC]

dimethyl 2,2'-({2-[({7-[3-fluoro-4-({[(2-fluoro-5-methylphenyl)amino]carbonyl}amino)phenoxy]thieno[3,2-b]pyridin-2-yl}carbonyl)amino]ethyl}imino)diacetate $^1$H NMR (acetone) d: 8.59 (d, J=5.3 Hz, 1H), 8.56 (br. s., 1H), 8.46 (t, J=9.1 Hz, 1H), 8.42 (d, J=2.9 Hz, 1H), 8.40 (t, J=5.0 Hz, 1H), 8.15-8.18 (m, 1H), 8.15 (s, 1H), 7.25 (dd, J=11.6, 2.8 Hz, 1H), 7.13-7.17 (m, 1H), 7.02 (dd, J=11.3, 8.4 Hz, 1H), 6.81-6.86 (m, 1H), 6.78 (d, J=5.3 Hz, 1H), 3.69 (s, 6H), 3.68 (s, 4H), 3.42-3.48 (m, 2H), 3.00 (t, J=5.9 Hz, 2H), 2.32 (s, 3H)

LR MS (ES+): 642 (MH+)
LR MS (ES−): 640 (M−H)

The following Example 28 was prepared using the experiment procedure described in Example 30, but with the appropriate reagent, reaction conditions and reactant substitutions that will be readily realized by those of ordinary skill in this art without the exercise of undue experimentation.

Example 28

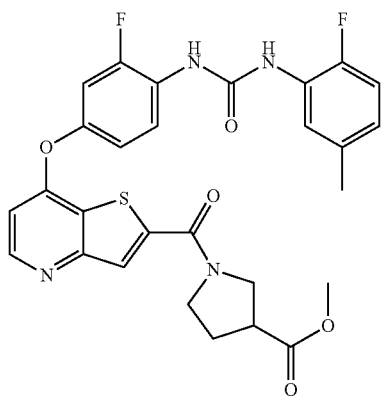 [SMILES: COC(=O)C1CCN(C(=O)c2cc3nccc(Oc4ccc(NC(=O)Nc5cc(C)ccc5F)c(F)c4)c3s2)C1]

methyl 1-({7-[3-fluoro-4-({[(2-fluoro-5-methylphenyl)amino]carbonyl}amino)phenoxy]thieno[3,2-b]pyridin-2-yl}carbonyl)pyrrolidine-3-carboxylate

LR MS (ES+): 567 (MH+)
LR MS (ES−): 565 (M−H)

Example 29

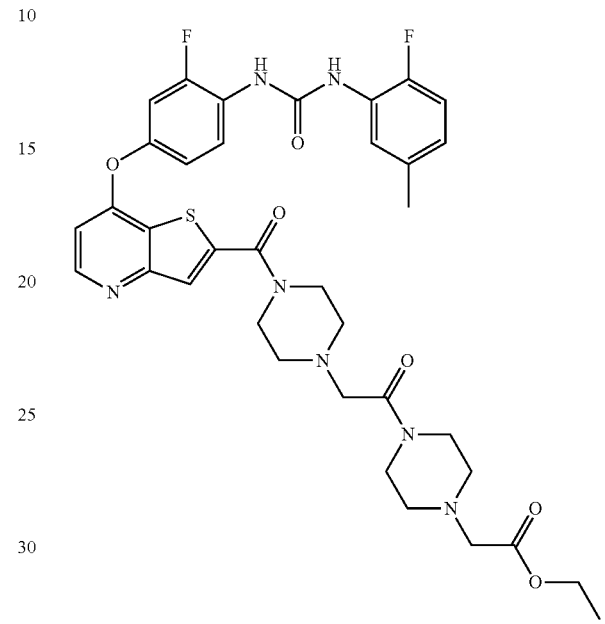

ethyl (4-([4-({7-[3-fluoro-4-({[(2-fluoro-5-methylphenyl)amino]carbonyl}amino)phenoxy]thieno[3,2-b]pyridin-2-yl}carbonyl)piperazin-1-yl]acetyl}piperazin-1-yl)acetate The title compound was isolated as a side product in the preparation of ethyl [4-({7-[3-fluoro-4-({[(2-fluoro-5-methylphenyl)amino]carbonyl}amino)phenoxy]thieno[3,2-b]pyridin-2-yl}carbonyl)piperazin-1-yl]acetate.

LR MS (ES+): 736 (MH+)
LR MS (ES−): 734 (M−H)

Example 30

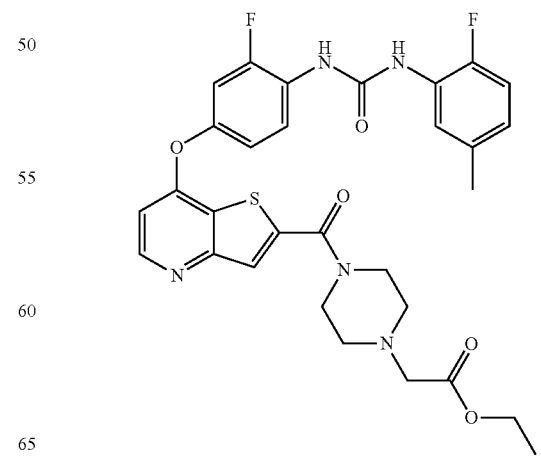

ethyl [4-({7-[3-fluoro-4-({[(2-fluoro-5-methylphenyl)amino]carbonyl}amino)phenoxy]thieno[3,2-b]pyridin-2-yl}carbonyl)piperazin-1-yl]acetate a mixture of 7-[3-fluoro-4-({[(2-fluoro-5-methylphenyl)amino]carbonyl}amino)phenoxy]thieno[3,2-b]pyridine-2-carboxylic acid (100 mg, 0.22 mmol), HATU (91 mg, 0.24 mmol) and N,N-diisopropylethylamine (62 mg, 0.48 mmol) in anhydrous tetrahydrofuran (10 ml) was heated at 60° C. for 10 minutes, followed by addition of ethyl piperazinoacetate (57 mg, 0.33 mmol). Heating was continued at 60° C. for 30 minutes and the mixture was poured into 100 ml of water. The precipitates were filtered, washed with water and dried in vacuo to give the crude, which was purified by silica gel chromatography eluting with 3~5% methanol in chloroform to give ethyl [4-({7-[3-fluoro-4-({[(2-fluoro-5-methylphenyl)amino]carbonyl}amino)phenoxy]thieno[3,2-b]pyridin-2-yl}carbonyl)piperazin-1-yl]acetate as white solid. Yield: 73 mg, 54%.

$^1$H NMR (DMSO-$d_6$) δ: 9.11 (br. s., 1H), 8.97 (br. s., 1H), 8.56 (d, J=5.6 Hz, 1H), 8.26 (t, J=9.1 Hz, 1H), 7.98 (d, J=8.5 Hz, 1H), 7.80 (s, 1H), 7.39 (dd, J=11.7, 2.3 Hz, 1H), 7.06-7.13 (m, 2H), 6.78-6.81 (m, 1H), 6.77 (d, J=5.3 Hz, 1H), 4.06 (q, J=7.0 Hz, 2H), 3.66 (br. s., 4H), 3.27 (s, 2H), 2.58 (br. s., 4H), 2.25 (s, 3H), 1.16 (t, J=7.2 Hz, 3H)

LR MS (ES+): 610 (MH$^+$)

LR MS (ES−): 608 (M−H)

The following Example 31 was prepared using the experiment procedure described in Example 25, but with the appropriate reagent, reaction conditions and reactant substitutions that will be readily realized by those of ordinary skill in this art without the exercise of undue experimentation.

Example 31

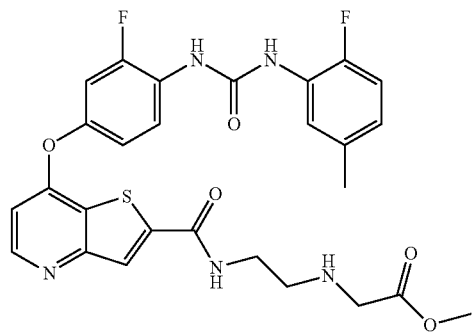 [SMILES: COC(=O)CNCCNC(=O)c1cc2nccc(Oc3ccc(NC(=O)Nc4cc(C)ccc4F)c(F)c3)c2s1]

methyl ({2-[({7-[3-fluoro-4-({[(2-fluoro-5-methylphenyl)amino]carbonyl}amino)phenoxy]thieno[3,2-b]pyridin-2-yl}carbonyl)amino]ethyl}amino)acetate $^1$H NMR (DMSO-$d_6$): 9.10 (s, 1H), 8.96 (s, 1H), 8.89 (t, J=5.7 Hz, 1H), 8.56 (d, J=5.6 Hz, 1H), 8.25 (t, J=9.1 Hz, 1H), 8.22 (s, 1H), 7.98 (d, J=8.2 Hz, 1H), 7.39 (dd, J=11.7, 2.3 Hz, 1H), 7.10-7.13 (m, 1H), 7.09 (dd, J=11.3, 8.4 Hz, 1H), 6.78-6.82 (m, 1H), 6.77 (d, J=5.3 Hz, 1H), 3.59 (s, 3H), 3.36 (s, 2H), 3.31-3.35 (m, 2H), 2.70 (t, J=6.5 Hz, 2H), 2.25 (s, 3H)

LR MS (ES+): 570 (MH+)

Example 32

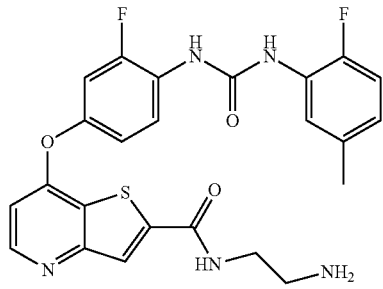 [SMILES: Cc1ccc(F)c(NC(=O)Nc2ccc(Oc3ccnc4cc(C(=O)NCCN)sc34)cc2F)c1]

N-(2-aminoethyl)-7-[3-fluoro-4-({[(2-fluoro-5-methylphenyl)amino]carbonyl}amino)phenoxy]thieno[3,2-b]pyridine-2-carboxamide To a stirred suspension of tert-butyl {2-[({7-[3-fluoro-4-({[(2-fluoro-5-methylphenyl)amino]carbonyl}amino)phenoxy]thieno[3,2-b]pyridin-2-yl}carbonyl)amino]ethyl}carbamate (488 mg, 0.82 mmol) in 10 ml of dichloromethane was added 5 ml of trifluoroacetic acid. The mixture was stirred at room temperature for one hour and evaporated to dryness under reduced pressure. The residue was re-dissolved in MeOH (5 ml) and poured into 100 ml of water with vigorous stirring. Saturated NaHCO$_3$ solution was added until pH=8~9. The precipitates were filtered, washed with water and dried in vacuo to give N-(2-aminoethyl)-7-[3-fluoro-4-({[(2-fluoro-5-methylphenyl)amino]carbonyl}amino)phenoxy]thieno[3,2-b]pyridine-2-carboxamide as brown solid. Yield: 400 mg, 99%.

LR MS (ES+): 498 (MH$^+$)

LR MS (ES−): 496 (M−H)

Example 33

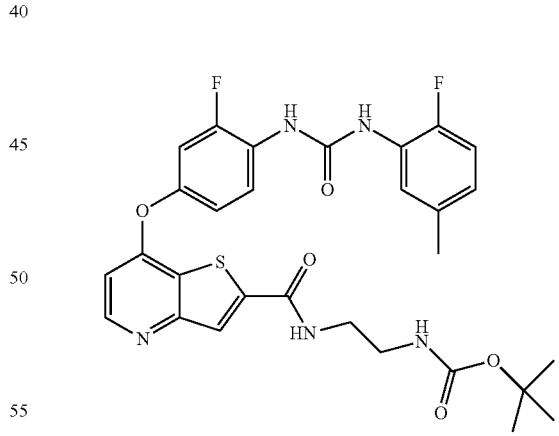

tert-butyl (2-[({7-[3-fluoro-4-({[(2-fluoro-5-methylphenyl)amino]carbonyl}amino)phenoxy]thieno[3,2-b]pyridin-2-yl}carbonyl)amino]ethylcarbamate a mixture of 7-[3-fluoro-4-({[(2-fluoro-5-methylphenyl)amino]carbonyl}amino)phenoxy]thieno[3,2-b]pyridine-2-carboxylic acid (400 mg, 0.88 mmol), HATU (400 mg, 1.05 mmol) and N,N-diisopropylethylamine (250 mg, 1.94 mmol) in anhydrous THF (10 ml) was heated at 60° C. for 15 minutes, followed by addition of N-Boc-ethylenediamine (210 mg, 1.32 mmol). The mixture was stirred at 60° C. for another 5 minutes, cooled to room temperature and poured into 100 ml of water with vigorous stirring. 2M HCl was added dropwise until pH=5. The precipitates were filtered, washed with water and dried in vacuo to give tert-butyl {2-[({7-[3-fluoro-4-({[(2-fluoro-5-methylphenyl)amino] carbonyl}amino)phenoxy]thieno[3,2-b]pyridin-2-yl}carbonyl)amino]ethyl}carbamate as off-white solid. Yield: 518 mg, 99%.

$^1$H NMR (DMSO-d$_6$) δ: 9.12 (d, J=1.8 Hz, 1H), 8.99 (d, J=2.1 Hz, 1H), 8.95 (t, J=5.9 Hz, 1H), 8.59 (d, J=5.3 Hz, 1H), 8.28 (t, J=9.1 Hz, 1H), 8.22 (s, 1H), 8.01 (dd, J=7.8, 2.2 Hz, 1H), 7.42 (dd, J=11.7, 2.6 Hz, 1H), 7.10-7.15 (m, 2H), 6.95 (t, J=6.0 Hz, 1H), 6.81-6.84 (m, 1H), 6.80 (d, J=5.6 Hz, 1H), 3.31-3.34 (m, 2H), 3.14 (q, J=6.6 Hz, 2H), 2.28 (s, 3H), 1.37 (s, 9H)

LR MS (ES+): 598 (MH$^+$)

LR MS (ES−): 596 (M−H)

Example 34

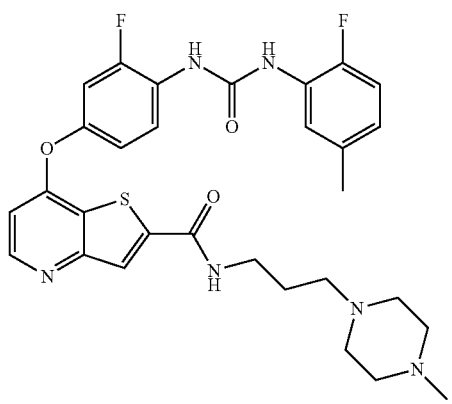 [SMILES: Cc1ccc(F)c(NC(=O)Nc2ccc(Oc3ccnc4cc(C(=O)NCCCN5CCN(C)CC5)sc34)cc2F)c1]

7-[3-fluoro-4-({[(2-fluoro-5-methylphenyl)amino] carbonyl}amino)phenoxy]-N-[3-(4-methylpiperazin-1-yl) propyl]thieno[3,2-b]pyridine-2-carboxamide a mixture of 7-[3-fluoro-4-({[(2-fluoro-5-methylphenyl)amino] carbonyl}amino)phenoxy]thieno[3,2-b]pyridine-2-carboxylic acid (100 mg, 0.22 mmol), HATU (90 mg, 0.24 mmol) and N,N-diisopropylethylamine (55 mg, 0.43 mmol) in anhydrous acetonitrile (10 ml) was stirred at room temperature for 30 minutes, followed by addition of 3-(4-methylpiperazin-1-yl)propan-1-amine (40 mg, 0.25 mmol). The mixture was stirred for another 10 minutes and poured into 100 ml of water. The precipitates were filtered, washed with water and dried in vacuo to give 7-[3-fluoro-4-({[(2-fluoro-5-methylphenyl)amino]carbonyl}amino)phenoxy]-N-[3-(4-methylpiperazin-1-yl)propyl]thieno[3,2-b]pyridine-2-carboxamide as brown solid. Yield: 110 mg, 84%.

$^1$H NMR (acetone): 8.56-8.60 (m, 2H), 8.42-8.49 (m, 3H), 8.14-8.18 (m, 1H), 8.06 (s, 1H), 7.24 (dd, J=11.6, 2.8 Hz, 1H), 7.14 (dt, J=8.9, 2.0 Hz, 1H), 7.02 (dd, J=11.3, 8.4 Hz, 1H), 6.81-6.86 (m, 1H), 6.78 (d, J=5.3 Hz, 1H), 3.49 (q, J=6.5 Hz, 2H), 2.48 (t, J=6.5 Hz, 2H), 2.39 (br. s., 8H), 2.32 (s, 3H), 2.18 (s, 3H), 1.80 (quin, J=6.6 Hz, 2H)

LR MS (ES+): 595 (MH$^+$)

LR MS (ES−): 593 (M−H)

Example 35

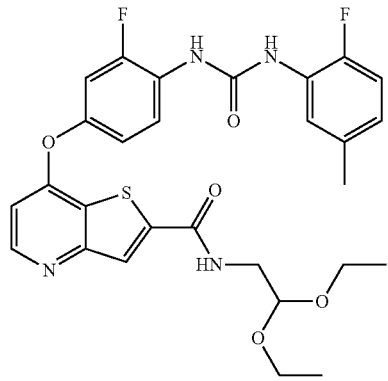 [SMILES: CCOC(CNC(=O)c1cc2nccc(Oc3ccc(NC(=O)Nc4cc(C)ccc4F)c(F)c3)c2s1)OCC]

N-(2,2-diethoxyethyl)-7-[3-fluoro-4-({[(2-fluoro-5-methylphenyl)amino]carbonyl}amino)phenoxy] thieno[3,2-b]pyridine-2-carboxamide The following Examples 36 and 37 were prepared using the experiment procedure described in Example 38, but with the appropriate reagent, reaction conditions and reactant substitutions that will be readily realized by those of ordinary skill in this art without the exercise of undue experimentation.

Example 36

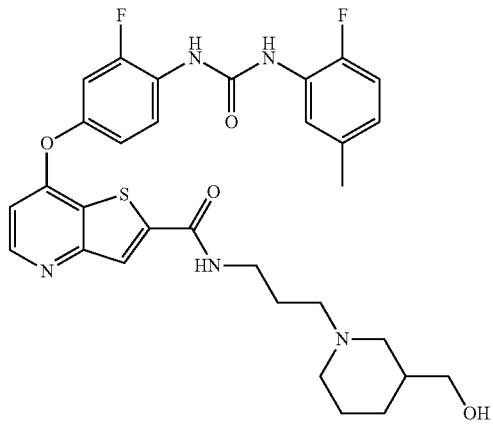

7-[3-fluoro-4-({[(2-fluoro-5-methylphenyl)amino] carbonyl}amino)phenoxy]-N-{3-[3-(hydroxymethyl) piperidin-1-yl]propyl}thieno[3,2-b]pyridine-2-carboxamide

LR MS (ES+): 610 (MH+)

LR MS (ES−): 608 (M−H)

Example 37

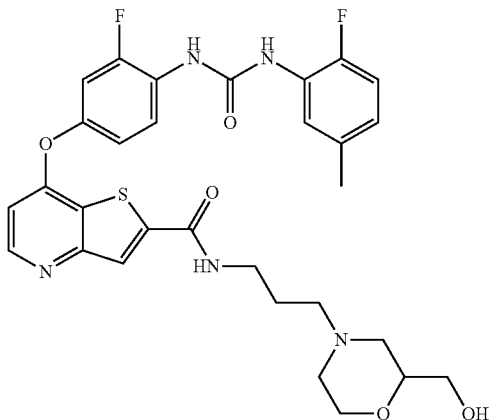 [SMILES: Cc1ccc(F)c(NC(=O)Nc2ccc(Oc3ccnc4cc(C(=O)NCCCN5CCOC(CO)C5)sc34)cc2F)c1]

7-[3-fluoro-4-({[(2-fluoro-5-methylphenyl)amino]carbonyl}amino)phenoxy]-N-{3-[2-(hydroxymethyl)morpholin-4-yl]propyl}thieno[3,2-b]pyridine-2-carboxamide

LR MS (ES+): 612 (MH+)
LR MS (ES−): 610 (M−H)

Example 38

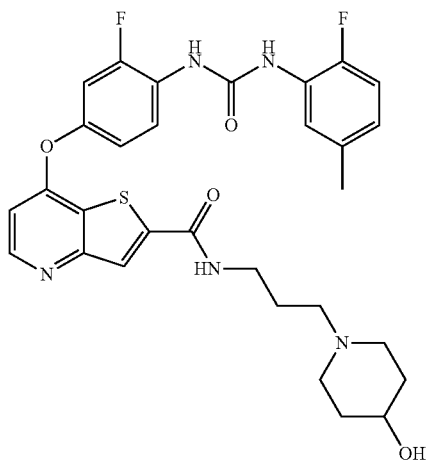 [SMILES: Cc1ccc(F)c(NC(=O)Nc2ccc(Oc3ccnc4cc(C(=O)NCCCN5CCC(O)CC5)sc34)cc2F)c1]

7-[3-fluoro-4-({[(2-fluoro-5-methylphenyl)amino]carbonyl}amino)phenoxy]-N-[3-(4-hydroxypiperidin-1-yl)propyl]thieno[3,2-b]pyridine-2-carboxamide to a stirred solution of 7-[3-fluoro-4-({[(2-fluoro-5-methylphenyl)amino]carbonyl}amino)phenoxy]-N-(3-oxopropyl)thieno[3,2-b]pyridine-2-carboxamide (150 mg, 0.29 mmol) in 10 ml of anhydrous DMF were added 4-hydroxypiperidine (59 mg, 0.58 mmol) and acetic acid (10 mg, 0.17 mmol). The mixture was stirred at room temperature for 40 minutes, followed by addition of 1M sodium cyanoborohydride solution in THF (0.60 ml, 0.60 mmol) and stirring was continued for another 30 minutes. The mixture was poured into 100 ml of water. The precipitates were filtered, washed with water and dried to give the crude, which was purified by silica gel flash chromatography eluting with 10-20% of MeOH in $CHCl_3$ to give 7-[3-fluoro-4-({[(2-fluoro-5-methylphenyl)amino]carbonyl}amino)phenoxy]-N-[3-(4-hydroxypiperidin-1-yl)propyl]thieno[3,2-b]pyridine-2-carboxamide as white solid. Yield: 70 mg, 40%.

$^1$H NMR (DMSO-$d_6$): 9.11 (s, 1H), 8.97 (s, 1H), 8.94 (br. s., 1H), 8.56 (d, J=5.3 Hz, 1H), 8.25 (t, J=9.1 Hz, 1H), 8.21 (s, 1H), 7.98 (d, J=7.6 Hz, 1H), 7.39 (dd, J=11.7, 2.6 Hz, 1H), 7.06-7.14 (m, 2H), 6.79 (td, J=5.3, 2.3 Hz, 1H), 6.77 (d, J=5.3 Hz, 1H), 4.56 (br. s., 1H), 3.44 (br. s., 1H), 3.36 (br. s., 2H), 2.76 (br. s., 2H), 2.28-2.45 (m, 2H), 2.25 (s, 3H), 2.05 (br. s., 2H), 1.71 (br. s., 4H), 1.39 (br. s., 2H)

LR MS (ES+): 596 (MH+)
LR MS (ES−): 594 (M−H)

The following Example 39 was prepared using the experiment procedure described in Example 42, but with the appropriate reagent, reaction conditions and reactant substitutions that will be readily realized by those of ordinary skill in this art without the exercise of undue experimentation.

Example 39

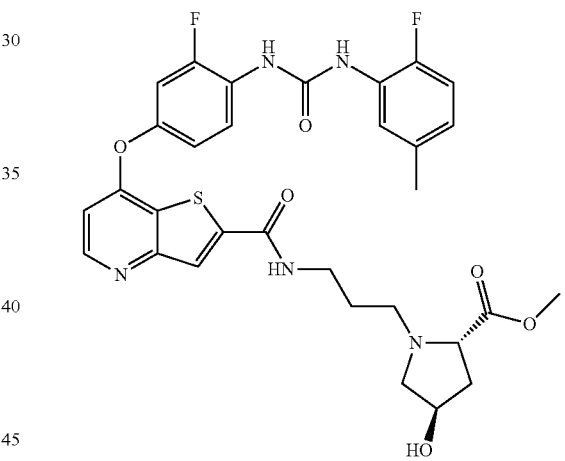

methyl (2S,4R)-1-{3-[({7-[3-fluoro-4-({[(2-fluoro-5-methylphenyl)amino]carbonyl}amino)phenoxy]thieno[3,2-b]pyridin-2-yl}carbonyl)amino]propyl}-4-hydroxypyrrolidine-2-carboxylate $^1$H NMR (acetone): 8.66 (t, J=6.2 Hz, 1H), 8.57 (d, J=5.3 Hz, 1H), 8.56 (d, J=2.1 Hz, 1H), 8.45 (t, J=9.1 Hz, 1H), 8.42 (d, J=2.3 Hz, 1H), 8.14-8.17 (m, 1H), 8.08 (s, 1H), 7.24 (dd, J=11.6, 2.8 Hz, 1H), 7.14 (dt, J=9.1, 1.6 Hz, 1H), 7.02 (dd, J=11.3, 8.4 Hz, 1H), 6.81-6.85 (m, 1H), 6.78 (d, J=5.3 Hz, 1H), 4.35-4.44 (m, 1H), 4.05 (d, J=4.1 Hz, 1H), 3.72 (s, 3H), 3.59-3.67 (m, 1H), 3.56 (t, J=8.2 Hz, 1H), 3.39-3.52 (m, 2H), 2.87-2.94 (m, 1H), 2.66 (dt, J=12.5, 4.7 Hz, 1H), 2.38 (dd, J=10.0, 4.1 Hz, 1H), 2.32 (s, 3H), 2.07-2.14 (m, 2H), 1.74-1.83 (m, 1H), 1.65-1.74 (m, 1H)

LR MS (ES+): 640 (MH$^+$)
LR MS (ES−): 638 (M−H)

Example 40

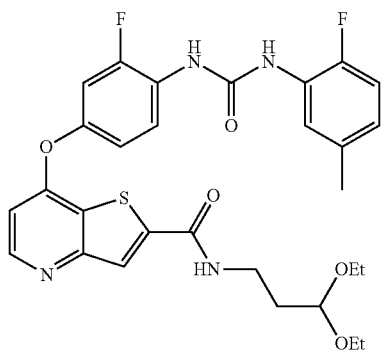 [SMILES: CCOC(CCNC(=O)c1cc2nccc(Oc3ccc(NC(=O)Nc4cc(C)ccc4F)c(F)c3)c2s1)OCC]

N-(3,3-diethoxypropyl)-7-[3-fluoro-4-({[(2-fluoro-5-methylphenyl)amino]carbonyl}amino)phenoxy]thieno[3,2-b]pyridine-2-carboxamide To a stirred suspension of 7-[3-fluoro-4-({[(2-fluoro-5-methylphenyl)amino]carbonyl}amino)phenoxy]thieno[3,2-b]pyridine-2-carboxylic acid (1.0 g, 2.2 mmol) in 20 ml of anhydrous tetrahydrofuran were added HATU (1.0 g, 2.6 mmol) and N,N-diisopropylethylamine (620 mg, 4.8 mmol). The mixture was heated at 60° C. for 20 minutes, followed by addition of 1-amino-3,3-diethoxypropane (388 mg, 2.6 mmol). The mixture was heated at 60° C. for another 30 minutes, cooled to room temperature and poured into 100 ml of water with vigorous stirring. The precipitates were filtered, washed with water and dried in vacuo to give N-(3,3-diethoxypropyl)-7-[3-fluoro-4-({[(2-fluoro-5-methylphenyl)amino]carbonyl}amino)phenoxy]thieno[3,2-b]pyridine-2-carboxamide as off-white solid. Yield: 1.23 g, 95%.

$^1$H NMR (DMSO-d$_6$): 9.10 (d, J=2.6 Hz, 1H), 8.96 (d, J=2.6 Hz, 1H), 8.89 (t, J=5.6 Hz, 1H), 8.56 (d, J=5.3 Hz, 1H), 8.26 (t, J=9.1 Hz, 1H), 8.20 (s, 1H), 7.98 (dd, J=7.9, 2.3 Hz, 1H), 7.39 (dd, J=11.7, 2.6 Hz, 1H), 7.10-7.13 (m, 1H), 7.09 (dd, J=11.3, 8.4 Hz, 1H), 6.78-6.82 (m, 1H), 6.77 (d, J=5.6 Hz, 1H), 4.56 (t, J=5.6 Hz, 1H), 3.57 (dq, J=9.4, 7.0 Hz, 2H), 3.43 (dq, J=9.7, 7.0 Hz, 2H), 3.29-3.34 (m, 2H), 2.25 (s, 3H), 1.75-1.85 (m, 2H), 1.09 (t, J=7.0 Hz, 6H)

LR MS (ES+): 607 (MNa+)
LR MS (ES−): 583 (M−H)

Example 41

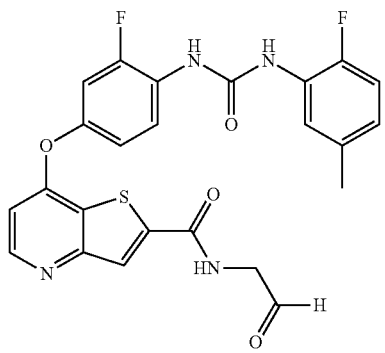 [SMILES: Cc1ccc(F)c(NC(=O)Nc2ccc(Oc3ccnc4cc(C(=O)NCC=O)sc34)cc2F)c1]

7-[3-fluoro-4-({[(2-fluoro-5-methylphenyl)amino]carbonyl}amino)phenoxy]-N-(2-oxoethyl)thieno[3,2-b]pyridine-2-carboxamide to a stirred solution of N-(2,2-diethoxyethyl)-7-[3-fluoro-4-({[(2-fluoro-5-methylphenyl)amino]carbonyl}amino)phenoxy]thieno[3,2-b]pyridine-2-carboxamide (300 mg, 0.53 mmol) in 10 ml of THF was added 2 ml of 2M HCl. The mixture was heated under nitrogen at 60° C. for 4 hours, cooled to room temperature, and poured into 100 ml of water with vigorous stirring. Saturated NaHCO$_3$ solution was added until pH=7. The precipitates were filtered, washed with water and dried in vacuo to give 7-[3-fluoro-4-({[(2-fluoro-5-methylphenyl)amino]carbonyl}amino)phenoxy]-N-(2-oxoethyl)thieno[3,2-b]pyridine-2-carboxamide as white solid. Yield: 250 mg, 96%.

LR MS (ES+): 497 (MH+)
LR MS (ES−): 495 (M−H)

Example 42

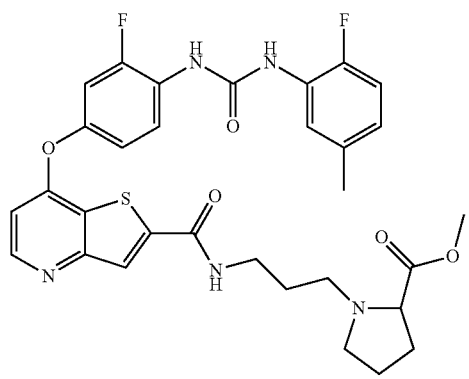 [SMILES: COC(=O)C1CCCN1CCCNC(=O)c1cc2nccc(Oc3ccc(NC(=O)Nc4cc(C)ccc4F)c(F)c3)c2s1]

methyl 1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-2-carboxylate to a stirred solution of 7-[3-fluoro-4-({[(2-fluoro-5-methylphenyl)amino]carbonyl}amino)phenoxy]-N-(3-oxopropyl)thieno[3,2-b]pyridine-2-carboxamide (150 mg, 0.29 mmol) in 10 ml of anhydrous DMF was added L-proline methyl ester hydrochloride (96 mg, 0.58 mmol) and triethylamine (58 mg, 0.58 mmol). The mixture was stirred at room temperature under nitrogen for one hour, and 1M solution of sodium cyanoborohydride in THF (0.60 ml, 0.60 mmol) was added. The mixture was stirred for another hour, and poured into 100 ml of water. The precipitates were filtered, washed with water and dried in vacuo to give the crude product, which was purified by silica gel chromatography eluting with 2~3% of methanol in chloroform to afford methyl 1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-2-carboxylate as white solid. Yield: 90 mg, 50%.

$^1$H NMR (DMSO-d$_6$): 9.10 (s, 1H), 8.96 (s, 1H), 8.92 (t, J=5.7 Hz, 1H), 8.56 (d, J=5.3 Hz, 1H), 8.26 (t, J=9.1 Hz, 1H), 8.18 (s, 1H), 7.95-8.01 (m, 1H), 7.39 (dd, J=11.7, 2.6 Hz, 1H), 7.06-7.13 (m, 2H), 6.78-6.82 (m, 1H), 6.77 (d, J=5.9 Hz, 1H), 3.58 (s, 3H), 3.29-3.34 (m, 2H), 3.15-3.21 (m, 1H), 2.97-3.05 (m, 1H), 2.67 (dt, J=11.9, 7.6 Hz, 1H), 2.40-2.45 (m, 1H), 2.29-2.38 (m, 1H), 2.25 (s, 3H), 2.02 (dq, J=12.0, 8.2 Hz, 1H), 1.76-1.81 (m, 1H), 1.70-1.76 (m, 2H), 1.60-1.70 (m, 2H)

LR MS (ES+): 624 (MH$^+$)
LR MS (ES−): 622 (M−H)

The following Example 43 was prepared using the experiment procedure described in Example 34, but with the appropriate reagent, reaction conditions and reactant substitutions that will be readily realized by those of ordinary skill in this art without the exercise of undue experimentation.

Example 43

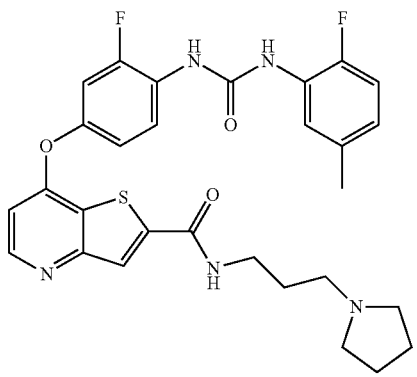 [SMILES: Cc1ccc(F)c(NC(=O)Nc2ccc(Oc3ccnc4cc(C(=O)NCCCN5CCCC5)sc34)cc2F)c1]

7-[3-fluoro-4-({[(2-fluoro-5-methylphenyl)amino]carbonyl}amino)phenoxy]-N-(3-pyrrolidin-1-ylpropyl)thieno[3,2-b]pyridine-2-carboxamide $^1$H NMR (DMSO-d$_6$): 9.10 (dd, J=2.1, 0.6 Hz, 1H), 8.93-8.98 (m, 2H), 8.56 (d, J=5.3 Hz, 1H), 8.26 (t, J=9.1 Hz, 1H), 8.19 (s, 1H), 7.98 (dd, J=7.9, 2.3 Hz, 1H), 7.39 (dd, J=11.6, 2.8 Hz, 1H), 7.10-7.13 (m, 1H), 7.09 (dd, J=11.3, 8.4 Hz, 1H), 6.78-6.82 (m, 1H), 6.77 (d, J=5.3 Hz, 1H), 3.29-3.34 (m, 2H), 2.37-2.45 (m, 6H), 2.25 (s, 3H), 1.70 (quin, J=7.0 Hz, 2H), 1.63-1.67 (m, 4H)

LR MS (ES+): 566 (MH+)
LR MS (ES−): 564 (M−H)

Example 44

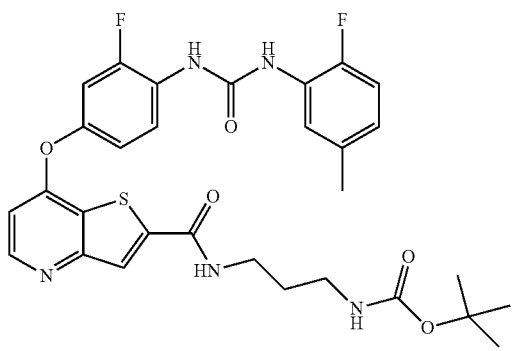 [SMILES: Cc1ccc(F)c(NC(=O)Nc2ccc(Oc3ccnc4cc(C(=O)NCCCNC(=O)OC(C)(C)C)sc34)cc2F)c1]

tert-butyl {3-[({7-[3-fluoro-4-({[(2-fluoro-5-methylphenyl)amino]carbonyl}amino)phenoxy]thieno[3,2-b]pyridin-2-yl}carbonyl)amino]propyl}carbamate a mixture of 7-[3-fluoro-4-({[(2-fluoro-5-methylphenyl)amino]carbonyl}amino)phenoxy]thieno[3,2-b]pyridine-2-carboxylic acid (300 mg, 0.66 mmol), HATU (277 mg, 0.73 mmol) and N,N-diisopropylethylamine (187 mg, 1.45 mmol) in anhydrous acetonitrile (10 ml) was stirred at room temperature for 30 minutes, followed by addition of N-Boc-1,3-propanediamine (172 mg, 0.99 mmol). The mixture was stirred for another 10 minutes and poured into 100 ml of water with vigorous stirring. 2M HCl was added dropwise until pH=5. The precipitates were filtered, washed with water and dried in vacuo to give tert-butyl (3-[({7-[3-fluoro-4-({[(2-fluoro-5-methylphenyl)amino]carbonyl}amino)phenoxy]thieno[3,2-b]pyridin-2-yl}carbonyl)amino]propyl)carbamate as light yellow solid. Yield: 345 mg, 85%.

$^1$H NMR (DMSO-d$_6$): 9.10 (d, J=2.6 Hz, 1H), 8.96 (d, J=2.6 Hz, 1H), 8.87 (t, J=5.7 Hz, 1H), 8.56 (d, J=5.3 Hz, 1H), 8.26 (t, J=9.1 Hz, 1H), 8.21 (s, 1H), 7.98 (dd, J=7.9, 2.1 Hz, 1H), 7.39 (dd, J=11.7, 2.9 Hz, 1H), 7.11 (ddd, J=9.0, 2.9, 1.0 Hz, 1H), 7.09 (dd, J=11.3, 8.4 Hz, 1H), 6.78-6.83 (m, 2H), 6.77 (d, J=5.3 Hz, 1H), 3.24-3.28 (m, 2H), 2.97 (q, J=6.7 Hz, 2H), 2.25 (s, 3H), 1.64 (quin, J=7.0 Hz, 2H), 1.35 (s, 9H)

LR MS (ES+): 634 (MNa+)
LR MS (ES−): 610 (M−H)

Example 45

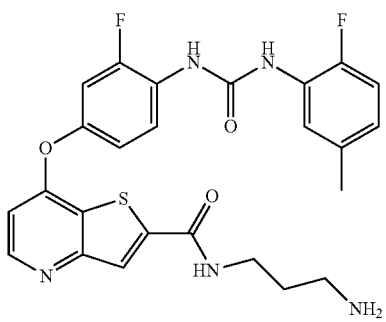 [SMILES: Cc1ccc(F)c(NC(=O)Nc2ccc(Oc3ccnc4cc(C(=O)NCCCN)sc34)cc2F)c1]

N-(3-aminopropyl)-7-[3-fluoro-4-({[(2-fluoro-5-methylphenyl)amino]carbonyl}amino)phenoxy]thieno[3,2-b]pyridine-2-carboxamide to a stirred suspension of tert-butyl (3-[({7-[3-fluoro-4-({[(2-fluoro-5-methylphenyl)amino]carbonyl}amino)phenoxy]thieno[3,2-b]pyridin-2-yl}carbonyl)amino]propyl)carbamate (300 mg, 0.49 mmol) in 10 ml of methylene chloride was added 3 ml of trifluoroacetic acid. The mixture was stirred at room temperature for 10 minutes and evaporated to dryness under reduced pressure. The residue was re-dissolved in MeOH (5 ml) and poured into 100 ml of water with vigorous stirring. Saturated NaHCO$_3$ solution was added until pH=8~9. The precipitates were filtered, washed with water and dried in vacuo to give N-(3-aminopropyl)-7-[3-fluoro-4-({[(2-fluoro-5-methylphenyl)amino]carbonyl}amino)phenoxy]thieno[3,2-b]pyridine-2-carboxamide as yellow solid. Yield: 250 mg, 100%.

LR MS (ES+): 512 (MNa+)
LR MS (ES−): 510 (M−H)

Example 46

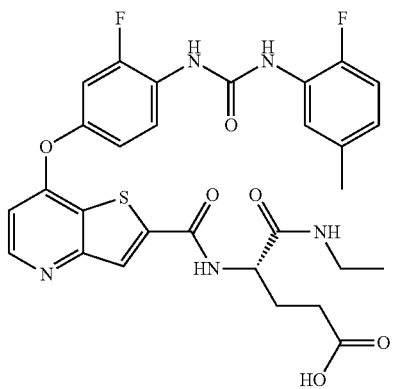 [SMILES: CCNC(=O)[C@H](CCC(=O)O)NC(=O)c1cc2nccc(Oc3ccc(NC(=O)Nc4cc(C)ccc4F)c(F)c3)c2s1]

(4S)-5-(ethylamino)-4-[({7-[3-fluoro-4-({[(2-fluoro-5-methylphenyl)amino]carbonyl}amino)phenoxy]thieno[3,2-b]pyridin-2-yl carbonyl}amino]-5-oxopentanoic acid to a stirred suspension of tert-butyl (4S)-5-(ethylamino)-4-[({7-[3-fluoro-4-({[(2-fluoro-5-methylphenyl)amino] carbonyl}amino)phenoxy]thieno[3,2-b]pyridin-2-yl}carbonyl)amino]-5-oxopentanoate (70 mg, 0.10 mmol) in 5 ml of methylene chloride was added 2 ml of trifluoroacetic acid. The mixture was stirred at room temperature for 2 hours and evaporated to dryness under reduced pressure. The residue was re-dissolved in MeOH (5 ml) and poured into 100 ml of water with vigorous stirring. The precipitates were filtered, washed with water and dried in vacuo to give (4S)-5-(ethylamino)-4-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoic acid as light yellow solid. Yield: 53 mg, 83%.

$^1$H NMR (DMSO-d$_6$): 12.12 (br. s., 1H), 9.10 (d, J=2.3 Hz, 1H), 8.94-8.98 (m, 2H), 8.59 (d, J=5.6 Hz, 1H), 8.42 (s, 1H), 8.26 (t, J=9.1 Hz, 1H), 8.04 (t, J=5.6 Hz, 1H), 7.98 (dd, J=7.8, 1.9 Hz, 1H), 7.40 (dd, J=11.7, 2.6 Hz, 1H), 7.07-7.13 (m, 2H), 6.79-6.81 (m, 1H), 6.77-6.81 (m, 1H), 4.34-4.42 (m, 1H), 3.02-3.13 (m, 2H), 2.29 (td, J=9.4, 6.2 Hz, 2H), 2.25 (s, 3H), 1.97-2.09 (m, 1H), 1.84-1.95 (m, 1H), 1.00 (t, J=7.2 Hz, 3H)

LR MS (ES−): 610 (M−H)

Example 47

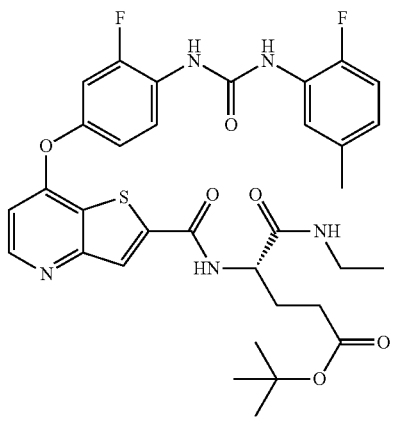 [SMILES: CCNC(=O)[C@H](CCC(=O)OC(C)(C)C)NC(=O)c1cc2nccc(Oc3ccc(NC(=O)Nc4cc(C)ccc4F)c(F)c3)c2s1]

tert-butyl (4S)-5-(ethylamino)-4-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoate to a stirred suspension of (2S)-5-tert-butoxy-2-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoic acid (100 mg, 0.16 mmol) in 10 ml of anhydrous tetrahydrofuran were added HATU (73 mg, 0.19 mmol) and N,N-diisopropylethylamine (62 mg, 0.48 mmol). The mixture was heated at 60° C. for 10 minutes, followed by addition of 2M ethylamine solution in THF (0.25 ml, 0.50 mmol). The mixture was heated at 60° C. for another 5 minutes, cooled to room temperature and poured into 100 ml of water with vigorous stirring. 1M HCl was added dropwise until pH=4. The precipitates were filtered, washed with water and dried in vacuo to give the crude, which was purified by silica gel chromatography eluting with 3-5% methanol in chloroform to give tert-butyl (4S)-5-(ethylamino)-4-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoate as white solid. Yield: 73 mg, 70%.

$^1$H NMR (DMSO-d$_6$): 9.10 (d, J=2.3 Hz, 1H), 8.96 (d, J=2.3 Hz, 1H), 8.93 (d, J=7.9 Hz, 1H), 8.58 (d, J=5.6 Hz, 1H), 8.42 (s, 1H), 8.26 (t, J=9.1 Hz, 1H), 8.02 (t, J=5.6 Hz, 1H), 7.98 (dd, J=7.8, 1.9 Hz, 1H), 7.39 (dd, J=11.7, 2.6 Hz, 1H), 7.11 (ddd, J=9.0, 2.7, 1.2 Hz, 1H), 7.09 (dd, 1H), 6.79 (d, J=5.6 Hz, 1H), 6.78-6.81 (m, 1H), 4.32-4.43 (m, 1H), 3.02-3.14 (m, 2H), 2.26-2.30 (m, 2H), 2.25 (s, 3H), 1.97-2.05 (m, 1H), 1.83-1.92 (m, 1H), 1.36 (s, 9H), 1.00 (t, J=7.2 Hz, 3H)

LR MS (ES+): 690 (MNa+)
LR MS (ES−): 666 (M−H)

Example 48

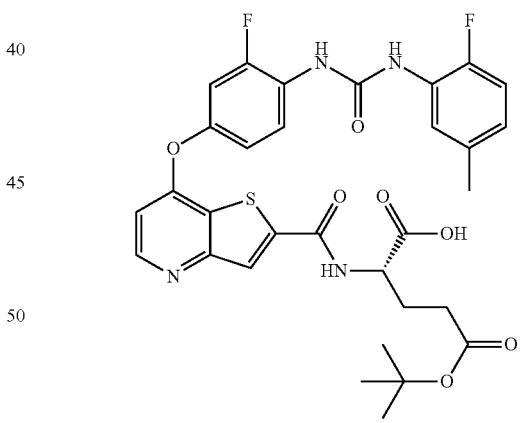

(2S)-5-tert-butoxy-2-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoic acid to a stirred solution of 5-tert-butyl 1-methyl (2S)-2-[({7-[3-fluoro-4-({[(2-fluoro-5-methylphenyl)amino]carbonyl}amino)phenoxy]thieno[3,2-b]pyridin-2-yl}carbonyl)amino]pentanedioate (260 mg, 0.40 mmol) in a mixture of THF/MeOH (10 ml/10 ml) was added 1M NaOH solution (2 ml, 2 mmol). The mixture was stirred at room temperature for 1 hour and poured into 100 ml of water. 1M HCl was added with stirring until pH=4. The precipitates were filtered, washed with water and dried in vacuo to give (2S)-5-tert-butoxy-2-[({7-[3-fluoro-4-({[(2-fluoro-5-methylphenyl)amino]carbonyl}amino)phenoxy]thieno[3,2-b]pyridin-2-yl}carbonyl)amino]-5-oxopentanoic acid as off-white solid. Yield: 230 mg, 91%.

$^1$H NMR (DMSO-d$_6$): 12.81 (br. s., 1H), 9.11 (d, J=2.3 Hz, 1H), 9.07 (d, J=7.9 Hz, 1H), 8.97 (d, J=2.3 Hz, 1H), 8.58 (d, J=5.3 Hz, 1H), 8.38 (s, 1H), 8.26 (t, J=9.1 Hz, 1H), 7.98 (dd, J=7.9, 2.1 Hz, 1H), 7.40 (dd, J=11.6, 2.8 Hz, 1H), 7.11-7.13 (m, 1H), 7.09 (dd, J=11.3, 8.4 Hz, 1H), 6.79 (d, J=5.3 Hz, 1H), 6.78-6.82 (m, 1H), 4.40 (ddd, J=9.8, 7.7, 4.8 Hz, 1H), 2.33-2.37 (m, 2H), 2.25 (s, 3H), 2.04-2.13 (m, 1H), 1.89-2.00 (m, 1H), 1.36 (s, 9H)

LR MS (ES-): 639 (M-H)

The following Example 49 was prepared using the experiment procedure described in Example 54, but with the appropriate reagent, reaction conditions and reactant substitutions that will be readily realized by those of ordinary skill in this art without the exercise of undue experimentation.

Example 49

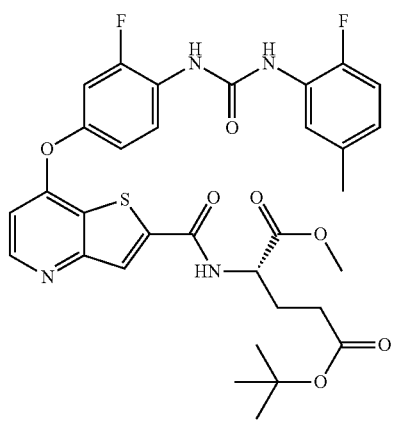 [SMILES: COC(=O)[C@H](CCC(=O)OC(C)(C)C)NC(=O)c1cc2nccc(Oc3ccc(NC(=O)Nc4cc(C)ccc4F)c(F)c3)c2s1]

5-tert-butyl 1-methyl (2S)-2-[({7-[3-fluoro-4-({[(2-fluoro-5-methylphenyl)amino]carbonyl}amino)phenoxy]thieno[3,2-b]pyridin-2-yl}carbonyl)amino]pentanedioate $^1$H NMR (DMSO-d$_6$): 9.18 (d, J=7.6 Hz, 1H), 9.10 (d, J=2.3 Hz, 1H), 8.96 (d, J=2.3 Hz, 1H), 8.59 (d, J=5.6 Hz, 1H), 8.38 (s, 1H), 8.26 (t, J=9.1 Hz, 1H), 7.98 (dd, J=7.9, 1.8 Hz, 1H), 7.40 (dd, J=11.6, 2.8 Hz, 1H), 7.10-7.13 (m, 1H), 7.09 (dd, J=11.2, 8.2 Hz, 1H), 6.80 (d, J=5.6 Hz, 1H), 6.78-6.81 (m, 1H), 4.48 (ddd, J=9.4, 7.3, 5.3 Hz, 1H), 3.65 (s, 3H), 2.36 (t, J=7.5 Hz, 2H), 2.25 (s, 3H), 2.03-2.12 (m, 1H), 1.92-2.01 (m, 1H), 1.37 (s, 9H)

LR MS (ES+): 677 (MNa+)

LR MS (ES-): 653 (M-H)

Example 50

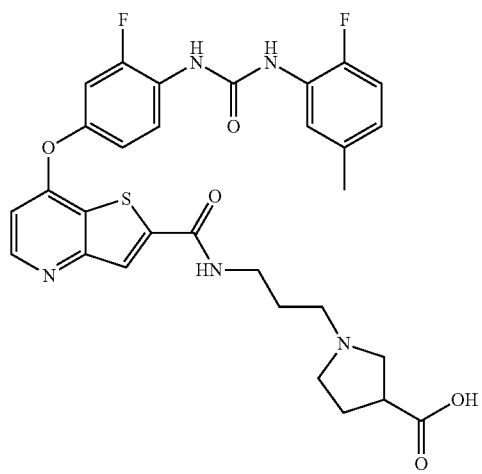 [SMILES: Cc1ccc(F)c(NC(=O)Nc2ccc(Oc3ccnc4cc(C(=O)NCCCN5CCC(C(=O)O)C5)sc34)cc2F)c1]

1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-3-carboxylic acid to a stirred solution of tert-butyl 1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-3-carboxylate (40 mg, 0.060 mmol) in 5 ml of methylene chloride was added 2 ml of trifluoroacetic acid. The mixture was stirred at room temperature for 2 hours, and evaporated to dryness under reduced pressure. 5 ml of water was added to the residue, and the mixture was neutralized to pH=7 with saturated NaHCO$_3$ solution with vigorous stirring. The precipitates were filtered, washed with 5 ml of water, and dried in vacuo to give 1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-3-carboxylic acid as light brown solid. Yield: 37 mg, 100%.

LR MS (ES+): 610 (MH+)

LR MS (ES-): 608 (M-H)

The following Example 51 was prepared using the experiment procedure described in Example 42, but with the appropriate reagent, reaction conditions and reactant substitutions that will be readily realized by those of ordinary skill in this art without the exercise of undue experimentation.

Example 51

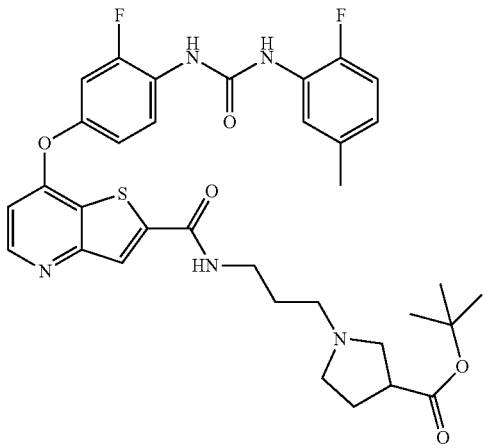 [SMILES: Cc1ccc(F)c(NC(=O)Nc2ccc(Oc3ccnc4cc(C(=O)NCCCN5CCC(C(=O)OC(C)(C)C)C5)sc34)cc2F)c1]

tert-butyl 1-{3-[({7-[3-fluoro-4-({[(2-fluoro-5-methylphenyl)amino]carbonyl}amino)phenoxy]thieno[3,2-b]pyridin-2-yl}carbonyl)amino]propyl}pyrrolidine-3-carboxylate LR MS (ES+): 688 (MNa+)
LR MS (ES−): 664 (M−H)

Example 52

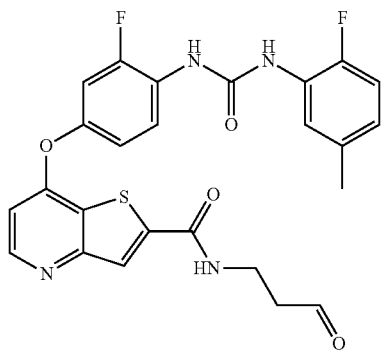 [SMILES: Cc1ccc(F)c(NC(=O)Nc2ccc(Oc3ccnc4cc(C(=O)NCCC=O)sc34)cc2F)c1]

7-[3-fluoro-4-({[(2-fluoro-5-methylphenyl)amino]carbonyl}amino)phenoxy]-N-(3-oxopropyl)thieno[3,2-b]pyridine-2-carboxamide to a stirred solution of N-(3,3-diethoxypropyl)-7-[3-fluoro-4-({[(2-fluoro-5 methylphenyl)amino]carbonyl}amino)phenoxy]thieno[3,2-b]pyridine-2-carboxamide (1.23 g, 2.11 mmol) in 20 ml of tetrahydrofuran was added 2 ml of 2M HCl (4.0 mmol). The mixture was stirred at room temperature for 5 hours and poured into 100 ml of water. 1M NaOH solution was added slowly until pH=7~8. The precipitates were filtered, washed with water and dried in vacuo to give 7-[3-fluoro-4-({[(2-fluoro-5-methylphenyl)amino]carbonyl}amino)phenoxy]-N-(3-oxopropyl)thieno[3,2-b]pyridine-2-carboxamide as brown solid. Yield: 1.07 g, 100%.

$^1$H NMR (DMSO-$d_6$): 9.69 (t, J=1.6 Hz, 1H), 9.10 (d, J=2.3 Hz, 1H), 9.00-9.04 (m, 1H), 8.97 (d, J=2.6 Hz, 1H), 8.56 (d, J=5.3 Hz, 1H), 8.26 (t, J=9.1 Hz, 1H), 8.20 (s, 1H), 7.98 (dd, J=7.9, 2.3 Hz, 1H), 7.39 (dd, J=11.6, 2.8 Hz, 1H), 7.07-7.13 (m, 2H), 6.78-6.81 (m, 1H), 6.77 (d, J=5.6 Hz, 1H), 3.52-3.60 (m, 2H), 2.73 (td, J=6.7, 1.6 Hz, 2H), 2.25 (s, 3H).

LR MS (ES+): 533 (MNa+)
LR MS (ES−): 509 (M−H)

Example 53

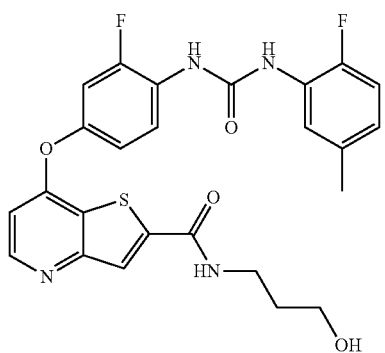 [SMILES: Cc1ccc(F)c(NC(=O)Nc2ccc(Oc3ccnc4cc(C(=O)NCCCO)sc34)cc2F)c1]

7-[3-fluoro-4-({[(2-fluoro-5-methylphenyl)amino]carbonyl}amino)phenoxy]-N-(3-hydroxypropyl)thieno[3,2-b]pyridine-2-carboxamide to a stirred suspension of 7-[3-fluoro-4-({[(2-fluoro-5-methylphenyl)amino]carbonyl}amino)phenoxy]thieno[3,2-b]pyridine-2-carboxylic acid (1.00 g, 2.20 mmol) in 20 ml of anhydrous THF were added HATU (1.04 g, 2.74 mmol) and N,N-diisopropylethylamine (636 mg, 4.93 mmol). The mixture was heated at 60° C. for 15 minutes, followed by addition of 3-aminopropanol (248 mg, 3.3 mmol). The mixture was stirred for another 10 minutes, cooled to room temperature and poured into 100 ml of water with vigorous stirring. 2M HCl was added dropwise until pH=4. The precipitates were filtered, washed with water and dried in vacuo to give 7-[3-fluoro-4-({[(2-fluoro-5-methylphenyl)amino]carbonyl}amino)phenoxy]-N-(3-hydroxypropyl)thieno[3,2-b]pyridine-2-carboxamide as white solid. Yield: 1.12 g, 100%.

$^1$H NMR (DMSO-$d_6$): 9.10 (s, 1H), 8.96 (d, J=1.8 Hz, 1H), 8.91 (t, J=5.4 Hz, 1H), 8.57 (d, J=5.6 Hz, 1H), 8.26 (t, J=9.0 Hz, 1H), 8.22 (s, 1H), 7.98 (dd, J=7.9, 2.3 Hz, 1H), 7.40 (dd, J=11.4, 2.6 Hz, 1H), 7.06-7.14 (m, 2H), 6.79-6.82 (m, 1H), 6.78 (d, J=5.6 Hz, 1H), 3.46 (t, J=6.2 Hz, 2H), 3.33 (q, J=6.6 Hz, 2H), 2.25 (s, 3H), 1.69 (quin, J=6.7 Hz, 2H)

LR MS (ES+): 535 (MNa+)
LR MS (ES−): 511 (M−H)

Example 54

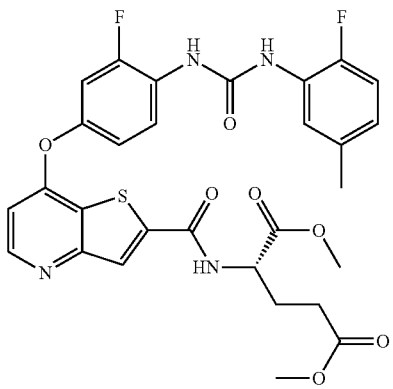 [SMILES: COC(=O)CC[C@H](NC(=O)c1cc2nccc(Oc3ccc(NC(=O)Nc4cc(C)ccc4F)c(F)c3)c2s1)C(=O)OC]

dimethyl (2S)-2-[({7-[3-fluoro-4-({[(2-fluoro-5-methylphenyl)amino]carbonyl}amino)phenoxy]thieno[3,2-b]pyridin-2-yl}carbonyl)amino]pentanedioate to a stirred suspension of 7-[3-fluoro-4-({[(2-fluoro-5-methylphenyl)amino]carbonyl}amino)phenoxy]thieno[3,2-b]pyridine-2-carboxylic acid (100 mg, 0.22 mmol) in 10 ml of anhydrous tetrahydrofuran were added HATU (100 mg, 0.26 mmol) and N,N-diisopropylethylamine (85 mg, 0.66 mmol). The mixture was heated at 60° C. for 10 minutes, followed by addition of L-glutamic acid dimethyl ester hydrochloride (55 mg, 0.26 mmol). The mixture was heated at 60° C. for another 20 minutes, cooled to room temperature and poured into 100 ml of water with vigorous stirring. 1M HCl was added dropwise until pH=4. The precipitates were filtered, washed with water and dried in vacuo to give dimethyl (2S)-2-[({7-[3-fluoro-4-({[(2-fluoro-5-methylphenyl)amino]carbonyl}amino)phenoxy]thieno[3,2-b]pyridin-2-yl}carbonyl)amino]pentanedioate as white solid. Yield: 126 mg, 94%.

¹H NMR (DMSO-d₆): 9.21 (d, J=7.3 Hz, 1H), 9.10 (d, J=2.1 Hz, 1H), 8.96 (d, J=2.3 Hz, 1H), 8.59 (d, J=5.3 Hz, 1H), 8.37 (s, 1H), 8.26 (t, J=9.1 Hz, 1H), 7.98 (dd, J=7.8, 1.9 Hz, 1H), 7.40 (dd, J=11.6, 2.8 Hz, 1H), 7.06-7.15 (m, 2H), 6.77-6.82 (m, 2H), 4.48 (ddd, J=9.4, 7.3, 5.3 Hz, 1H), 3.65 (s, 3H), 3.57 (s, 3H), 2.45-2.49 (m, 2H), 2.25 (s, 3H), 2.09-2.18 (m, 1H), 1.97-2.07 (m, 1H)
LR MS (ES+): 635 (MNa+)
LR MS (ES−): 611 (M−H)

The following Example 55 was prepared using the experiment procedure described in Example 34, but with the appropriate reagent, reaction conditions and reactant substitutions that will be readily realized by those of ordinary skill in this art without the exercise of undue experimentation.

Example 55

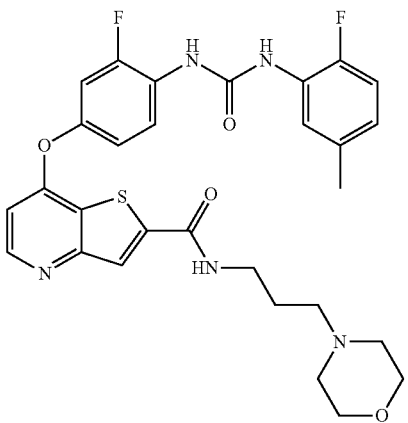 [SMILES: Cc1ccc(F)c(NC(=O)Nc2ccc(Oc3ccnc4cc(C(=O)NCCCN5CCOCC5)sc34)cc2F)c1]

7-[3-fluoro-4-({[(2-fluoro-5-methylphenyl)amino]carbonyl}amino)phenoxy]-N-(3-morpholin-4-ylpropyl)thieno[3,2-b]pyridine-2-carboxamide ¹H NMR (DMSO-d₆): 9.12 (d, J=1.8 Hz, 1H), 8.98 (d, J=2.3 Hz, 1H), 8.93 (t, J=5.7 Hz, 1H), 8.56 (d, J=5.3 Hz, 1H), 8.25 (t, J=9.1 Hz, 1H), 8.22 (s, 1H), 7.98 (dd, J=7.9, 2.1 Hz, 1H), 7.39 (dd, J=11.7, 2.6 Hz, 1H), 7.06-7.13 (m, 2H), 6.78-6.82 (m, 1H), 6.77 (d, J=5.3 Hz, 1H), 3.54 (t, J=4.5 Hz, 4H), 3.31 (q, J=6.75 Hz, 2H), 2.29-2.37 (m, 6H), 2.25 (s, 3H), 1.69 (quin, J=7.0 Hz, 2H)
LR MS (ES+): 582 (MH+)
LR MS (ES−): 580 (M−H)

Example 56

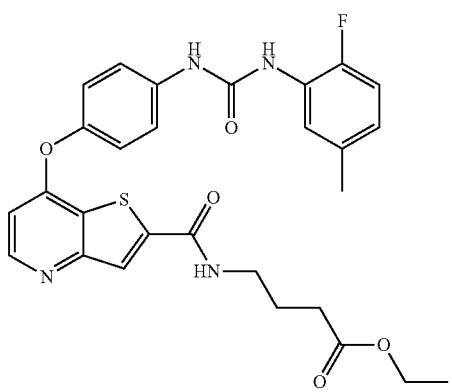 [SMILES: CCOC(=O)CCCNC(=O)c1cc2nccc(Oc3ccc(NC(=O)Nc4cc(C)ccc4F)cc3)c2s1]

ethyl 4-[({7-[4-({[(2-fluoro-5-methylphenyl)amino]carbonyl}amino)phenoxy]thieno[3,2-b]pyridin-2-yl}carbonyl)amino]butanoate to a stirred suspension of 7-[4-({[(2-fluoro-5-methylphenyl)amino]carbonyl}amino)phenoxy]thieno[3,2-b]pyridine-2-carboxylic acid (120 mg, 0.27 mmol) in 10 ml of anhydrous THF were added HATU (122 mg, 0.32 mmol) and N,N-diisopropylethylamine (104 mg, 0.81 mmol). The mixture was heated at 60° C. for 5 minutes, followed by addition of ethyl 4-aminobutyrate hydrochloride (67 mg, 0.40 mmol). The mixture was stirred for another 10 minutes, cooled to room temperature and poured into 100 ml of water with vigorous stirring. 1M HCl was added dropwise until pH=5. The precipitates were filtered, washed with water and dried in vacuo to give ethyl 4-[({7-[4-({[(2-fluoro-5-methylphenyl)amino]carbonyl}amino)phenoxy]thieno[3,2-b]pyridin-2-yl}carbonyl)amino]butanoate as white solid. Yield: 150 mg, 99%.

¹H NMR (DMSO-d₆): 9.19 (s, 1H), 8.92 (t, J=5.7 Hz, 1H), 8.54 (d, J=5.3 Hz, 1H), 8.47 (d, J=2.6 Hz, 1H), 8.21 (s, 1H), 7.94-7.98 (m, 1H), 7.53-7.58 (m, 2H), 7.20-7.25 (m, 2H), 7.08 (dd, J=11.3, 8.4 Hz, 1H), 6.76-6.81 (m, 1H), 6.69 (d, J=5.6 Hz, 1H), 4.03 (q, J=7.0 Hz, 2H), 3.28-3.32 (m, 2H), 2.36 (t, J=7.5 Hz, 2H), 2.25 (s, 3H), 1.79 (quin, J=7.2 Hz, 2H), 1.15 (t, J=7.2 Hz, 3H)
LR MS (ES+): 573 (MNa+)
LR MS (ES−): 549 (M−H)

Example 57

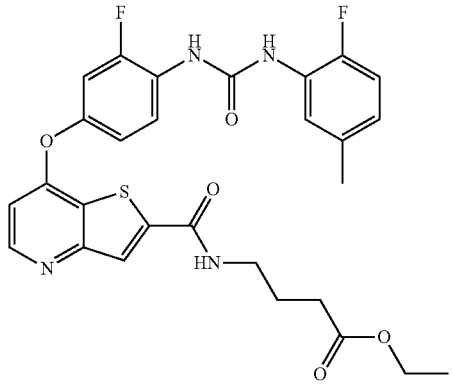 [SMILES: CCOC(=O)CCCNC(=O)c1cc2nccc(Oc3ccc(NC(=O)Nc4cc(C)ccc4F)c(F)c3)c2s1]

ethyl 4-[({7-[3-fluoro-4-({[(2-fluoro-5-methylphenyl)amino]carbonyl}amino)phenoxy]thieno[3,2-b]pyridin-2-yl}carbonyl)amino]butanoate to a stirred suspension of 7-[3-fluoro-4-({[(2-fluoro-5-methylphenyl)amino]carbonyl}amino)phenoxy]thieno[3,2-b]pyridine-2-carboxylic acid (120 mg, 0.26 mmol) in 10 ml of anhydrous THF were added HATU (118 mg, 0.31 mmol) and N,N-diisopropylethylamine (100 mg, 0.78 mmol). The mixture was heated at 60° C. for 5 minutes, followed by addition of ethyl 4-aminobutyrate hydrochloride (67 mg, 0.40 mmol). The mixture was stirred for another 10 minutes, cooled to room temperature and poured into 100 ml of water with vigorous stirring. 1M HCl was added dropwise until pH=5. The precipitates were filtered, washed with water and dried in vacuo to give ethyl 4-[({7-[3-fluoro-4-({[(2-fluoro-5-methylphenyl)amino]carbonyl}amino)phenoxy]thieno[3,2-b]pyridin-2-yl}carbonyl)amino]butanoate as white solid. Yield: 150 mg, 100%.

¹H NMR (DMSO-d₆): 9.10 (d, 1H), 8.96 (d, J=2.6 Hz, 1H), 8.93 (t, J=5.7 Hz, 1H), 8.56 (d, J=5.3 Hz, 1H), 8.26 (t, J=9.1 Hz, 1H), 7.98 (s, 1H), 8.22 (s, 1H), 7.98 (s, 1H), 7.39 (dd, J=11.7, 2.9 Hz, 1H), 7.10-7.13 (m, 1H), 7.09 (dd, J=11.2, 8.2 Hz, 1H), 6.78-6.81 (m, 1H), 6.78 (d, J=5.6 Hz, 1H), 4.03 (q, J=7.2 Hz, 2H), 3.27-3.32 (m, 2H), 2.36 (t, J=7.3 Hz, 2H), 2.25 (s, 3H), 1.79 (quin, J=7.2 Hz, 2H), 1.15 (t, J=7.2 Hz, 3H)

LR MS (ES+): 591 (MNa+)
LR MS (ES−): 567 (M−H)

Example 58

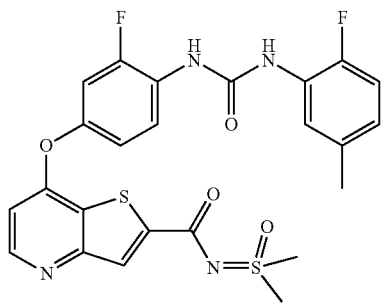 [SMILES: Cc1ccc(F)c(NC(=O)Nc2ccc(Oc3ccnc4cc(C(=O)N=S(C)(C)=O)sc34)cc2F)c1]

N-[dimethyl(oxido)-lambda~4~-sulfanylidene]-7-[3-fluoro-4-({[(2-fluoro-5-methylphenyl)amino]carbonyl}amino)phenoxy]thieno[3,2-b]pyridine-2-carboxamide Example 59

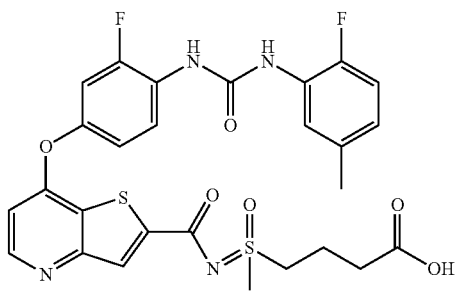 [SMILES: Cc1ccc(F)c(NC(=O)Nc2ccc(Oc3ccnc4cc(C(=O)N=S(C)(=O)CCCC(=O)O)sc34)cc2F)c1]

4-[N-({7-[3-fluoro-4-({[(2-fluoro-5-methylphenyl)amino]carbonyl}amino)phenoxy]thieno[3,2-b]pyridin-2-yl}carbonyl)-S-methylsulfonimidoyl]butanoic acid Example 60

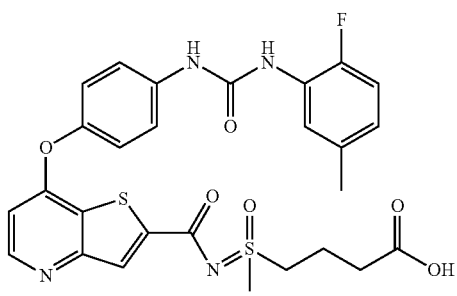 [SMILES: Cc1ccc(F)c(NC(=O)Nc2ccc(Oc3ccnc4cc(C(=O)N=S(C)(=O)CCCC(=O)O)sc34)cc2)c1]

4-[N-({7-[4-({[(2-fluoro-5-methylphenyl)amino]carbonyl}amino)phenoxy]thieno[3,2-b]pyridin-2-yl}carbonyl)-S-methylsulfonimidoyl]butanoic acid Example 61

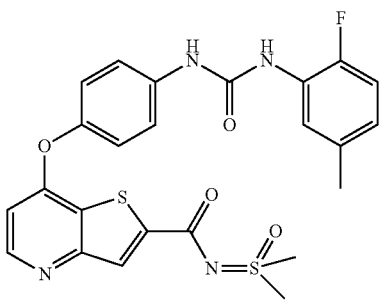 [SMILES: Cc1ccc(F)c(NC(=O)Nc2ccc(Oc3ccnc4cc(C(=O)N=S(C)(C)=O)sc34)cc2)c1]

N-[dimethyl(oxido)-lambda~4~-sulfanylidene]-7-[4-({[(2-fluoro-5-methylphenyl)amino]carbonyl}amino)phenoxy]thieno[3,2-b]pyridine-2-carboxamide Example 62

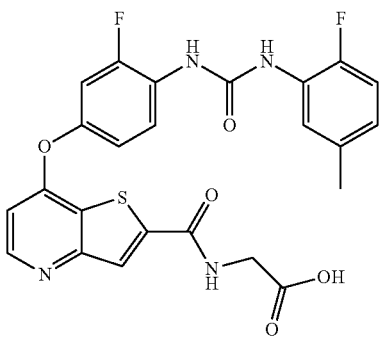 [SMILES: Cc1ccc(F)c(NC(=O)Nc2ccc(Oc3ccnc4cc(C(=O)NCC(=O)O)sc34)cc2F)c1]

[({7-[3-fluoro-4-({[(2-fluoro-5-methylphenyl)amino]carbonyl}amino)phenoxy]thieno[3,2-b]pyridin-2-yl}carbonyl)amino]acetic acid Example 63

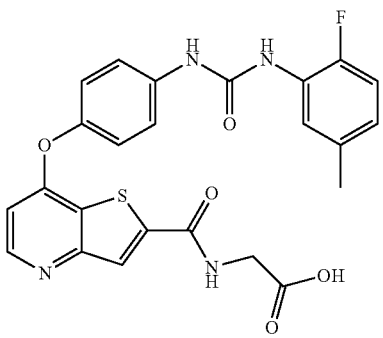 [SMILES: Cc1ccc(F)c(NC(=O)Nc2ccc(Oc3ccnc4cc(C(=O)NCC(=O)O)sc34)cc2)c1]

[({7-[4-({[(2-fluoro-5-methylphenyl)amino]
carbonyl}amino)phenoxy]thieno[3,2-b]pyridin-2-
yl}carbonyl)amino]acetic acid Example 64

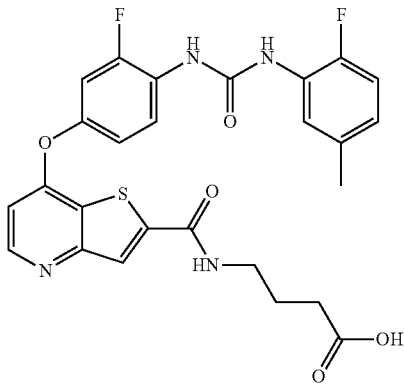 [SMILES: Cc1ccc(F)c(NC(=O)Nc2ccc(Oc3ccnc4cc(C(=O)NCCCC(=O)O)sc34)cc2F)c1]

4-[({7-[3-fluoro-4-({[(2-fluoro-5-methylphenyl)amino]
carbonyl}amino)phenoxy]thieno[3,2-b]pyridin-2-
yl}carbonyl)amino]butanoic acid to a stirred solution of ethyl 4-[({7-[3-fluoro-4-({[(2-fluoro-5-methylphenyl)amino]carbonyl}amino)phenoxy]thieno[3,2-b]pyridin-2-yl}carbonyl)amino]butanoate (110 mg, 0.19 mmol) in 10 ml of THF was added 1M NaOH (2.0 ml, 2.0 mmol). The mixture was heated at 60° C. for 2 hours, cooled to room temperature and poured into 100 ml of water with vigorous stirring. 2M HCl was added dropwise until pH=4. The precipitates were filtered, washed with water and dried in vacuo to give 4-[({7-[3-fluoro-4-({[(2-fluoro-5-methylphenyl)amino]carbonyl}amino)phenoxy]thieno[3,2-b]pyridin-2-yl}carbonyl)amino]butanoic acid as white solid. Yield: 95 mg, 90%.

¹H NMR (DMSO-d₆): 12.07 (br. s., 1H), 9.11 (d, J=2.3 Hz, 1H), 8.97 (d, J=2.3 Hz, 1H), 8.94 (t, J=5.6 Hz, 1H), 8.57 (d, J=5.3 Hz, 1H), 8.26 (t, J=9.1 Hz, 1H), 8.23 (s, 1H), 7.98 (dd, J=7.9, 2.3 Hz, 1H), 7.40 (dd, J=11.6, 2.8 Hz, 1H), 7.11-7.13 (m, 1H), 7.09 (dd, J=11.3, 8.4 Hz, 1H), 6.79-6.81 (m, 1H), 6.78 (d, J=5.3 Hz, 1H), 3.26-3.33 (m, 2H), 2.29 (t, J=7.3 Hz, 2H), 2.25 (s, 3H), 1.77 (quin, J=7.1 Hz, 2H)

LR MS (ES+): 541 (MH+)
LR MS (ES−): 539 (M−H)

Example 65

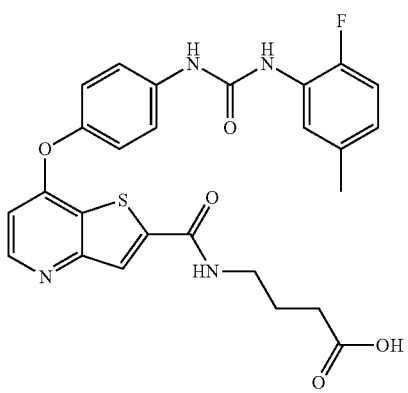 [SMILES: Cc1ccc(F)c(NC(=O)Nc2ccc(Oc3ccnc4cc(C(=O)NCCCC(=O)O)sc34)cc2)c1]

4-[({7-[4-({[(2-fluoro-5-methylphenyl)amino]
carbonyl}amino)phenoxy]thieno[3,2-b]pyridin-2-
yl}carbonyl)amino]butanoic acid to a stirred solution of ethyl 4-[({7-[4-({[(2-fluoro-5-methylphenyl)amino]carbonyl}amino)phenoxy]thieno[3,2-b]pyridin-2-yl}carbonyl)amino]butanoate (110 mg, 0.20 mmol) in 10 ml of THF was added 1M NaOH (2.0 ml, 2.0 mmol). The mixture was heated at 60° C. for 3 hours, cooled to room temperature and poured into 100 ml of water with vigorous stirring. 2M HCl was added dropwise until pH=4. The precipitates were filtered, washed with water and dried in vacuo to give 4-[({7-[4-({[(2-fluoro-5-methylphenyl)amino]carbonyl}amino)phenoxy]thieno[3,2-b]pyridin-2-yl}carbonyl)amino]butanoic acid as white solid. Yield: 100 mg, 96%.

¹H NMR (DMSO-d₆): 12.06 (s, 1H), 9.19 (s, 1H), 8.91 (t, J=5.7 Hz, 1H), 8.54 (d, J=5.3 Hz, 1H), 8.47 (d, J=2.9 Hz, 1H), 8.21 (s, 1H), 7.96 (dd, J=7.9, 2.3 Hz, 1H), 7.54-7.58 (m, 2H), 7.20-7.24 (m, 2H), 7.08 (dd, J=11.3, 8.4 Hz, 1H), 6.76-6.81 (m, 1H), 6.68 (d, J=5.3 Hz, 1H), 3.27-3.31 (m, 2H), 2.29 (t, J=7.3 Hz, 2H), 2.25 (s, 3H), 1.76 (quin, J=7.2 Hz, 2H)

LR MS (ES+): 545 (MNa+)
LR MS (ES−): 521 (M−H)

Example 66

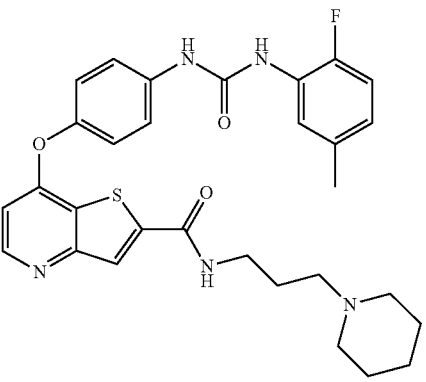 [SMILES: Cc1ccc(F)c(NC(=O)Nc2ccc(Oc3ccnc4cc(C(=O)NCCCN5CCCCC5)sc34)cc2)c1]

7-[4-({[(2-fluoro-5-methylphenyl)amino]
carbonyl}amino)phenoxy]-N-(3-piperidin-1-ylpropyl)
thieno[3,2-b]pyridine-2-carboxamide to a stirred, cooled (0° C.) solution of 7-[4-({[(2-fluoro-5-methylphenyl)amino]carbonyl}amino)phenoxy]thieno[3,2-b]pyridine-2-carboxylic acid (120 mg, 0.27 mmol) in anhydrous DMF (10 ml) were added PyBOP (156 mg, 0.30 mmol) and N,N-diisopropylethylamine (70 mg, 0.54 mmol). The mixture was stirred at 0° C. for 5 minutes, followed by addition of N-(3-aminopropyl)piperidine (58 mg, 0.41 mmol). Stirring was continued at 0° C. for another 30 minutes. The mixture was poured into 100 ml of water with vigorous stirring. The precipitates were filtered, washed with water and dried to give 7-[4-({[(2-fluoro-5-methylphenyl)amino]carbonyl}amino)phenoxy]-N-(3-piperidin-1-ylpropyl)thieno[3,2-b]pyridine-2-carboxamide as beige solid. Yield: 151 mg, 98%.

¹H NMR (600 MHz, DMSO-d₆) δ ppm 9.21 (s, 1 H) 8.94 (t, J=5.58 Hz, 1 H) 8.56 (d, J=5.28 Hz, 1 H) 8.50 (d, J=2.64 Hz, 1 H) 8.22 (s, 1 H) 7.98 (dd, J=7.63, 2.05 Hz, 1 H) 7.57-7.60 (m, 2 H) 7.23-7.27 (m, 2 H) 7.11 (dd, J=11.30, 8.36 Hz, 1 H) 6.80-6.83 (m, 1 H) 6.71 (d, J=5.28 Hz, 1 H)

3.30-3.35 (m, 2 H) 2.31 (br. s., 6 H) 2.28 (s, 3 H) 1.69-1.75 (m, 2 H) 1.47-1.52 (m, 4 H) 1.38 (br. s., 2 H)
LR MS (ES+): 584 (M+Na⁺)
LR MS (ES−): 560 (M−H)

Example 67

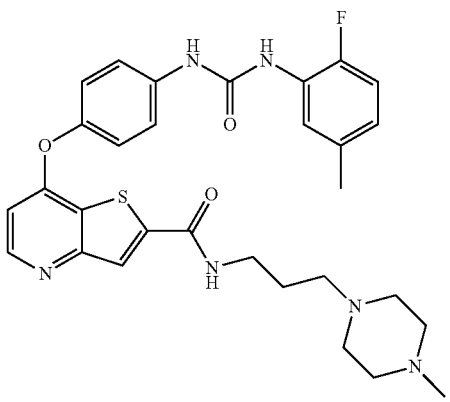 [SMILES: Cc1ccc(F)c(NC(=O)Nc2ccc(Oc3ccnc4cc(C(=O)NCCCN5CCN(C)CC5)sc34)cc2)c1]

7-[4-({[(2-fluoro-5-methylphenyl)amino]carbonyl}amino)phenoxy]-N-[3-(4-methylpiperazin-1-yl)propyl]thieno[3,2-b]pyridine-2-carboxamide The above compound was prepared using procedures similar to that used to prepare the compound of Example 66 above.

$^1$H NMR (600 MHz, DMSO-d$_6$) δ ppm 9.47 (s, 1 H) 8.97 (t, J=5.58 Hz, 1 H) 8.62 (d, J=2.35 Hz, 1 H) 8.56 (d, J=5.28 Hz, 1 H) 8.24 (s, 1 H) 7.97 (dd, J=7.78, 1.91 Hz, 1 H) 7.58-7.61 (m, 2 H) 7.23-7.26 (m, 2 H) 7.10 (dd, J=11.30, 8.36 Hz, 1 H) 6.79-6.82 (m, 1 H) 6.71 (d, J=5.28 Hz, 1 H) 3.32-3.34 (m, 2 H) 2.34-2.47 (m, 10 H) 2.27 (s, 3 H) 2.21 (s, 3 H) 1.72 (quin, J=6.97 Hz, 2 H).
LR MS (ES+): 577 (MH+)

Example 68

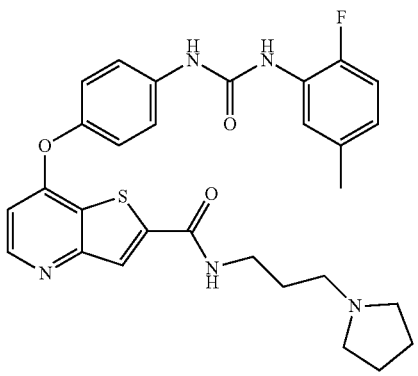 [SMILES: Cc1ccc(F)c(NC(=O)Nc2ccc(Oc3ccnc4cc(C(=O)NCCCN5CCCC5)sc34)cc2)c1]

7-[4-({[(2-fluoro-5-methylphenyl)amino]carbonyl}amino)phenoxy]-N-(3-pyrrolidin-1-ylpropyl)thieno[3,2-b]pyridine-2-carboxamide The above compound was prepared using procedures similar to that used to prepare the compound of Example 66 above.

$^1$H NMR (300 MHz, DMSO-d$_6$) δ ppm 9.23 (s, 1 H) 8.99 (t, J=5.27 Hz, 1 H) 8.57 (d, J=5.27 Hz, 1 H) 8.51 (d, J=2.05 Hz, 1 H) 8.21 (s, 1 H) 7.98 (dd, J=7.77, 1.90 Hz, 1 H) 7.55-7.61 (m, 2 H) 7.22-7.28 (m, 2 H) 7.11 (dd, J=11.43, 8.20 Hz, 1 H) 6.78-6.85 (m, 1 H) 6.72 (d, J=5.27 Hz, 1 H) 3.32-3.39 (m, 2 H) 2.56 (br. s., 6 H) 2.28 (s, 3 H) 1.76 (m, J=8.79 Hz, 6 H)
LR MS (ES+): 548 (MH+)
LR MS (ES−): 546 (M−H)

Example 69

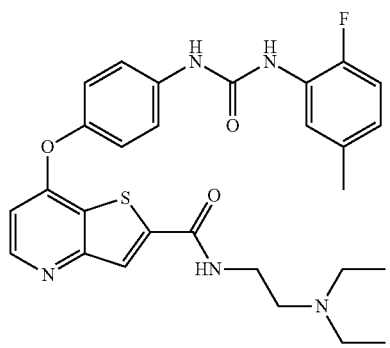 [SMILES: CCN(CC)CCNC(=O)c1cc2nccc(Oc3ccc(NC(=O)Nc4cc(C)ccc4F)cc3)c2s1]

N-[2-(diethylamino)ethyl]-7-[4-({[(2-fluoro-5-methylphenyl)amino]carbonyl}amino)phenoxy]thieno[3,2-b]pyridine-2-carboxamide The above compound was prepared using procedures similar to that used to prepare the compound of Example 66 above.

$^1$H NMR (600 MHz, DMSO-d$_6$) δ ppm 9.21 (s, 1 H) 8.88 (t, J=5.13 Hz, 1 H) 8.56 (d, J=5.28 Hz, 1 H) 8.50 (d, J=2.64 Hz, 1 H) 8.21 (s, 1 H) 7.98 (dd, J=7.92, 2.05 Hz, 1 H) 7.56-7.60 (m, 2 H) 7.23-7.27 (m, 2 H) 7.11 (dd, J=11.30, 8.36 Hz, 1 H) 6.79-6.82 (m, 1 H) 6.71 (d, J=5.28 Hz, 1 H) 3.33-3.37 (m, 2 H) 2.58 (t, J=7.04 Hz, 2 H) 2.50-2.54 (m, 4 H) 2.27 (s, 3 H) 0.97 (t, J=7.04 Hz, 6 H)
LR MS (ES+): 536 (MH+)
LR MS (ES−): 534 (M−H)

Example 70

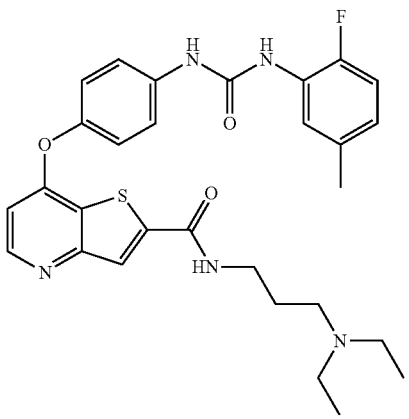 [SMILES: CCN(CC)CCCNC(=O)c1cc2nccc(Oc3ccc(NC(=O)Nc4cc(C)ccc4F)cc3)c2s1]

N-[3-(diethylamino)propyl]-7-[4-({[(2-fluoro-5-methylphenyl)amino]carbonyl}amino)phenoxy]thieno[3,2-b]pyridine-2-carboxamide The above compound was prepared using procedures similar to that used to prepare the compound of Example 66 above.

$^1$H NMR (600 MHz, DMSO-$d_6$) δ ppm 9.25 (s, 1 H) 8.96 (br. s., 1 H) 8.57 (d, J=5.28 Hz, 1 H) 8.53 (d, J=2.35 Hz, 1 H) 8.21 (s, 1 H) 7.98 (dd, J=7.48, 1.91 Hz, 1 H) 7.57-7.61 (m, 2 H) 7.23-7.26 (m, 2 H) 7.11 (dd, J=11.30, 8.36 Hz, 1 H) 6.80-6.83 (m, 1 H) 6.72 (d, J=5.28 Hz, 1 H) 3.32-3.35 (m, 2 H) 2.38-2.49 (m, 6 H) 2.28 (s, 3 H) 1.70 (br. s., 2 H) 0.97 (br. s., 6 H)

LR MS (ES+): 550 (MH+)
LR MS (ES−): 548 (M−H)

Example 71

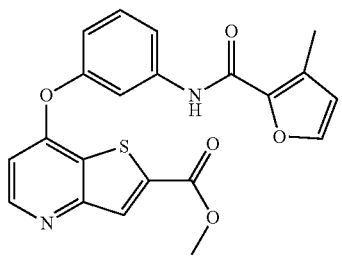 [SMILES: COC(=O)c1cc2nccc(Oc3cccc(NC(=O)c4occc4C)c3)c2s1]

Methyl 7-{3-[(3-methyl-2-furoyl)amino]phenoxy}thieno[3,2-b]pyridine-2-carboxylate Step 1: A mixture of methyl 7-chlorothieno[3,2-b]pyridine-2-carboxylate (500 mg, 2.20 mmol), 3-aminophenol (330 mg, 3.0 mmol), ethyl 2-cyclohexanonecarboxylate (73 mg, 0.43 mmol), copper(I) chloride (22 mg, 0.22 mmol) and cesium carbonate (1.48 g, 4.55 mmol) in 20 ml of anhydrous DMSO was placed in a 50 ml pressure tube, flushed with nitrogen, sealed and heated at 70° C. for 3 hours. The mixture was cooled to room temperature and poured into 100 ml of water. The precipitates were filtered, washed with water and dried to give crude methyl 7-(3-aminophenoxy)thieno[3,2-b]pyridine-2-carboxylate as brown solid. Yield: 330 mg.

Step 2: To a stirred solution of 3-methyl-2-furoic acid (166 mg, 1.32 mmol) in anhydrous DMF (10 ml) were added HATU (552 mg, 1.45 mmol) and DIPEA (341 mg, 2.64 mmol). The mixture was stirred at room temperature for 10 minutes, and 330 mg of crude methyl 7-(3-aminophenoxy)thieno[3,2-b]pyridine-2-carboxylate from step 1 was added. The mixture was then heated at 65° C. for 2 hours, cooled to room temperature, and poured into 100 ml of water. 2M HCl was added until pH=4. The precipitates were filtered, washed with water and dried to give the crude, which was purified by silica gel chromatography eluting with 2~3% of MeOH in chloroform to afford methyl 7-{3-[(3-methyl-2-furoyl)amino]phenoxy}thieno[3,2-b]pyridine-2-carboxylate as off-white solid. Yield: 230 mg, 26% for 2 steps.

$^1$H NMR (300 MHz, DMSO-$d_6$) δ ppm 10.27 (s, 1 H) 8.67 (d, J=5.27 Hz, 1 H) 8.25 (s, 1 H) 7.82 (t, J=2.05 Hz, 1 H) 7.80 (dd, J=1.76, 0.59 Hz, 1 H) 7.76 (ddd, J=8.21, 2.05, 0.88 Hz, 1 H) 7.48 (t, J=8.06 Hz, 1 H) 7.05 (ddd, J=8.06, 2.49, 0.88 Hz, 1 H) 6.90 (d, J=5.27 Hz, 1 H) 6.60 (d, J=2.05 Hz, 1 H) 3.93 (s, 3 H) 2.32 (s, 3 H)

LR MS (ES+): 431 (M+Na+)
LR MS (ES−): 407 (M−H)

Example 72

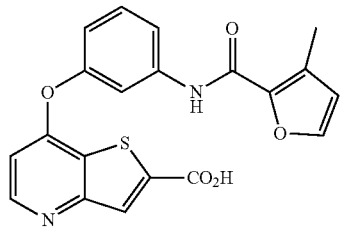 [SMILES: Cc1ccoc1C(=O)Nc1cccc(Oc2ccnc3cc(C(=O)O)sc23)c1]

7-{3-[(3-methyl-2-furoyl)amino]phenoxy}thieno[3,2-b]pyridine-2-carboxylic acid to a stirred solution of methyl 7-{3-[(3-methyl-2-furoyl)amino]phenoxy}thieno[3,2-b]pyridine-2-carboxylate (180 mg, 0.44 mmol) in MeOH (10 ml) was added 1M NaOH (1.5 ml, 1.5 mmol). The mixture was stirred at room temperature for 1 hour, and poured into 100 ml of water. 2M HCl was added until pH=4. The precipitates was filtered, washed with water and dried to give 7-{3-[(3-methyl-2-furoyl)amino]phenoxy}thieno[3,2-b]pyridine-2-carboxylic acid as off-white solid. Yield: 160 mg, ~92%.

$^1$H NMR (300 MHz, DMSO-$d_6$) δ ppm 10.26 (s, 1 H) 8.65 (d, J=5.27 Hz, 1 H) 8.14 (s, 1 H) 7.81 (t, J=2.20 Hz, 1 H) 7.80 (d, J=1.47 Hz, 1 H) 7.76 (ddd, J=8.21, 2.05, 0.88 Hz, 1 H) 7.47 (t, J=8.20 Hz, 1 H) 7.04 (ddd, J=8.21, 2.34, 0.88 Hz, 1 H) 6.87 (d, J=5.57 Hz, 1 H) 6.59 (d, J=1.76 Hz, 1 H) 2.32 (s, 3 H).

Example 73

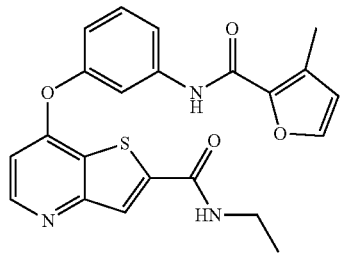 [SMILES: CCNC(=O)c1cc2nccc(Oc3cccc(NC(=O)c4occc4C)c3)c2s1]

N-ethyl-7-{3-[(3-methyl-2-furoyl)amino]phenoxy}thieno[3,2-b]pyridine-2-carboxamide to a stirred, cooled (0° C.) solution of 7-{3-[(3-methyl-2-furoyl)amino]phenoxy}thieno[3,2-b]pyridine-2-carboxylic acid (120 mg, 0.30 mmol) in anhydrous DMF (10 ml) were added PyBOP (171 mg, 0.33 mmol) and N,N-diisopropylethylamine (85 mg, 0.66 mmol). The mixture was stirred at 0° C. for 5 minutes, followed by addition of 2M ethylamine solution in THF (0.18 ml, 0.36 mmol). Stirring was continued at 0° C. for another 40 minutes. The mixture was poured into 100 ml of water with vigorous stirring. 2M HCl was added dropwise until pH=5. The precipitates were filtered, washed with water and dried to give N-ethyl-7-{3-[(3-methyl-2-furoyl)amino]phenoxy}thieno[3,2-b]pyridine-2-carboxamide as light yellow solid. Yield: 115 mg, 90%.

¹H NMR (600 MHz, DMSO-d₆) δ ppm 10.25 (s, 1 H) 8.94 (t, J=5.43 Hz, 1 H) 8.60 (d, J=5.28 Hz, 1 H) 8.24 (s, 1 H) 7.79-7.80 (m, 2 H) 7.75 (ddd, J=8.22, 2.05, 0.88 Hz, 1 H) 7.46 (t, J=8.22 Hz, 1 H) 7.02 (ddd, J=8.14, 2.42, 0.88 Hz, 1 H) 6.82 (d, J=5.28 Hz, 1 H) 6.59 (dd, J=1.76, 0.59 Hz, 1 H) 3.32-3.36 (m, 2 H) 2.32 (s, 3 H) 1.17 (t, J=7.34 Hz, 3 H)

LR MS (ES+): 444 (M+Na⁺)

LR MS (ES−): 420 (M−H)

The compounds of Examples 74-78 below were prepared using procedures similar to those of Example 73.

Example 74

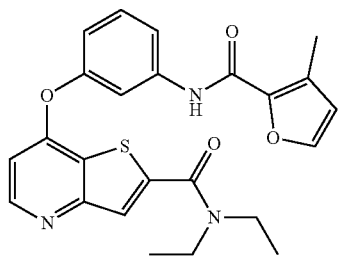 [SMILES: CCN(CC)C(=O)c1cc2nccc(Oc3cccc(NC(=O)c4occc4C)c3)c2s1]

N,N-diethyl-7-{3-[(3-methyl-2-furoyl)amino]phenoxy}thieno[3,2-b]pyridine-2-carboxamide ¹H NMR (600 MHz, DMSO-d₆) δ ppm 10.26 (s, 1 H) 8.61 (d, J=5.58 Hz, 1 H) 7.81 (t, J=2.20 Hz, 1 H) 7.79-7.80 (m, 2 H) 7.75 (ddd, J=8.22, 2.05, 0.88 Hz, 1 H) 7.46 (t, J=8.22 Hz, 1 H) 7.03 (ddd, J=8.07, 2.49, 0.88 Hz, 1 H) 6.82 (d, J=5.28 Hz, 1 H) 6.59 (d, J=1.76 Hz, 1 H) 3.51 (br. s., 4 H) 2.32 (s, 3 H) 1.20 (br. s., 6 H)

LR MS (ES+): 472 (M+Na⁺)

LR MS (ES−): 448 (M−H)

Example 75

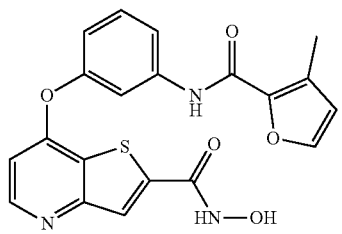 [SMILES: Cc1ccoc1C(=O)Nc1cccc(Oc2ccnc3cc(C(=O)NO)sc23)c1]

N-hydroxy-7-{3-[(3-methyl-2-furoyl)amino]phenoxy}thieno[3,2-b]pyridine-2-carboxamide ¹H NMR (600 MHz, DMSO-d₆) δ ppm 11.70 (s, 1 H) 10.26 (s, 1 H) 9.45 (s, 1 H) 8.60 (d, J=5.28 Hz, 1 H) 8.09 (s, 1 H) 7.79-7.81 (m, 2 H) 7.75 (ddd, J=8.29, 1.98, 0.88 Hz, 1 H) 7.46 (t, J=8.22 Hz, 1 H) 7.02 (ddd, J=8.07, 2.49, 0.88 Hz, 1 H) 6.82 (d, J=5.58 Hz, 1 H) 6.59 (dd, J=1.76, 0.59 Hz, 1 H) 2.32 (s, 3 H)

LR MS (ES+): 431 (M+Na⁺)

LR MS (ES−): 408 (M−H)

Example 76

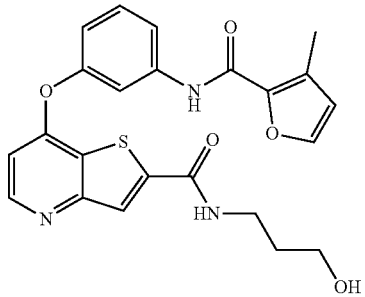

N-(3-hydroxypropyl)-7-{3-[(3-methyl-2-furoyl)amino]phenoxy}thieno[3,2-b]pyridine-2-carboxamide ¹H NMR (600 MHz, DMSO-d₆) δ ppm 10.25 (s, 1 H) 8.92 (t, J=5.58 Hz, 1 H) 8.60 (d, J=5.28 Hz, 1 H) 8.25 (s, 1 H) 7.79-7.81 (m, 2 H) 7.75 (ddd, J=8.22, 2.05, 0.88 Hz, 1 H) 7.46 (t, J=8.22 Hz, 1 H) 7.02 (ddd, J=8.14, 2.42, 0.88 Hz, 1 H) 6.82 (d, J=5.28 Hz, 1 H) 6.59 (d, J=1.76 Hz, 1 H) 4.50 (t, J=5.28 Hz, 1 H) 3.46-3.51 (m, 2 H) 3.33-3.38 (m, 2 H) 2.32 (s, 3 H) 1.68-1.76 (m, 2 H)

LR MS (ES+): 474 (M+Na⁺)

LR MS (ES−): 450 (M−H)

Example 77

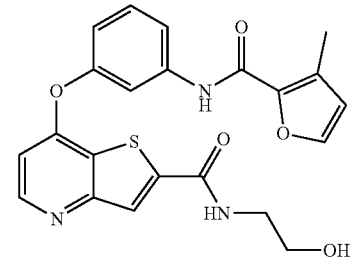 [SMILES: Cc1ccoc1C(=O)Nc1cccc(Oc2ccnc3cc(C(=O)NCCO)sc23)c1]

N-(2-hydroxyethyl)-7-{3-[(3-methyl-2-furoyl)amino]phenoxy}thieno[3,2-b]pyridine-2-carboxamide ¹H NMR (600 MHz, DMSO-d₆) δ ppm 10.25 (s, 1 H) 8.97 (t, J=5.72 Hz, 1 H) 8.60 (d, J=5.28 Hz, 1 H) 8.28 (s, 1 H) 7.79-7.81 (m, 2 H) 7.75 (ddd, J=8.22, 2.05, 0.88 Hz, 1 H) 7.46 (t, J=8.22 Hz, 1 H) 7.02 (ddd, J=8.22, 2.35, 0.88 Hz, 1 H) 6.82 (d, J=5.28 Hz, 1H) 6.59 (d, J=1.47 Hz, 1 H) 4.81 (t, J=5.58 Hz, 1 H) 3.55 (q, J=5.97 Hz, 2 H) 3.37 (q, J=6.06 Hz, 2 H) 2.32 (s, 3 H)

LR MS (ES+): 460 (M+Na⁺)

LR MS (ES−): 436 (M−H)

Example 78

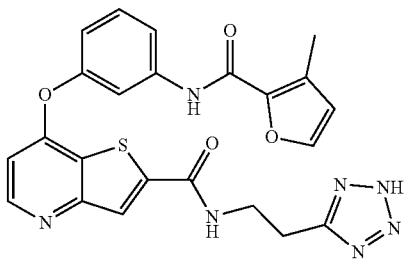 [SMILES: Cc1ccoc1C(=O)Nc1cccc(Oc2ccnc3cc(C(=O)NCCc4nn[nH]n4)sc23)c1]

7-{3-[(3-methyl-2-furoyl)amino]phenoxy}-N-[2-(2H-tetrazol-5-yl)ethyl]thieno[3,2-b]pyridine-2-carboxamide $^1$H NMR (300 MHz, DMSO-d$_6$) δ ppm 10.25 (s, 1 H) 9.13 (t, J=5.57 Hz, 1 H) 8.61 (d, J=5.57 Hz, 1 H) 8.20 (s, 1 H) 7.78-7.81 (m, 2 H) 7.75 (d, J=8.20 Hz, 1 H) 7.46 (t, J=8.06 Hz, 1 H) 7.02 (ddd, J=8.13, 2.42, 0.88 Hz, 1 H) 6.83 (d, J=5.27 Hz, 1 H) 6.59 (d, J=1.47 Hz, 1 H) 3.63-3.70 (m, 2 H) 3.17 (t, J=7.03 Hz, 2 H) 2.32 (s, 3 H)

LR MS (ES+): 490 (MH+)
LR MS (ES−): 488 (M−H)

Example 79

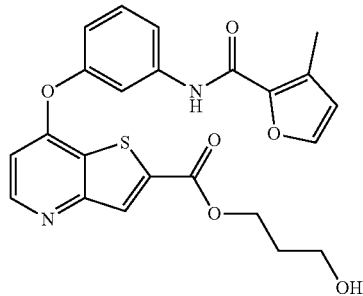 [SMILES: Cc1ccoc1C(=O)Nc1cccc(Oc2ccnc3cc(C(=O)OCCCO)sc23)c1]

3-hydroxypropyl 7-{3-[(3-methyl-2-furoyl)amino]phenoxy}thieno[3,2-b]pyridine-2-carboxylate to a stirred solution of 7-{3-[(3-methyl-2-furoyl)amino]phenoxy}thieno[3,2-b]pyridine-2-carboxylic acid (120 mg, 0.30 mmol) in anhydrous DMF (10 ml) were added 3-bromo-1-propanol (63 mg, 0.45 mmol) and potassium carbonate (83 mg, 0.60 mmol). The mixture was heated at 50° C. for 5 hours and poured into 100 ml of water. The precipitates were filtered, washed with water and dried to give the crude, which was purified by silica gel chromatography eluting with 3~5% of methanol in chloroform to give 3-hydroxypropyl 7-{3-[(3-methyl-2-furoyl)amino]phenoxy}thieno[3,2-b]pyridine-2-carboxylate as white solid. Yield: 25 mg, 18%.

$^1$H NMR (600 MHz, DMSO-d$_6$) δ ppm 10.27 (s, 1 H) 8.67 (d, J=5.28 Hz, 1 H) 8.24 (s, 1 H) 7.82 (t, J=2.20 Hz, 1 H) 7.80 (d, J=1.47 Hz, 1 H) 7.76 (dt, J=9.24, 0.95 Hz, 1 H) 7.48 (t, J=8.22 Hz, 1 H) 7.04 (ddd, J=8.07, 2.49, 0.88 Hz, 1 H) 6.89 (d, J=5.28 Hz, 1 H) 6.60 (d, J=1.47 Hz, 1 H) 4.61 (t, J=5.14 Hz, 1 H) 4.42 (t, J=6.60 Hz, 2 H) 3.55-3.59 (m, 2 H) 2.32 (s, 3 H) 1.88 (quin, J=6.31 Hz, 2 H)

LR MS (ES+): 475 (M+Na$^+$)
LR MS (ES−): 451 (M−H)

The compounds of Examples 80-81 below were prepared using procedures similar to those of Example 79.

Example 80

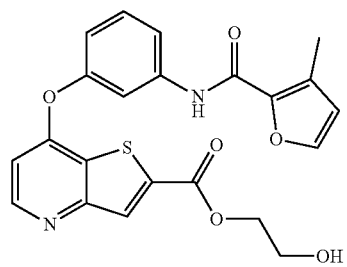

2-hydroxyethyl 7-{3-[(3-methyl-2-furoyl)amino]phenoxy}thieno[3,2-b]pyridine-2-carboxylate $^1$H NMR (600 MHz, DMSO-d$_6$) δ ppm 10.27 (s, 1 H) 8.68 (d, J=5.58 Hz, 1 H) 8.29 (s, 1 H) 7.82 (t, J=2.20 Hz, 1 H) 7.80 (d, J=1.17 Hz, 1 H) 7.76 (ddd, J=8.36, 1.91, 0.88 Hz, 1 H) 7.48 (t, J=8.22 Hz, 1 H) 7.05 (ddd, J=8.22, 2.35, 0.88 Hz, 1 H) 6.89 (d, J=5.58 Hz, 1 H) 6.59-6.60 (m, 1 H) 4.99 (t, J=5.72 Hz, 1 H) 4.36 (dd, J=5.43, 4.55 Hz, 2 H) 3.71-3.75 (m, 2 H) 2.32 (s, 3 H)

LR MS (ES+): 461 (M+Na$^+$)
LR MS (ES−): 437 (M−H)

Example 81

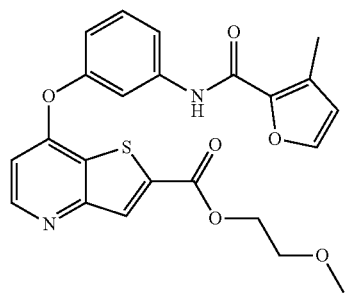 [SMILES: COCCOC(=O)c1cc2nccc(Oc3cccc(NC(=O)c4occc4C)c3)c2s1]

2-methoxyethyl 7-{3-[(3-methyl-2-furoyl)amino]phenoxy}thieno[3,2-b]pyridine-2-carboxylate $^1$H NMR (300 MHz, DMSO-d$_6$) δ ppm 10.27 (s, 1 H) 8.68 (d, J=5.27 Hz, 1 H) 8.24 (s, 1 H) 7.82 (t, J=2.20 Hz, 1 H) 7.80 (d, J=1.17 Hz, 1 H) 7.76 (ddd, J=8.20, 2.05, 0.88 Hz, 1 H) 7.47 (t, J=8.20 Hz, 1 H) 7.05 (ddd, J=8.13, 2.42, 0.88 Hz, 1 H) 6.90 (d, J=5.27 Hz, 1 H) 6.60 (d, J=1.47 Hz, 1 H) 4.46-4.50 (m, 2 H) 3.66-3.71 (m, 2 H) 3.33 (s, 3 H) 2.32 (s, 3 H)

LR MS (ES+): 453 (MH+)
LR MS (ES−): 451 (M−H)

Example 82

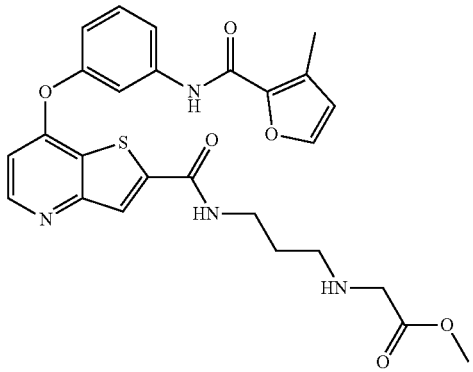 [SMILES: COC(=O)CNCCCNC(=O)c1cc2nccc(Oc3cccc(NC(=O)c4occc4C)c3)c2s1]

Methyl [(3-{[(7-{3-[(3-methyl-2-furoyl)amino]phenoxy}thieno[3,2-b]pyridin-2-yl)carbonyl]amino}propyl)amino]acetate to a stirred, cooled (0° C.) solution of 7-{3-[(3-methyl-2-furoyl)amino]phenoxy}thieno[3,2-b]pyridine-2-carboxylic acid (150 mg, 0.38 mmol) in anhydrous DMF (10 ml) were added PyBOP (218 mg, 0.42 mmol) and N,N-diisopropylethylamine (245 mg, 1.9 mmol). The mixture was stirred at 0° C. for 10 minutes, followed by addition of methyl [(3-aminopropyl)amino]acetate dihydrochloride (100 mg, 0.46 mmol). Stirring was continued at 0° C. for another 40 minutes. The mixture was diluted with ethyl acetate (100 ml), washed with brine (4×100 ml), dried over $Na_2SO_4$, and concentrated to give the crude, which was purified by silica gel chromatography eluting with 5-8% methanol in chloroform to give methyl [(3-{[(7-{3-[(3-methyl-2-furoyl)amino]phenoxy}thieno[3,2-b]pyridin-2-yl)carbonyl]amino}propyl)amino]acetate as light beige solid. Yield: 98 mg, 49%.

$^1$H NMR (600 MHz, DMSO-$d_6$) δ ppm 10.25 (s, 1 H) 8.95 (t, J=5.58 Hz, 1 H) 8.60 (d, J=5.58 Hz, 1 H) 8.23 (s, 1 H) 7.79-7.80 (m, 2 H) 7.73-7.76 (m, 1 H) 7.46 (t, J=8.22 Hz, 1 H) 7.02 (ddd, J=8.14, 2.42, 0.88 Hz, 1 H) 6.82 (d, J=5.58 Hz, 1 H) 6.59 (d, J=1.17 Hz, 1 H) 3.62 (s, 3 H) 3.32-3.36 (m, 4 H) 2.58 (t, J=6.75 Hz, 2 H) 2.32 (s, 3 H) 2.05 (br. s., 1 H) 1.68 (quin, J=6.90 Hz, 2 H)

LR MS (ES+): 545 (M+Na$^+$)
LR MS (ES−): 521 (M−H)

Example 82A

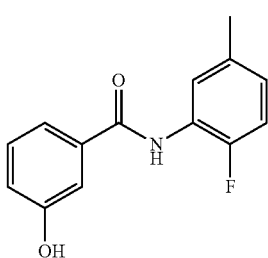 [SMILES: Cc1ccc(F)c(NC(=O)c2cccc(O)c2)c1]

N-(2-fluoro-5-methylphenyl)-3-hydroxybenzamide

Step 1: To a stirred solution of 3-benzyloxy benzoic acid (1.00 g, 4.38 mmol) in 20 ml of anhydrous DMF were added HATU (1.83 g, 4.82 mmol) and DIPEA (1.7 ml, 9.6 mmol). The mixture was stirred at room temperature for 10 minutes, followed by addition of 2-fluoro-5-methylaniline (657 mg, 5.25 mmol). The mixture was heated at 66° C. for 16 hours, cooled to room temperature, and partitioned between EtOAc (100 ml) and 0.5M HCl (200 ml). The organic phase was washed with 0.5M HCl (2×50 ml), saturated NaHCO$_3$ (50 ml) and brine (50 ml), dried over Na$_2$SO$_4$, and evaporated to dryness to afford 3-(benzyloxy)-N-(2-fluoro-5-methylphenyl)benzamide as light brown solid. Yield: 1.5 g, 100%.

Step 2: A solution of 3-(benzyloxy)-N-(2-fluoro-5-methylphenyl)benzamide (1.5 g, 4.48 mmol from Step 1) in 20 ml of MeOH containing 10% Pd/C (150 mg) was stirred under a hydrogen balloon at room temperature for 2 hours. The catalyst was removed by filtration. The filtrate solution was evaporated to dryness under reduced pressure to give N-(2-fluoro-5-methylphenyl)-3-hydroxybenzamide as light-beige solid. Yield: 1.1 g, 100%.

$^1$H NMR (600 MHz, DMSO-$d_6$) δ ppm 9.92 (s, 1 H) 9.75 (br. s., 1 H) 7.37-7.40 (m, 2 H) 7.33 (t, J=2.05 Hz, 1 H) 7.31 (t, J=7.78 Hz, 1 H) 7.15 (dd, J=10.56, 8.51 Hz, 1 H) 7.03-7.07 (m, 1 H) 6.96-6.99 (m, 1 H) 2.30 (s, 3 H)

LR MS (ES+): 268 (M+Na$^+$)
LR MS (ES−): 244 (M−H)

Example 83

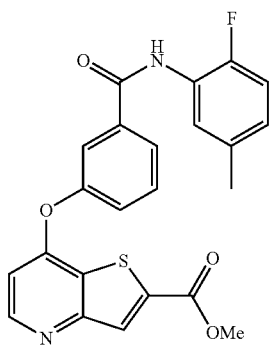 [SMILES: COC(=O)c1cc2nccc(Oc3cccc(C(=O)Nc4cc(C)ccc4F)c3)c2s1]

Methyl 7-(3-((2-fluoro-5-methylphenyl)carbamoyl)phenoxy)thieno[3,2-b]pyridine-2-carboxylate a mixture of N-(2-fluoro-5-methylphenyl)-3-hydroxybenzamide (270 mg, 1.1 mmol), methyl 7-chlorothieno[3,2-b]pyridine-2-carboxylate (300 mg, 1.3 mmol) and cesium carbonate (1.0 g, 3.07 mmol) in 10 ml of anhydrous DMSO was heated at 68° C. for 16 hours, cooled to room temperature and partitioned between water (100 ml) and EtOAc (100 ml). The aqueous layer was extracted with more EtOAc (2×50 ml). All the organic layers were combined, washed with brine (50 ml), dried over Na$_2$SO$_4$, and evaporated to dryness to give the crude, which was purified by silica gel chromatography eluted with 1~2% of MeOH in CHCl$_3$ to give methyl 7-(3-((2-fluoro-5-methylphenyl)carbamoyl)phenoxy)thieno[3,2-b]pyridine-2-carboxylate as light brown oil.

Yield: 170 mg, 37%.

Example 84

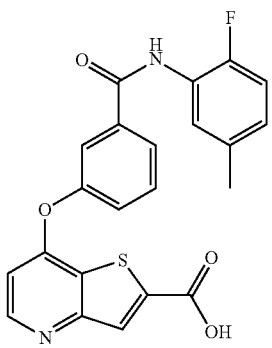 [SMILES: Cc1ccc(F)c(NC(=O)c2cccc(Oc3ccnc4cc(C(=O)O)sc34)c2)c1]

7-(3-{[(2-fluoro-5-methylphenyl)amino]carbonyl}phenoxy)thieno[3,2-b]pyridine-2-carboxylic acid to a stirred solution of methyl 7-(3-((2-fluoro-5-methylphenyl)carbamoyl)phenoxy)thieno[3,2-b]pyridine-2-carboxylate (170 mg, 0.39 mmol) in 15 ml of MeOH was added 1 ml of 1M NaOH. Reaction was complete within 2.5 hours. The mixture was poured into 100 ml of water and acidified with 2M HCl to pH=5 with vigorous stirring. The precipitates were filtered, washed with water and dried in vacuo to give 7-(3-{[(2-fluoro-5-methylphenyl)amino]carbonyl}phenoxy)thieno[3,2-b]pyridine-2-carboxylic acid as white solid. Yield: 150 mg, 91%.

$^1$H NMR (600 MHz, DMSO-$d_6$) δ ppm 13.96 (br. s., 1 H) 10.15 (s, 1 H) 8.66 (d, J=4.40 Hz, 1 H) 8.15 (s, 1 H) 7.97 (d, J=7.92 Hz, 1 H) 7.90 (s, 1 H) 7.70 (t, J=7.92 Hz, 1 H) 7.60 (dd, J=8.07, 1.61 Hz, 1 H) 7.38 (dd, J=7.34, 1.76 Hz, 1 H) 7.16 (dd, J=10.42, 8.36 Hz, 1 H) 7.04-7.09 (m, 1 H) 6.87 (d, J=5.28 Hz, 1 H) 2.29 (s, 3 H)

LR MS (ES+): 423 (MH$^+$)
LR MS (ES−): 421 (M−H)

Example 85

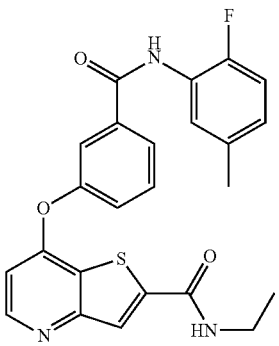 [SMILES: CCNC(=O)c1cc2nccc(Oc3cccc(C(=O)Nc4cc(C)ccc4F)c3)c2s1]

N-ethyl-7-(3-{[(2-fluoro-5-methylphenyl)amino]carbonyl}phenoxy)thieno[3,2-b]pyridine-2-carboxamide to a stirred, cooled (0° C.) solution of 7-(3-{[(2-fluoro-5-methylphenyl)amino]carbonyl}phenoxy)thieno[3,2-b]pyridine-2-carboxylic acid (120 mg, 0.28 mmol) in anhydrous DMF (10 ml) were added PyBOP (161 mg, 0.31 mmol) and N,N-diisopropylethylamine (72 mg, 0.56 mmol). The mixture was stirred at 0° C. for 5 minutes, followed by addition of 2M ethylamine solution in THF (0.2 ml, 0.4 mmol). Stirring was continued at 0° C. for another 30 minutes. The mixture was poured into 100 ml of water with vigorous stirring. 2M HCl was added dropwise until pH=4. The precipitates were filtered, washed with water and dried to give N-ethyl-7-(3-{[(2-fluoro-5-methylphenyl)amino]carbonyl}phenoxy)thieno[3,2-b]pyridine-2-carboxamide as yellow solid. Yield: 112 mg, 88%.

$^1$H NMR (600 MHz, DMSO-$d_6$) δ ppm 10.15 (s, 1 H) 8.96 (t, J=5.58 Hz, 1 H) 8.62 (d, J=5.58 Hz, 1 H) 8.26 (s, 1 H) 7.96 (dd, J=7.78, 1.03 Hz, 1 H) 7.87-7.89 (m, 1 H) 7.69 (t, J=7.92 Hz, 1 H) 7.58 (ddd, J=8.14, 2.57, 1.03 Hz, 1 H) 7.38 (dd, J=7.34, 1.76 Hz, 1 H) 7.16 (dd, J=10.42, 8.36 Hz, 1 H) 7.05-7.09 (m, 1 H) 6.83 (d, J=5.58 Hz, 1 H) 3.34 (qd, J=7.24, 5.58 Hz, 2 H) 2.29 (s, 3 H) 1.17 (t, J=7.34 Hz, 3 H)

LR MS (ES+): 472 (M+Na$^+$)
LR MS (ES−): 448 (M−H)

The compound of Examples 86 below was prepared using procedures similar to those used to prepare the compound of Example 85.

Example 86

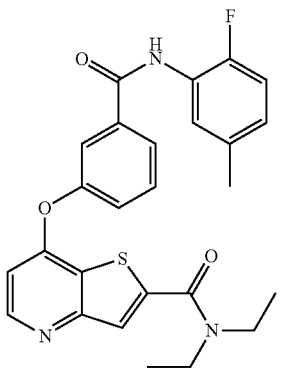 [SMILES: CCN(CC)C(=O)c1cc2nccc(Oc3cccc(C(=O)Nc4cc(C)ccc4F)c3)c2s1]

N,N-diethyl-7-(3-{[(2-fluoro-5-methylphenyl)amino]carbonyl}phenoxy)thieno[3,2-b]pyridine-2-carboxamide $^1$H NMR (600 MHz, DMSO-$d_6$) δ ppm 10.15 (s, 1 H) 8.62 (d, J=5.28 Hz, 1 H) 7.97 (d, J=7.92 Hz, 1 H) 7.89-7.90 (m, 1 H) 7.82 (s, 1 H) 7.69 (t, J=7.92 Hz, 1 H) 7.58 (ddd, J=8.07, 2.49, 1.17 Hz, 1 H) 7.38 (dd, J=7.19, 1.91 Hz, 1 H) 7.16 (dd, J=10.42, 8.36 Hz, 1 H) 7.07 (td, J=5.21, 2.49 Hz, 1 H) 6.83 (d, J=5.58 Hz, 1 H) 3.52 (br. s., 4 H) 2.29 (s, 3 H) 1.21 (br. s., 6 H)

LR MS (ES+): 500 (M+Na$^+$)
LR MS (ES−): 476 (M−H)

Example 87

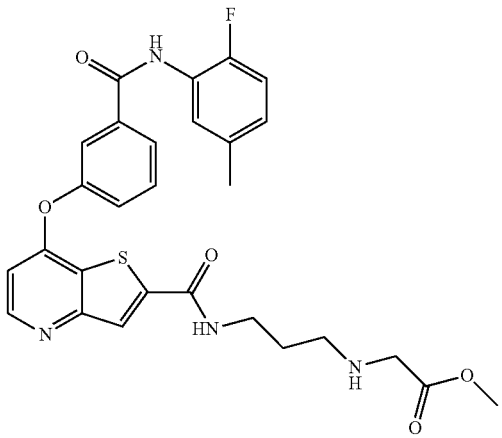 [SMILES: COC(=O)CNCCCNC(=O)c1cc2nccc(Oc3cccc(C(=O)Nc4cc(C)ccc4F)c3)c2s1]

Methyl {[3-({[7-(3-{[(2-fluoro-5-methylphenyl)amino]carbonyl}phenoxy)thieno[3,2-b]pyridin-2-yl]carbonyl}amino)propyl]amino}acetate to a stirred, cooled (0° C.) solution of 7-(3-{[(2-fluoro-5-methylphenyl)amino]carbonyl}phenoxy)thieno[3,2-b]pyridine-2-carboxylic acid (80 mg, 0.19 mmol) in anhydrous DMF (10 ml) were added PyBOP (109 mg, 0.21 mmol) and N,N-diisopropylethylamine (123 mg, 0.95 mmol). The mixture was stirred at 0° C. for 10 minutes, followed by addition of methyl [(3-aminopropyl)amino]acetate dihydrochloride (50 mg, 0.23 mmol). Stirring was continued at 0° C. for 10 minutes then room temperature for 2 hours. The mixture was poured into 100 ml of water with vigorous stirring. The precipitates were filtered, washed with water and dried to give the crude, which was purified by silica gel chromatography eluting with 5-8% methanol in chloroform to give methyl {[3-({[7-(3-{[(2-fluoro-5-methylphenyl)amino]carbonyl}phenoxy)thieno[3,2-b]pyridin-2-yl]carbonyl}amino)propyl]amino}acetate as light beige solid. Yield: 40 mg, 38%.

$^1$H NMR (600 MHz, DMSO-$d_6$) δ ppm 10.15 (s, 1 H) 8.97 (t, J=5.58 Hz, 1 H) 8.62 (d, J=5.28 Hz, 1 H) 8.25 (s, 1 H) 7.96 (dt, J=7.70, 1.28 Hz, 1 H) 7.87-7.89 (m, 1 H) 7.69 (t, J=7.92 Hz, 1 H) 7.58 (ddd, J=8.14, 2.42, 0.88 Hz, 1 H) 7.38 (dd, J=7.19, 1.91 Hz, 1 H) 7.16 (dd, J=10.56, 8.51 Hz, 1 H) 7.05-7.08 (m, 1 H) 6.83 (d, J=5.28 Hz, 1 H) 3.62 (s, 3 H) 3.34-3.37 (m, 4 H) 2.59 (t, J=6.90 Hz, 2 H) 2.29 (s, 3 H) 1.68 (quin, J=6.97 Hz, 2 H)

LR MS (ES+): 551 (MH$^+$)

4. Biological Testing

Biological data for the compounds of the present invention was generated by the use of one or more of the following assays.

VEGF Stimulated Ca.Sup.++ Signal In Vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight at 37 .degree. C./5% CO.sub.2. Cells were loaded with calcium indicator Fluo-4 for 45 minutes at 37 .degree. C. Cells were washed 4 times (Original Cell Wash, Labsystems) to remove extracellular dye. Test compounds were reconstituted in 100% DMSO and added to the cells to give a final DMSO concentration of 0.1%. For screening, cells were pre-incubated with test agents for 30 minutes, at a single concentration (10 .mu.M) or at concentrations ranging from 0.01 to 10.0 .mu.M followed by VEGF stimulation (5 ng/mL). Changes in fluorescence at 516 nm were measured simultaneously in all 96 wells using a cooled CCD camera. Data were generated by determining max-min fluorescence levels for unstimulated, stimulated, and drug treated samples. IC.sub.50 values for test compounds were calculated from % inhibition of VEGF stimulated responses in the absence of inhibitor.

VEGFR2 Kinase Assay

The cytoplasmic domain of the human VEGF receptor (VEGFR-2) was expressed as a Histidine-tagged fusion protein following infection of insect cells using an His engineered baculovirus. His-VEGFR-2 was purified to homogeneity, as determined by SDS-PAGE, using nickel resin chromatography. Kinase assays were performed in 96 well microtiter plates that were coated overnight with 30 .mu.g of poly-Glu-Tyr (4:1) in 10 mM Phosphate Buffered Saline (PBS), pH 7.2-7.4. The plates were incubated with 1% BSA and then washed four times with PBS prior to starting the reaction. Reactions were carried out in 120 .mu.L reaction volumes containing 3.6 .mu.M ATP in kinase buffer (50 mM Hepes buffer pH 7.4, 20 mM MgCl.sub.2, 0.1 mM MnCl.sub.2 and 0.2 mM Na.sub.3 VO.sub.4). Test compounds were reconstituted in 100% DMSO and added to the reaction to give a final DMSO concentration of 5%. Reactions were initiated by the addition 0.5 ng of purified protein. Following a ten minute incubation at 25 .degree. C., the reactions were washed four times with PBS containing 0.05% Tween-20. 100 .mu.l of a monoclonal anti-phosphotyrosine antibody-peroxidase conjugate was diluted 1:10000 in PBS-Tween-20 and added to the wells for 30 minutes. Following four washes with PBS-Tween-20, 100 .mu.l of O-phenylenediamine Dihydrochloride in Phosphate-citrate buffer, containing urea hydrogen peroxide, was added to the wells for 7 minutes as a colorimetric substrate for the peroxidase.

The reaction was terminated by the addition of 100 .mu.l of 2.5N H.sub.2 SO.sub.4 to each well and read using a microplate ELISA reader set at 492 nm. IC.sub.50 values for compound inhibition were calculated directly from graphs of optical density (arbitrary units) versus compound concentration following subtraction of blank values.

VEGF-induced Dermal Extravasation in Guinea Pig (Miles Assay)

Male Hartley guinea pigs (300-600 g) were anesthetized with isofluorane, sheared, and given a single dose of drug or the respective vehicle. The guinea pigs were dosed orally unless indicated otherwise in Table 3. Ten minutes prior to the end of drug treatment, guinea pigs were anesthetized with isofluorane, and 0.5% Evans blue dye (EBD) in PBS (13-15 mg/kg dose of EBD) was injected intravenously. After 5 minutes, triplicate intradermal injections of 100 ng rhVEGF.sub.165 in 100 .mu.l PBS and of 100 .mu.l PBS alone were administered on the flank. After 20 minutes, each animal was euthanized with Pentosol, and the skin containing the intradermal injection sites was removed for image analysis. Using an analog video camera coupled to a PC, an image of each trans-illuminated skin sample was captured, and the integrated optical density of each injection site was measured using ImagePro 4. For each skin sample, the difference between the mean optical density of the VEGF sites and mean optical density of the PBS sites is the measure of VEGF-induced EBD extravasation in that animal. These measured values were averaged per study group to determine the mean VEGF-induced EBD extravasation for each experimental condition, and the group means were then compared to assess inhibition of VEGF-induced EBD extravasation in the drug-treated groups relative to the vehicle-treated controls. To determine the dose required for 50% inhibition (ID.sub.50), the percent inhibition data was plotted as a function of oral dose, using the 'best-fit' analysis within MicroSoft Excel software. The ID.sub.50 value was verified visually by using the plotted data (horizontal line from 50% y value, at intersection with best-fit line drop vertical line to x axis (dose).

Laser-induced Choroidal Neovascularization (CNV) in Rat (CNV Assay)

CNV was induced and quantified in this model as previously described (Edelman and Castro. Exp. Eye Res. 2000; 71:523-533). On day 0, male Brown Norway rats (200-300 g) were anesthetized with 100 mg/kg Ketamine and 10 mg/kg Xylazine, and pupils were dilated with 1% Tropicamide. Using the blue-green setting of a Coherent Novus Argon Laser, 3 laser burns (90 mW for 0.1 s; 100 .mu.m diameter) were given to each eye between the retinal vessels around the optic nerve head. Rats were dosed with test compounds in their indicated vehicles orally once daily.

On day 10, rats were sacrificed with 100% $CO_2$, and blood vessels were labeled by vascular perfusion with 10 mg/ml FITC-dextran (MW $2 \times 10^6$). Using an epi-fluorescence microscope (20.times.) coupled to a spot digital camera and a PC, images were obtained from the flat mounts of the RPE-choroid-sclera from each eye, and the area occupied by hyperfluorescent neovessels within each laser lesion was measured using ImagePro 4 software.

To determine the dose required for 50% inhibition ($ID_{50}$), the percent inhibition data was plotted as a function of oral dose, using the 'best-fit' analysis within MicroSoft Excel software. The $ID_{50}$ value was verified visually by using the plotted data (horizontal line from 50% y value, at intersection with best-fit line drop vertical line to x axis (dose).

Rabbit Eye VEGF Permeability Model

Assay used was detailed by Jeffrey Edelman, etc in Exp. Eye. Res. 80(2005), Pg 249-258.

PDGF Stimulated $Ca^{2+}$ Signal In Vitro

Automated FLIPR (Fluorometric Imaging Plate Reader) technology was used to screen for inhibitors of PDGF induced increases in intracellular calcium levels in fluorescent dye loaded endothelial cells. NHDF-Ad (Normal human dermal fibroblasts) (Lonza) were seeded in 384-well fibronectin coated black-walled plates overnight at 37° C./5% $CO_2$. Cells were loaded with calcium indicator Fluo-4 for 45 minutes at 37° C. Cells were washed 4 times (ELx405-CW, Bio-Tek) to remove extracellular dye. Test compounds were reconstituted in 100% DMSO and added to the cells to give a final DMSO concentration of 0.1%. For screening, cells were pre-incubated with test agents for 30 minutes, at a single concentration (10 µM) or at concentrations ranging from 0.001 nM to 10 µM followed by PDGF stimulation (10 ng/mL). Changes in fluorescence at 515 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF stimulated responses in the absence of inhibitor.

TABLE II

Biological Activities of Compounds of the Present Invention

| Compound | Cellular VEGFR2 $IC_{50}$ (nM) | Enzymic VEGFR2 $IC_{50}$ (nM) | Enzymic VEGFR1 $IC_{50}$ (nM) | In Vivo Rabbit Eye VEGF Permeability |
|---|---|---|---|---|
| F1 | 2 | 18 | | |
| F2 | 29 | 20 | 16 | efficacious |
| F3 | 35 | 21 | | |
| F4 | $10^4$ | $10^4$ | | |
| F5 | $10^4$ | $10^4$ | | |
| F6 | | 11 | | |
| F7 | | 10 | | |
| F8 | | 11 | | |

| Example | Cellular VEGFR2 $IC_{50}$ (nM) | Enzymic VEGFR2 $IC_{50}$ (nM) | Enzymic VEGFR1 $IC_{50}$ (nM) | Enzymic PDGFRβ $IC_{50}$ (nM) | In Vivo Rabbit Eye VEGF Permeability |
|---|---|---|---|---|---|
| 12 | 126 | 3 | 4 | 20 | |
| 13 | 97 | 6 | 10 | 19 | |
| 14 | 34 | 4 | 5 | 13 | |
| 15 | 39 | 3 | 3 | 10 | |
| 16 | | 7 | 10 | 15 | |
| 17 | | 4 | 10 | 15 | |
| 18 | 0.8 | 3 | 6 | 11 | Efficacious |
| 19 | 0.3 | 4 | 9 | 14 | |
| 23 | 9 | 7 | 13 | 14 | |
| 24 | 14 | 10 | 9 | 14 | |
| 25 | | 5 | 8 | 11 | |
| 26 | | 5 | 10 | 12 | |
| 27 | | 16 | 11 | 17 | |
| 28 | | 5 | 8 | 17 | |
| 29 | | 5 | 10 | 13 | |
| 30 | | 7 | 112 | 17 | |
| 31 | | 9 | 9 | 13 | |
| 32 | | 4 | 11 | 15 | |
| 33 | | 24 | 60 | 69 | |
| 34 | | 3 | 6 | 11 | |
| 36 | | 7 | 8 | | |
| 37 | 1 | 7 | 9 | | |
| 38 | 14 | 7 | 8 | | |
| 39 | 2 | 5 | 8 | | |
| 42 | 4 | 6 | | | |
| 43 | 6 | 3 | | | |
| 44 | 16 | 11 | | | |
| 45 | 10 | 7 | | | |
| 46 | 328 | 19 | | | Efficacious |
| 48 | | 7 | | | |
| 50 | 80 | 16 | 18 | | |
| 53 | | 12 | | | |
| 54 | 4 | 34 | | | |
| 55 | 7 | 11 | 7 | | Efficacious |
| 56 | | 20 | 16 | | |
| 57 | 1 | 14 | 15 | | |
| 58 | | 3 | | | |
| 61 | | 2 | | | |
| 64 | | 13 | 7 | | |
| 65 | 2 | 12 | 7 | | |
| 66 | 16 | 4 | | 16 | |
| 67 | 2 | 2 | | 9 | |
| 68 | 20 | 6 | | 16 | |
| 69 | 11 | 4 | 5 | 13 | |
| 70 | 9 | 3 | 3 | 12 | |
| 71 | | 24 | | 169 | |
| 72 | 162 | 39 | | 920 | |
| 73 | | 9 | | 191 | |
| 74 | | 27 | | 424 | |
| 75 | 16 | 11 | | 277 | |
| 76 | | 11 | | 146 | |
| 77 | | 17 | | 392 | |
| 78 | | 14 | | 323 | |
| 79 | | 9 | | 146 | |
| 80 | | 17 | | 212 | |
| 81 | | 19 | | 273 | |
| 82 | | 11 | | 238 | |
| 84 | 87 | 20 | | 223 | |
| 85 | 16 | 10 | | 74 | |
| 86 | 64 | 7 | | 206 | |
| 87 | 9 | 16 | | 59 | |

What is claimed is:

1. The 7-[4-({[(2-fluoro-5-methylphenyl)amino]carbonyl}amino)phenoxy]-N-[3-(2H-tetrazol-5-yl)propyl]thieno[3,2-b]pyridine-2-carboxamide; or a pharmaceutically acceptable salt thereof.

2. A pharmaceutical composition comprising a therapeutic effective amount of the compound of claim 1, or a pharmaceutically acceptable salt thereof, and at least one pharmaceutically acceptable carrier.

* * * * *